United States Patent
Hirai et al.

(10) Patent No.: US 8,425,988 B2
(45) Date of Patent: Apr. 23, 2013

(54) POLYMERIZABLE LIQUID CRYSTAL COMPOUND, POLYMERIZABLE LIQUID CRYSTAL COMPOSITION AND ANISOTROPIC POLYMER

(75) Inventors: Yoshiharu Hirai, Ichihara (JP); Takashi Kato, Ichihara (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 147 days.

(21) Appl. No.: 12/974,975

(22) Filed: Dec. 21, 2010

(65) Prior Publication Data
US 2011/0147657 A1   Jun. 23, 2011

(30) Foreign Application Priority Data

Dec. 22, 2009  (JP) ................. 2009-290379
Nov. 11, 2010  (JP) ................. 2010-253089

(51) Int. Cl.
    *C09K 19/34* (2006.01)
    *C09K 19/32* (2006.01)
    *C09K 19/20* (2006.01)
    *C09K 19/38* (2006.01)
    *C07C 69/76* (2006.01)
    *C07D 305/06* (2006.01)
    *C07D 303/22* (2006.01)
    *C07D 493/04* (2006.01)
    *C07D 207/448* (2006.01)
    *C07D 207/452* (2006.01)

(52) U.S. Cl.
USPC ............... 428/1.1; 252/299.61; 252/299.62; 252/299.67; 548/548; 549/510; 549/547; 549/560; 560/85

(58) Field of Classification Search ............ 560/76, 560/85; 252/299.67, 299.61, 299.62; 428/1.1; 349/117, 183; 548/548; 549/510, 547, 560
See application file for complete search history.

(56) References Cited

U.S. PATENT DOCUMENTS

| | | | |
|---|---|---|---|
| 5,593,617 A * | 1/1997 | Kelly et al. | 252/299.67 |
| 5,707,544 A * | 1/1998 | Kelly | 252/299.01 |
| 7,919,648 B2 * | 4/2011 | Kato | 560/65 |
| 7,927,671 B2 * | 4/2011 | Kato | 428/1.1 |
| 2004/0222403 A1 | 11/2004 | Sasada et al. | |
| 2006/0222784 A1 | 10/2006 | Saigusa et al. | |
| 2006/0278851 A1 | 12/2006 | Ito et al. | |

FOREIGN PATENT DOCUMENTS

| | | |
|---|---|---|
| JP | 2002-372623 A | 12/2002 |
| JP | 2006-111571 A | 4/2006 |
| JP | 2006-285014 A | 10/2006 |

OTHER PUBLICATIONS

CAPLUS 1996: 338697.*
Thomsen III et al. "Liquid Crystal Elastomers with Mechanical Properties of a Muscle", Macromolecules 2001, 34, pp. 5868-5875.*

* cited by examiner

*Primary Examiner* — Shean C Wu
(74) *Attorney, Agent, or Firm* — Hogan Lovells US LLP

(57) ABSTRACT

The main aim of the invention is to provide a polymerizable compound that is excellent in the stability of a liquid crystal phase, a polymerizable liquid crystal composition, and an anisotropic polymer in which the optical anisotropy can be adjusted and a uniform orientation is excellent. An anisotropic polymer having a uniform orientation formed by polymerization of a paint film that was prepared by application of a polymerizable liquid crystal composition including a compound represented by formula (1) having a benzyl ester moiety in the minor axis direction of the molecule to a supporting substrate; wherein at least one of $R^a$ is a polymerizable group, A is a divalent cyclic-structure group, B is phenyl that may have a substituent, Y and Z are a single bond or alkylene, and m and n are an integer from 0 to 5.

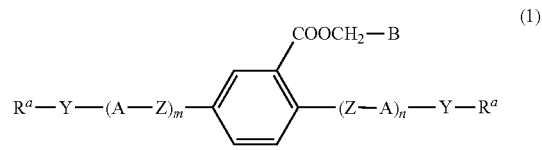

(1)

32 Claims, 2 Drawing Sheets

POLYMERIZABLE LIQUID CRYSTAL COMPOUND, POLYMERIZABLE LIQUID CRYSTAL COMPOSITION AND ANISOTROPIC POLYMER

This nonprovisional application claims priority under 35 U.S.C. §119(a) on Patent Application No. 2009-290379 filed in Japan on Dec. 12, 2009 and Patent Application No. 2010-253089 filed in Japan on Nov. 11, 2010, the entire contents of which are hereby incorporated by reference.

BACKGROUND OF THE INVENTION

1. Field of the Invention

The invention relates to a compound having a benzyl ester moiety in the minor axis direction of the molecule, a polymerizable liquid crystal composition including the compound, an anisotropic polymer formed from the polymerizable liquid crystal composition, a polymer film and their use.

2. Related Art

A polymerizable compound having a liquid crystal phase gives a polymer having a function such as optical compensation by polymerization. This is because the orientation of liquid crystal molecules is fixed by polymerization. A variety of polymerizable compounds have been studied in order to utilize such a function. However, it does not seem that one polymerizable compound have a sufficient function. Thus, the method has been tried in which a composition is prepared from some polymerizable compounds and the composition is polymerized (see the patent documents Nos. 1 and 2).

When liquid crystal molecules exhibit orientation such as homogeneous, tilted, homeotropic and twisted in this specification, they may be expressed as "having a homogeneous orientation", "having a tilted orientation", "having a homeotropic orientation", and "having a twisted orientation", respectively. For example, a liquid crystal film with a homogeneous molecular orientation, that is to say, a liquid crystal film that is oriented homogeneously, may be referred to as a liquid crystal film having a homogeneous orientation or a liquid crystal film of a homogeneous orientation.

A polymer having a homogeneous orientation can be used by way of a combination with a half-wave plate, a quarter-wave plate or a film having other optical functions (see the patent document No. 3). For the usage described above, a polymerizable liquid crystal material may sometimes be cumulated on a glass substrate, a glass substrate whose surface is covered with a plastic thin film (for example, an over-coated film formed on a color filter), a color filter-substrate (see the patent document No. 4) or a plastic substrate. Examples of a material used as a plastic substrate include polymers of TAC (triacetyl cellulose), polycarbonate, PET and cycloolefin-based resins.

The present inventors have found a polymerizable liquid crystal composition that maintains a liquid crystal phase stably also at room temperature and exhibits a uniform orientation (see the patent document No. 5). However, unresolved issues remain in which the liquid crystal phase cannot always be maintained when the composition ratio is changed in order to decrease the optical anisotropy (Δn). The addition of a compound having an aromatic ring (a compound having a triptycene ring) in the minor axis direction has been proposed as a method for adjusting the optical anisotropy. Even in this method, there are cases where crystallization occurs when a large amount of the compound is added to the composition, and unresolved issues remain with regard to the method for adjusting the optical anisotropy (see the patent document No. 6).

The present inventors found that a uniform orientation of the anisotropic polymer can be attained and the optical anisotropy can effectively be adjusted, when a polymerizable liquid crystal compound having a benzyl ester moiety in the minor axis direction of the molecule was used as a component of a polymerizable liquid crystal composition. They also found that the optical anisotropy can be decreased by a combination with a polymerizable triptycene derivative. Thus, they have completed the invention. The polymerizable liquid crystal compound having a benzyl ester moiety in the minor axis direction has at least one polymerizable group, and is polymerizable in the same manner as that of the other polymerizable liquid crystal compounds. An anisotropic polymer in which orientation is adjusted uniformly is formed, when this polymerizable liquid crystal composition is applied to a supporting substrate that has been processed with mechanical surface treatment such as rubbing, photo-alignment treatment or chemical surface treatment, and then the composition is polymerized.

SUMMARY OF THE INVENTION

The invention concerns the following polymerizable liquid crystal compound represented by formula (1), a composition including the compound, a polymer film, an anisotropic polymer, an optical compensation film, a reflection film, a liquid crystal display element and a liquid crystal display device:

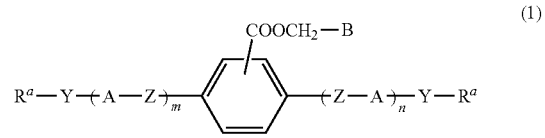

wherein at least one of $R^a$ is a polymerizable group, and $R^a$ that is not a polymerizable group is chlorine, fluorine, cyano, alkyl having 1 to 10 carbons, alkoxy having 1 to 10 carbons, —$CF_3$ or —$OCF_3$; A is independently 1,4-cyclohexylene, 1,4-cyclohexenylene, 1,3-dioxane-2,5-diyl, pyridine-2,6-diyl, pyridazine-3,6-diyl, pyrimidine-2,6-diyl, naphthalene-2,6-diyl, tetrahydronaphthalene-2,6-diyl, fluorene-2,7-diyl, bicyclo[2.2.2]octane-1,4-diyl, or 1,4-phenylene in which arbitrary hydrogen may be replaced by halogen, cyano, —$NO_2$, alkyl having 1 to 5 carbons or halogenated alkyl having 1 to 5 carbons; B is phenyl in which arbitrary hydrogen may be replaced by halogen, cyano, —$NO_2$, alkyl having 1 to 5 carbons, halogenated alkyl having 1 to 5 carbons, alkoxy having 1 to 5 carbons or halogenated alkoxy having 1 to 5 carbons; Z is independently a single bond or alkylene having 1 to 20 carbons, and in the alkylene, arbitrary —$CH_2$— may be replaced by —O—, —CO—, —COO—, —OCO—, —CH=CH—, —CF=CF— or —C≡C—, and arbitrary hydrogen may be replaced by halogen; Y is independently a single bond or alkylene having 1 to 20 carbons, and in the alkylene, arbitrary —$CH_2$— may be replaced by —O—, —CO—, —COO—, —OCO—, —OCOO— or —CH=CH—, and arbitrary hydrogen may be replaced by halogen; and m and n are each independently an integer from 0 to 5.

DETAILED DESCRIPTION OF THE INVENTION

Figure 1:
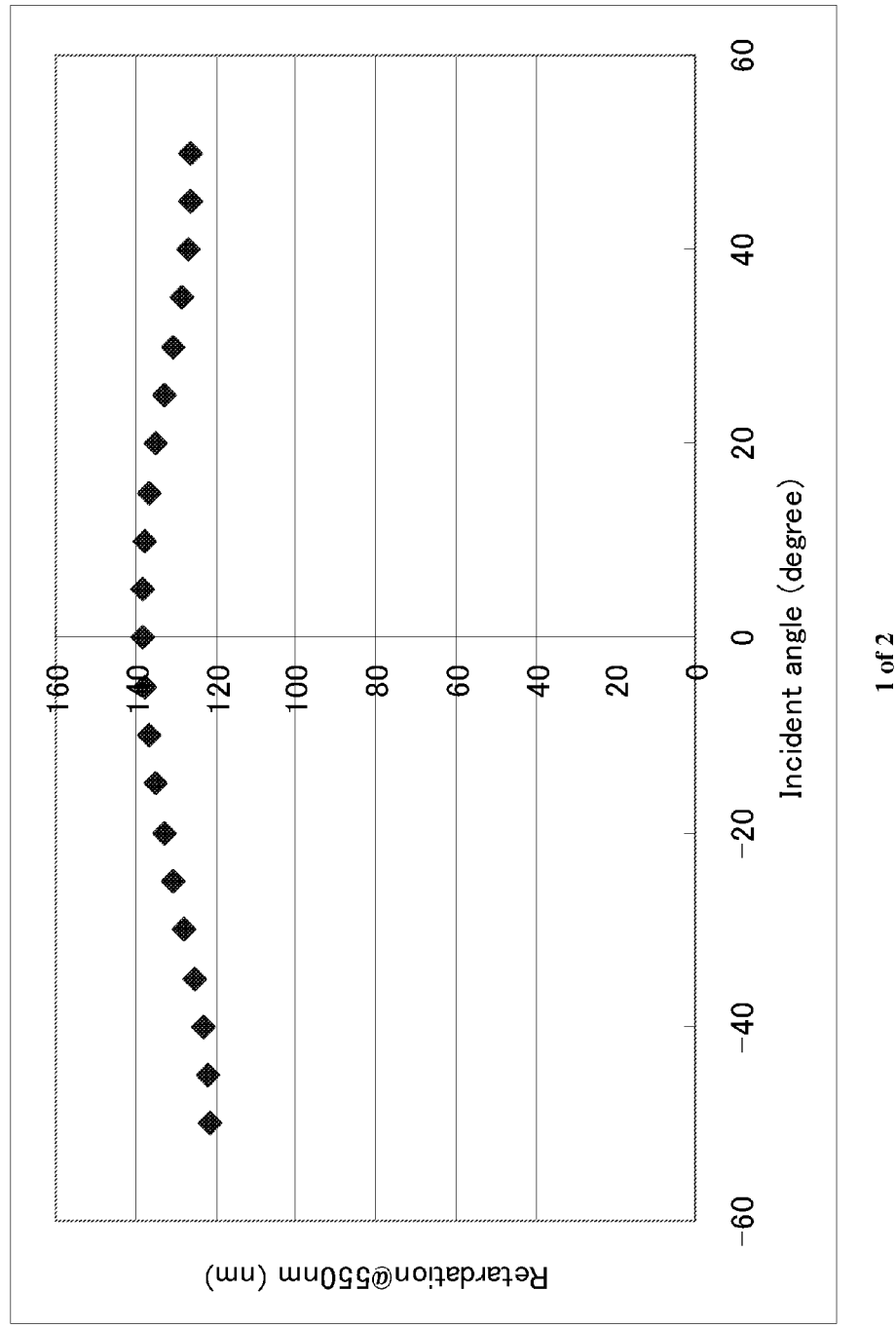
FIG. 1: Results of measurement on the retardation of the anisotropic polymer in Example 3.

One of the advantages of the invention is to provide a compound having liquid crystallinity and an excellent miscibility, and a polymerizable liquid crystal composition including this compound and having a suitable optical anisotropy, an excellent coating properties and so forth. Another advantage is to provide a polymer that is excellent in characteristics such as optical anisotropy, transparency, chemical stability, heat resistance, hardness, dimensional stability, adhesive properties, adhesion and mechanical strength, by polymerization of the polymerizable liquid crystal composition, and to provide its use utilizing the characteristics. A further advantage is to provide an optical retardation film, optical compensation film, reflection film and so forth, and also to provide an image display device containing the film, such as a liquid crystal display device, an organic EL display device and a plasma display panel.

The compound of the invention had a benzyl ester moiety in the minor axis direction of the molecule as well as a polymerizable group, and also had a liquid crystal phase and an excellent miscibility. A polymerizable liquid crystal composition of the invention, including this compound, had an easily adjustable optical anisotropy, and had a suitable optical anisotropy, excellent coating properties and so forth. An anisotropic polymer and a polymer film of the invention, which were formed by polymerization of this composition, were excellent in characteristics such as optical anisotropy, transparency, chemical stability, thermal resistance, hardness, dimensional stability, adhesive properties, adhesion and mechanical strength. Thus, the polymer of the invention was suitable for an optical use such as an optical retardation film, a polarizer, a circularly polarized light element, an elliptically polarized light element, an antireflection film, a selective reflection film, a color compensation film, a viewing angle-compensation film and a liquid crystal alignment film.

Hereinafter, the invention regarding the compound having a benzyl ester moiety in the minor axis direction of the molecule, the polymerizable liquid crystal composition including this compound, the polymer obtained from this composition and the use of the polymer will be explained in detail. Usage of the term in this specification is as follows. "A liquid crystal compound" is a generic term for a compound having a liquid crystal phase such as a nematic phase and a smectic phase, and also for a compound having no liquid crystal phases but being useful as a component of a composition. The term "the compound (1)" means one compound represented by formula (1). The term "the compound (1)" also means at least one compound represented by formula (1). The term "the composition (1)" means a composition including at least one compound selected from the compound (1). The terms "the anisotropic polymer (1) and the polymer film (1)" mean a polymer formed by polymerization of the compound (1) or the composition (1). The term "(meth)acryloyloxy" is a generic term for acryloyloxy and methacryloyloxy. The term "(meth)acrylates" is a generic term for acrylates and methacrylates. The term "(meth)acrylic acid" is a generic term for acrylic acid and methacrylic acid.

The term "arbitrary" used for the explanation of the symbols in chemical formulas means that not only the position of an element (or a group) but also its number can be selected without any restraint. For example, the expression "arbitrary Q may be replaced by R, S or T" includes cases where arbitrary Q is replaced by R, arbitrary Q is replaced by S, and arbitrary Q is replaced by T, and includes also cases where at least two Q are replaced by at least two selected from the group of a plurality of R, S and T. When arbitrary —$CH_2$— may be replaced by another group, there are no cases where a plurality of —$CH_2$— are successively replaced by a plurality of the same groups.

A substituent that is expressed as if it is not bonded definitely to any one of the carbons constituting a ring means that the substituent can be bonded to any carbon without restraint as long as the bonding position is chemically reasonable.

Although there are cases where the same symbols are used to express rings, bonding groups or terminal groups in a plurality of formulas or in one formula, the definition of these symbols is the same. These symbols may mean the same groups or different groups.

For example, groups expressed by a plurality of A may be the same or different, when the sum of m and n is two or more in formula (1). The same applies to Z. When m is an integer from 2 to 5, formula (1) contains also a plurality of A, and similarly groups represented by a plurality of A may be the same or different. The same also applies to Z. The same applies to n that is an integer from 2 to 5.

The invention includes items [1] to [33].

[1] A polymerizable liquid crystal compound represented by formula (1):

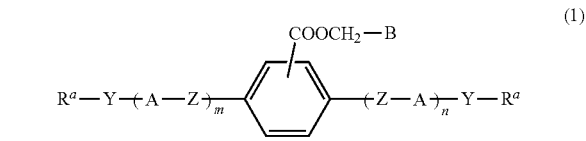

(1)

wherein at least one of $R^a$ is a polymerizable group, and $R^a$ that is not a polymerizable group is chlorine, fluorine, cyano, alkyl having 1 to 10 carbons, alkoxy having 1 to 10 carbons, —$CF_3$ or —$OCF_3$;

A is independently 1,4-cyclohexylene, 1,4-cyclohexenylene, 1,3-dioxane-2,5-diyl, pyridine-2,6-diyl, pyridazine-3,6-diyl, pyrimidine-2,6-diyl, naphthalene-2,6-diyl, tetrahydronaphthalene-2,6-diyl, fluorene-2,7-diyl, bicyclo[2.2.2]octane-1,4-diyl, or 1,4-phenylene in which arbitrary hydrogen may be replaced by halogen, cyano, —$NO_2$, alkyl having 1 to 5 carbons or halogenated alkyl having 1 to 5 carbons;

B is phenyl in which arbitrary hydrogen may be replaced by halogen, cyano, —$NO_2$, alkyl having 1 to 5 carbons, halogenated alkyl having 1 to 5 carbons, alkoxy having 1 to 5 carbons or halogenated alkoxy having 1 to 5 carbons;

Z is independently a single bond or alkylene having 1 to 20 carbons, and in the alkylene, arbitrary —$CH_2$— may be replaced by —O—, —CO—, —COO—, —OCO—, —CH=CH—, —CF=CF— or —C≡C—, and arbitrary hydrogen may be replaced by halogen;

Y is independently a single bond or alkylene having 1 to 20 carbons, and in the alkylene, arbitrary —$CH_2$— may be replaced by —O—, —CO—, —COO—, —OCO—, —OCOO— or —CH=CH—, and arbitrary hydrogen may be replaced by halogen; and m and n are each independently an integer from 0 to 5.

[2] The polymerizable liquid crystal compound according to item [1], wherein the polymerizable group is a substituent selected from the group of substituents represented by formulas (a-1) to (a-9):

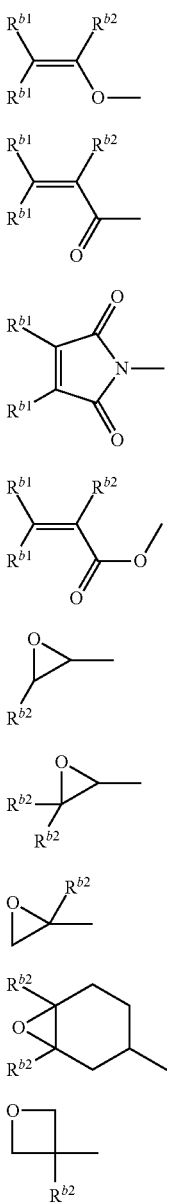

wherein $R^{b1}$ and $R^{b2}$ are each independently hydrogen, halogen, alkyl having 1 to 5 carbons or halogenated alkyl having 1 to 5 carbons.

[3] The polymerizable liquid crystal compound according to item [1], wherein the polymerizable group is a substituent represented by formula (a-4):

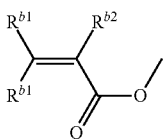

wherein $R^{b1}$ and $R^{b2}$ are each independently hydrogen, halogen, alkyl having 1 to 5 carbons or halogenated alkyl having 1 to 5 carbons.

[4] The polymerizable liquid crystal compound according to any one of items [1] to [3], wherein in formula (1), the sum of m and n is an integer from 1 to 3.

[5] The polymerizable liquid crystal compound according to any one of items [1] to [3], wherein in formula (1), the sum of m and n is 2.

[6] The polymerizable liquid crystal compound according to any one of items [1] to [5], wherein in formula (1), A is independently 1,4-cyclohexylene, pyridine-2,5-diyl, pyridazine-3,6-diyl, pyrimidine-2,5-diyl, or 1,4-phenylene in which arbitrary hydrogen may be replaced by chlorine, fluorine, cyano, alkyl having 1 to 3 carbons or fluoroalkyl having 1 to 3 carbons; and B is phenyl in which arbitrary hydrogen may be replaced by fluorine, cyano, —$NO_2$, alkyl having 1 to 3 carbons, fluoroalkyl having 1 to 3 carbons, alkoxy having 1 to 3 carbons or fluoroalkoxy having 1 to 3 carbons.

[7] The polymerizable liquid crystal compound according to item [6], wherein in formula (1), A is independently 1,4-cyclohexylene, or 1,4-phenylene in which arbitrary hydrogen may be replaced by chlorine, fluorine, cyano, —$CH_3$ or —$CF_3$; and B is phenyl in which arbitrary hydrogen may be replaced by fluorine, cyano, —$NO_2$ or —$OCF_3$.

[8] The polymerizable liquid crystal compound according to any one of items [1] to [7], wherein in formula (1), Z is independently a single bond, —$CH_2O$—, —$OCH_2$—, —COO—, —OCO—, —CH=CH—, —$(CH_2)_2COO$—, —$OCO(CH_2)_2$—, —CH=CHCOO—, —OCOCH=CH— or —C≡C—.

[9] The polymerizable liquid crystal compound according to any one of items [1] to [7], wherein in formula (1), Z is independently a single bond, —$CH_2O$—, —$OCH_2$—, —COO— or —OCO—.

[10] The polymerizable liquid crystal compound according to any one of items [1] to [9], wherein in formula (1), Y is independently alkylene having 1 to 12 carbons, and in the alkylene, arbitrary —$CH_2$— may be replaced by —O—, —COO—, —OCO— or —OCOO—.

[11] A polymerizable liquid crystal composition, including at least one of compounds according to any one of items [1] to [10].

[12] A polymerizable liquid crystal composition, including at least one of polymerizable liquid crystal compounds represented by formula (1) and at least one polymerizable liquid crystal compound selected from the group of compounds represented by formula (M1), formula (M2-1) to formula (M2-5), formula (M3) and formula (M4):

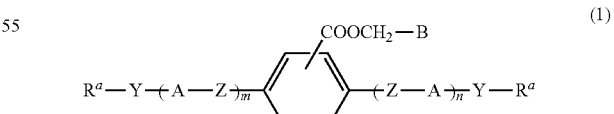

wherein at least one of $R^a$ is a polymerizable group and is a substituent selected from the group of substituents represented by formula (a-1) to formula (a-9), and $R^a$ that is not a polymerizable group is chlorine, fluorine, cyano, alkyl having 1 to 10 carbons, alkoxy having 1 to 10 carbons, —$CF_3$ or —$OCF_3$;

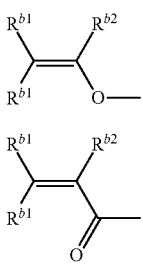

(a-1)

(a-2)

(a-3)

(a-4)

(a-5)

(a-6)

(a-7)

(a-8)

(a-9)

in formula (a-1) to formula (a-9), $R^{b1}$ and $R^{b2}$ are each independently hydrogen, halogen, alkyl having 1 to 5 carbons or halogenated alkyl having 1 to 5 carbons;

A is independently 1,4-cyclohexylene, 1,4-cyclohexenylene, 1,3-dioxane-2,5-diyl, pyridine-2,6-diyl, pyridazine-3,6-diyl, pyrimidine-2,6-diyl, naphthalene-2,6-diyl, tetrahydronaphthalene-2,6-diyl, fluorene-2,7-diyl, bicyclo[2.2.2]octane-1,4-diyl, or 1,4-phenylene in which arbitrary hydrogen may be replaced by halogen, cyano, —NO$_2$, alkyl having 1 to 5 carbons or halogenated alkyl having 1 to 5 carbons;

B is phenyl in which arbitrary hydrogen may be replaced by halogen, cyano, —NO$_2$, alkyl having 1 to 5 carbons, halogenated alkyl having 1 to 5 carbons, alkoxy having 1 to 5 carbons or halogenated alkoxy having 1 to 5 carbons;

Z is independently a single bond or alkylene having 1 to 20 carbons, and in the alkylene, arbitrary —CH$_2$— may be replaced by —O—, —CO—, —COO—, —OCO—, —CH=CH—, —CF=CF— or —C≡C—, and arbitrary hydrogen may be replaced by halogen;

Y is independently a single bond or alkylene having 1 to 20 carbons, and in the alkylene, arbitrary —CH$_2$— may be replaced by —O—, —CO—, —COO—, —OCO—, —OCOO— or —CH=CH—, and arbitrary hydrogen may be replaced by halogen; and m and n are each independently an integer from 0 to 5; and (M1)

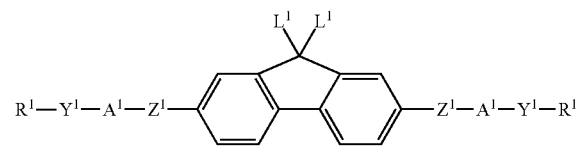

(M2-1)

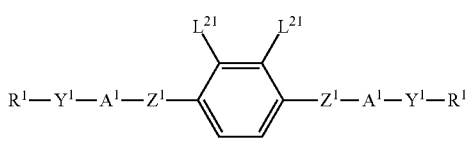

(M2-2)

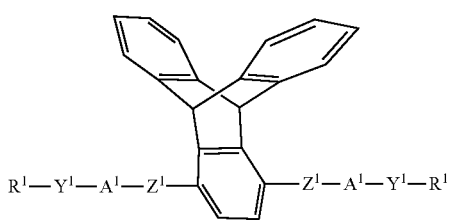

(M2-3)

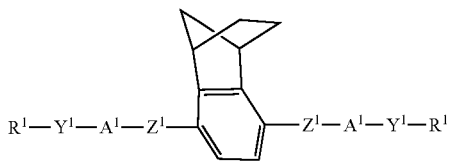

(M2-4)

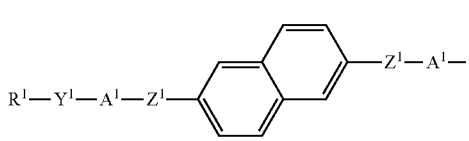

(M2-5)

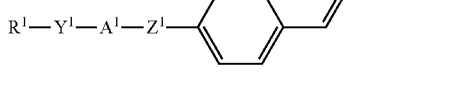

(M3)

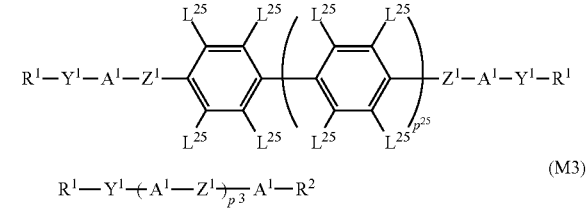

(M4)

wherein $R^1$ is independently a substituent represented by formula (a-4), formula (a-5) or formula (a-9) described above;

$R^2$ is alkyl having 1 to 10 carbons, alkoxy having 1 to 10 carbons, chlorine, fluorine, cyano, —CF$_3$ or —OCF$_3$;

$A^1$ is independently 1,4-cyclohexylene, or 1,4-phenylene in which arbitrary hydrogen may be replaced by fluorine;

$Z^1$ is independently a single bond, —CH$_2$CH$_2$—, —CH$_2$O—, —OCH$_2$—, —COO, —OCO—, —CH═CH—, —C≡C—, —CH═CHCOO—, —OCOCH═CH—, —(CH$_2$)$_2$COO— or —OCO(CH$_2$)$_2$—;

$Y^1$ is independently a single bond or alkylene having 1 to 20 carbons, and in the alkylene, arbitrary —CH$_2$— may be replaced by —O—, —CO—, —COO—, —OCO—, —OCOO— or —CH═CH—;

$L^1$ is independently hydrogen, fluorine or —CH$_3$;

$L^{21}$ is independently hydrogen, halogen, cyano, alkyl having 1 to 8 carbons or halogenated alkyl having 1 to 8 carbons;

$L^{25}$ is independently hydrogen, halogen, alkyl having 1 to 8 carbons, alkoxy having 1 to 8 carbons, cyano or halogenated alkyl having 1 to 8 carbons;

$p^{25}$ is 1 or 2; and $p^3$ is 1 or 2.

[13] The polymerizable liquid crystal composition according to item [12], wherein in formula (1), a polymerizable group is a substituent represented by formula (a-4), formula (a-5) or formula (a-9); A is independently 1,4-cyclohexylene, pyridine-2,5-diyl, pyridazine-3,6-diyl, pyrimidine-2,5-diyl, or 1,4-phenylene in which arbitrary hydrogen may be replaced by chlorine, fluorine, cyano, alkyl having 1 to 3 carbons or fluoroalkyl having 1 to 3 carbons; B is phenyl in which arbitrary hydrogen may be replaced by fluorine, cyano, —NO$_2$, alkyl having 1 to 3 carbons, fluoroalkyl having 1 to 3 carbons, alkoxy having 1 to 3 carbons or fluoroalkoxy having 1 to 3 carbons; Z is independently a single bond, —CH$_2$O—, —OCH$_2$—, —COO—, —OCO—, —CH═CH—, —(CH$_2$)$_2$COO—, —OCO(CH$_2$)$_2$—, —CH═CHCOO—, —OCOCH═CH— or —C≡C—; Y is independently a single bond or alkylene having 1 to 10 carbons, and in the alkylene, arbitrary —CH$_2$— may be replaced by —O—, —COO—, —OCO— or —OCOO—; and m and n is 1;

and in formula (M1), formula (M2-1) to formula (M2-5), formula (M3) and formula (M4), $R^1$ is independently a substituent represented by formula (a-4), formula (a-5) or formula (a-9); $R^2$ is alkyl having 1 to 8 carbons, alkoxy having 1 to 8 carbons, chlorine, fluorine, cyano, —CF$_3$ or —OCF$_3$; $A^1$ is independently 1,4-cyclohexylene, 1,4-phenylene, monofluoro-1,4-phenylene or difluoro-1,4-phenylene; $Z^1$ is independently a single bond, —CH$_2$O—, —OCH$_2$—, —COO—, —OCO—, —C≡C—, —CH═CHCOO—, —OCOCH═CH—, —(CH$_2$)$_2$COO— or —OCO(CH$_2$)$_2$—; $Y^1$ is independently a single bond or alkylene having 1 to 12 carbons, and in the alkylene, arbitrary —CH$_2$— may be replaced by —O—, —COO—, —OCO— or —OCOO—; $L^1$ is independently hydrogen, fluorine or —CH$_3$; $L^{21}$ is independently hydrogen, halogen, cyano, alkyl having 1 to 5 carbons or halogenated alkyl having 1 to 5 carbons; $L^{25}$ is independently hydrogen, halogen, cyano, alkyl having 1 to 5 carbons, alkoxy having 1 to 5 carbons or halogenated alkyl having 1 to 5 carbons; $p^{25}$ is 1 or 2; and $p^3$ is 1 or 2;

and the ratio of a polymerizable liquid crystal compound represented by formula (1) is in the range of approximately 3% to approximately 90% by weight and the ratio of a polymerizable compound selected from the group of compounds represented by formula (M1), formula (M2-1), formula (M2-2) to formula (M2-5), formula (M3) and formula (M4) is in the range of approximately 10% to approximately 97% by weight, based on the total weight of the polymerizable liquid crystal compound represented by formula (1) and the polymerizable compound selected from the group of compounds represented by formula (M1), formula (M2-1) to formula (M2-5), formula (M3) and formula (M4).

[14] The polymerizable liquid crystal composition according to item [12], wherein in formula (1), a polymerizable group is independently a substituent represented by formula (a-4), formula (a-5) or formula (a-9); A is independently 1,4-cyclohexylene, or 1,4-phenylene in which arbitrary hydrogen may be replaced by chlorine, fluorine, —CH$_3$ or —CF$_3$; B is phenyl in which arbitrary hydrogen may be replaced by fluorine, cyano, —NO$_2$ or —OCF$_3$; Z is independently a single bond, —COO— or —OCO—; Y is independently alkylene having 1 to 10 carbons, and in the alkylene, —CH$_2$— bonded to the ring A may be replaced by —O—, —COO—, —OCO— or —OCOO—; and m and n is 1;

and in formula (M1), formula (M2-1) to formula (M2-5), formula (M3) and formula (M4), $R^1$ is independently a substituent represented by formula (a-4), formula (a-5) or formula (a-9); $R^2$ is alkyl having 1 to 8 carbons, alkoxy having 1 to 8 carbons, cyano, fluorine or —OCF$_3$; $A^1$ is independently 1,4-cyclohexylene, 1,4-phenylene, monofluoro-1,4-phenylene or difluoro-1,4-phenylene; $Z^1$ is independently a single bond, —COO—, —OCO—, —CH═CHCOO—, —OCOCH═CH—, —(CH$_2$)$_2$COO— or —OCO(CH$_2$)$_2$—; $Y^1$ is independently a single bond or alkylene having 1 to 10 carbons, and in the alkylene, —CH$_2$— that is bonded to the ring $A^1$ may be replaced by —O—, —COO—, —OCO— or —OCOO—; $L^1$ is independently hydrogen or —CH$_3$; $L^{21}$ is independently hydrogen, fluorine, methyl, cyano, isopropyl, tert-butyl or trifluoromethyl; $L^{25}$ is independently hydrogen, fluorine, methyl, or methoxy; $p^{25}$ is 1 or 2; and $p^3$ is 2;

and the ratio of a polymerizable liquid crystal compound represented by formula (1) is in the range of approximately 15% to approximately 80% by weight, and the ratio of a polymerizable liquid crystal compound selected from the group of compounds represented by formula (M1), formula (M2-1) to formula (M2-5), formula (M3) and formula (M4) is in the range of approximately 20% to approximately 85% by weight, based on the total weight of the polymerizable liquid crystal compound represented by formula (1), and the polymerizable compound selected from the group of compounds represented by formula (M1), formula (M2-1) to formula (M2-5), formula (M3) and formula (M4).

[15] The polymerizable liquid crystal composition according to any one of items [12] to [14], further including a polymerizable compound that is not optically active and is different from compounds represented by formula (1), formula (M1), formula (M2-1) to formula (M2-5), formula (M3) and formula (M4).

[16] The polymerizable liquid crystal composition according to any one of items [12] to [15], further including a polymerizable and optically active compound.

[17] The polymerizable liquid crystal composition according to any one of items [12] to [16], further including a non-polymerizable liquid crystal compound.

[18] The polymerizable liquid crystal composition according to any one of items [12] to [17], further including a non-polymerizable and optically active compound.

[19] A polymer film formed by polymerization of the polymerizable liquid crystal compound according to any one of items [12] to [18].

[20] An anisotropic polymer formed by polymerization of the polymerizable liquid crystal compound according to any one of items [12] to [18].

[21] The anisotropic polymer according to item [20], wherein the orientational mode of the polymerizable liquid crystal composition is any one of a homogeneous orientation, a tilted orientation, a twisted orientation and a homeotropic orientation.

[22] The anisotropic polymer according to item [20] or [21], wherein the orientational mode of the polymerizable liquid crystal composition is adjusted by any one of rubbing treatment, photo-alignment treatment, ion beam treatment, corona treatment and plasma treatment.

[23] The anisotropic polymer according to item [20] or [21], wherein the orientational mode of the polymerizable liquid crystal composition is adjusted by any one of rubbing treatment, photo-alignment treatment, corona treatment and plasma treatment.

[24] The anisotropic polymer according to any one of items [20] to [23], wherein the anisotropic polymer is formed on a glass substrate.

[25] The anisotropic polymer according to any one of items [20] to [23], wherein the anisotropic polymer is formed on a glass substrate that has been coated with a plastic thin film, or formed on a plastic substrate composed of a plastic film.

[26] The anisotropic polymer according to item [25], wherein plastic that is a material of the plastic thin film and the plastic film is selected from polyimides, polyamideimides, polyamides, polyetherimides, polyetheretherketones, polyetherketones, polyketonesulfides, polyethersulfones, polysulfones, polyphenylenesulfides, polyphenyleneoxides, polyethylenes terephthalates, polybutylene terephthalates, polyethylene naphthalates, polyacetals, polycarbonates, polyacrylates, acrylic resins, polyvinyl alcohols, polypropylenes, celluloses, triacetyl celluloses, partially saponified products of triacetylcelluloses, epoxy resins, phenol resins and cycloolefin-based resins.

[27] The anisotropic polymer according to item [25], wherein plastic that is a material of the plastic thin film and the plastic film is selected from polyimides, polyvinyl alcohols, triacetyl celluloses, partially saponified products of triacetylcelluloses and cycloolefin-based resins.

[28] An optical compensation film having the anisotropic polymer according to any one of items [20] to [27].

[29] A reflection film having the anisotropic polymer according to any one of items [20] to [27].

[30] A liquid crystal display element containing the optical compensation film according to item [28].

[31] A liquid crystal display element containing the reflection film according to item [29].

[32] A liquid crystal display device containing the optical compensation film according to item [28].

[33] A liquid crystal display device containing the reflection film according to item [29].

Compounds

The compound of the invention is represented by formula (1).

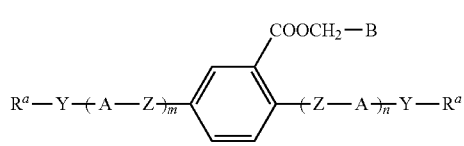

(1)

In formula (1), at least one of $R^a$ is a polymerizable group. Formula (1) is developed into the following two formulas.

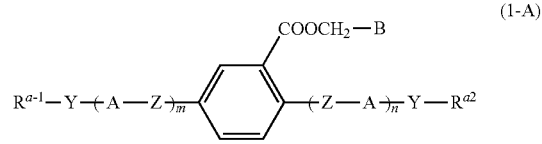

(1-A)

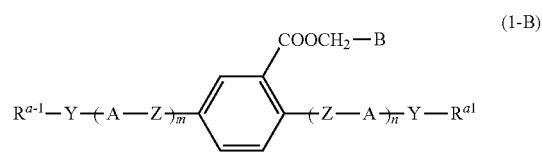

(1-B)

In formula (1-A) and formula (1-B), $R^{a1}$ is a polymerizable group. It is desirable that $R^{a1}$ is a substituent selected from the group of substituents represented by the following formula (a-1) to formula (a-9). At this point, two $R^{a1}$ in formula (1-B) may be the same substituents or different substituents. It is desirable that two $R^{a1}$ are the same substituents.

(a-1)

(a-2)

(a-3)

(a-4)

(a-5)

(a-6)

(a-7)

(a-8)

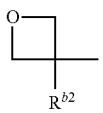
(a-9)

In these formulas, $R^{b1}$ and $R^{b2}$ are each independently hydrogen, halogen, alkyl having 1 to 5 carbons or halogenated alkyl having 1 to 5 carbons. Desirable examples of $R^{b1}$ and $R^{b2}$ are hydrogen, fluorine, chlorine, —$CH_3$ and —$CF_3$. An especially desirable example of $R^{b1}$ is hydrogen. An especially desirable example of $R^{a1}$ is a substituent represented by formula (a-4).

In formula (1-A), $R^{a2}$ is chlorine, fluorine, cyano, alkyl having 1 to 10 carbons, alkoxy having 1 to 10 carbons, —$CF_3$ or —$OCF_3$.

In formula (1-A) and formula (1-B), A is independently 1,4-cyclohexylene, 1,4-cyclohexenylene, 1,3-dioxane-2,5-diyl, pyridine-2,6-diyl, pyridazine-3,6-diyl, pyrimidine-2,6-diyl, naphthalene-2,6-diyl, tetrahydronaphthalene-2,6-diyl, fluorene-2,7-diyl, bicyclo[2.2.2]octane-1,4-diyl, or 1,4-phenylene in which arbitrary hydrogen may be replaced by halogen, cyano, alkyl having 1 to 5 carbons or halogenated alkyl having 1 to 5 carbons.

Desirable examples of A are 1,4-cyclohexylene, pyridine-2,5-diyl, pyridazine-3,6-diyl, pyrimidine-2,5-diyl, or 1,4-phenylene in which arbitrary hydrogen may be replaced by chlorine, fluorine, cyano, alkyl having 1 to 3 carbons or fluoroalkyl having 1 to 3 carbons. More desirable examples of A are 1,4-cyclohexylene, or 1,4-phenylene in which arbitrary hydrogen may be replaced by chlorine, fluorine, cyano, —$CH_3$ or —$CF_3$.

In formula (1-A) and formula (1-B), B is phenyl in which arbitrary hydrogen may be replaced by halogen, cyano, —$NO_2$, alkyl having 1 to 5 carbons, halogenated alkyl having 1 to 5 carbons, alkoxy having 1 to 5 carbons or halogenated alkoxy having 1 to 5 carbons. Desirable examples of B are phenyl in which arbitrary hydrogen may be replaced by fluorine, cyano, —$NO_2$, alkyl having 1 to 3 carbons, fluoroalkyl having 1 to 3 carbons, alkoxy having 1 to 3 carbons or fluoroalkoxy having 1 to 3 carbons. More desirable examples of B are phenyl in which arbitrary hydrogen may be replaced by fluorine, cyano, —$NO_2$ or fluoroalkoxy having 1 to 3 carbons. An especially desirable example of the fluoroalkoxy having 1 to 3 carbons is —$OCF_3$.

In formula (1-A) and formula (1-B), Z is independently a single bond or alkylene having 1 to 20 carbons. In the alkylene, arbitrary —$CH_2$— may be replaced by —O—, —CO—, —COO—, —OCO—, —CH═CH—, —CF═CF— or —C≡C—, and arbitrary hydrogen may be replaced by halogen. Desirable examples of Z are a single bond, —$CH_2O$—, —$OCH_2$—, —COO—, —OCO—, —CH═CH—, —$(CH_2)_2$COO—, —$OCO(CH_2)_2$—, —CH═CH—COO—, —OCO—CH═CH— and —C≡C—, and more desirable examples are a single bond, —$CH_2O$—, —$OCH_2$—, —COO— and —OCO—.

In formula (1-A) and formula (1-B), Y is independently a single bond or alkylene having 1 to 20 carbons. In the alkylene, arbitrary —$CH_2$— may be replaced by —O—, —CO—, —COO—, —OCO—, —OCOO— or —CH═CH—, and arbitrary hydrogen may be replaced by halogen. A desirable example of Y is alkylene having 1 to 12 carbons, and in the alkylene, arbitrary —$CH_2$— may be replaced by —O—, —COO—, —OCO— or —OCOO—.

In formula (1-A) and formula (1-B), m and n, are each independently an integer from 0 to 5. With regard to m and n, it is desirable that the sum of m and n is an integer from 1 to 3. It is more desirable that the sum of m and n is 2. It is most desirable that both m and n are 1.

The compound (1) of the invention has a high polymerization reactivity. The compound (1) has a large internal free volume, which causes the effect of a decrease in the optical anisotropy, because of the presence of a benzyl ester moiety in the minor axis direction of the molecule. The compound (1) easily maintains a liquid crystal phase, and is easily mixed with another liquid crystal compound, another polymerizable compound or the like, giving a homogeneous mixture. Incidentally, the compound (1) could be optically active, if it has an asymmetric carbon.

Physical properties such as optical anisotropy can optionally be adjusted by a suitable selection of the terminal groups, the rings and the bonding groups of the compound (1). The effects of the kinds of the terminal groups $R^a$, the ring A and the bonding group Z on characteristics of the compound (1) will be explained below.

When the terminal group $R^a$ is chlorine, fluorine, cyano, alkyl having 1 to 10 carbons, alkoxy having 1 to 10 carbons, —$CF_3$ or —$OCF_3$, it seems that $R^a$ influences characteristics such as the melting point, the solubility in solvent and the compatibility with another compound. When the terminal group $R^a$ is alkyl having 1 to 10 carbons or alkoxy having 1 to 10 carbons, it seems that $R^a$ influences the melting point and the solubility. When the terminal group $R^a$ is chlorine, fluorine, cyano, —$CF_3$ or —$OCF_3$, it seems that $R^a$ influences characteristics such as the melting point, the solubility in solvent and the compatibility with another compound.

When the ring A is 1,4-phenylene, 1,4-phenylene in which arbitrary hydrogen is replaced by fluorine, pyridine-2,5-diyl, pyrimidine-2,5-diyl or pyridazine-3,6-diyl, the optical anisotropy is large. When A is 1,4-cyclohexylene, 1,4-cyclohexenylene or 1,3-dioxane-2,5-diyl, the optical anisotropy is small. When, in a plurality of the ring A, at least two of the ring A are 1,4-cyclohexylene, the clearing point is high, the optical anisotropy is small, and the viscosity is small. When at least one of the ring A is 1,4-phenylene, the optical anisotropy is relatively large, and the orientational order parameter is large. When at least two of the ring A are 1,4-phenylene, the optical anisotropy is large, the temperature range of a liquid crystal phase is wide, and the clearing point is high.

When the terminal group B is phenyl in which arbitrary hydrogen is replaced by halogen, cyano, —$NO_2$, alkyl having 1 to 5 carbons, halogenated alkyl having 1 to 5 carbons, alkoxy having 1 to 5 carbons or halogenated alkoxy having 1 to 5 carbons, it seems that B influences characteristics such as the melting point, the solubility in solvent and the compatibility with another compound.

When the bonding group Z is a single bond, —$(CH_2)_2$—, —$CH_2O$—, —$OCH_2$—, —$CF_2O$—, —$OCF_2$—, —CH═CH—, —CF═CF— or —$(CH_2)_4$—, the viscosity is small. When the bonding group Z is a single bond, —$(CH_2)_2$—, —$OCF_2$—, —$CF_2O$—, —CH═CH— or —$(CH_2)_4$—, the viscosity is smaller. When the bonding group Z is —CH═CH— or —CF═CF—, the temperature range of a liquid crystal phase is wide. When the bonding group Z is —C≡C—, the optical anisotropy is large.

When the compound (1) has three or less of the ring A, the viscosity is small, and when it has three or more of the ring A, the clearing point is high. The compound (1) may be optically active or optically non-active. When the compound (1) is optically active, the configuration of asymmetric carbon may be R or S. When the compound (1) has asymmetric carbon, it has an excellent compatibility.

As described above, a compound having objective physical properties can be obtained by a suitable selection of the kinds of the substituents, the rings and the bonding groups, and of the number of the rings.

The compound (1) can be prepared by means of a combination of techniques in synthetic organic chemistry. Methods for an introduction of objective substituents, rings and bonding groups to starting materials are described in books such as Houben-Wyle, Methods of Organic Chemistry, Georg Thieme Verlag, Stuttgart; Organic syntheses, John Wily & Sons, Inc.; Organic Reactions, John Wily & Sons Inc.; Comprehensive Organic Synthesis, Pergamon Press; and New Experimental Chemistry Course (Shin Jikken Kagaku Kouza, in Japanese title), Maruzen Co., LTD.

Formation of the bonding group Z will be explained in Schemes 1 to 12. In these schemes, $MSG^1$ and $MSG^2$ are a monovalent organic group having at least one ring. A plurality of $MSG^1$ (or $MSG^2$) may be the same organic groups or different organic groups. The compounds (1A) to (1M) correspond to the compound (1) of the invention. These methods can be applied to the preparation of the optically active compound (1) and also to the optically non-active compound (1). These methods can also be applied to the formation of the bonding group Y.

Scheme 1: Compounds where Z is a Single Bond

The compound (1A) is prepared by the reaction of the arylboronic acid (S1) with the compound (S2) that is prepared by a known method, in an aqueous solution of a carbonate in the presence of catalyst such as tetrakis(triphenylphosphine)palladium. The compound (1A) can also be prepared by the reaction of the compound (S3) that is prepared by a known method, with n-butyllithium, and then with zinc chloride, and then by the reaction of the resulting intermediate with the compound (S2) in the presence of a catalyst such as dichlorobis(triphenylphosphine)palladium.

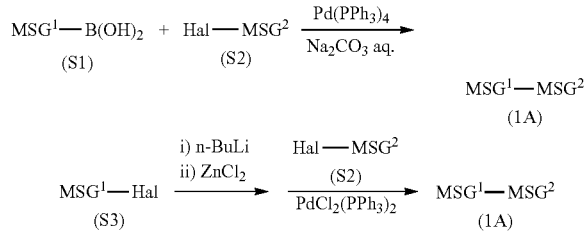

Scheme 2: Compounds where Z is —CH=CH—

A phosphine ylide is generated by the addition of a base such as potassium t-butoxide to the phosphonium salt (S5) that is prepared by a known method. The compound (1B) is prepared by the reaction of the aldehyde (S4) with the phosphine ylide. Since a cis-isomer may be formed depending on the reaction conditions and the kinds of a substrate, the cis-isomer is isomerized to the corresponding trans-isomer by a known method as requested.

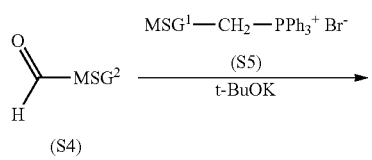

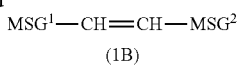

Scheme 3: Compounds where Z is —(CH$_2$)$_2$—

The compound (1C) is prepared by hydrogenation of the compound (1B) in the presence of a catalyst such as palladium on carbon.

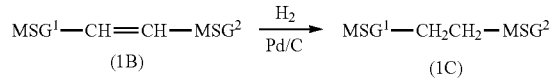

Scheme 4: Compounds where Group Z is —(CF$_2$)$_2$—

The compound (1D) having —(CF$_2$)$_2$— is prepared by fluorination of the diketone (S6) with sulfur tetrafluoride in the presence of a hydrogen fluoride-catalyst, according to the method described in J. Am. Chem. Soc., 2001, 123, 5414.

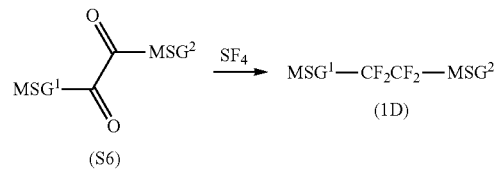

Scheme 5: Compounds where Group Z is —(CH$_2$)$_4$—

The compound (1E) is prepared by catalytic hydrogenation of the compound having —(CH$_2$)$_2$—CH=CH—, which is prepared by use of the phosphonium salt (S7) instead of the phosphonium salt (S5) according to the method in Scheme 2.

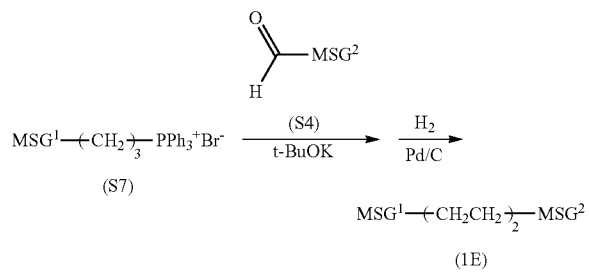

Scheme 6: Compounds where Z is —CH$_2$O— or —OCH$_2$—

The compound (S4) is reduced with a reducing agent such as sodium borohydride, giving the compound (S8). Then, the compound (S8) is halogenated with hydrobromic acid or the like, giving the compound (S9). The compound (1F) is prepared by the reaction of the compound (S9) with the compound (S10) in the presence of potassium carbonate or the like. The compound having —CH$_2$O— can also be prepared in the same manner.

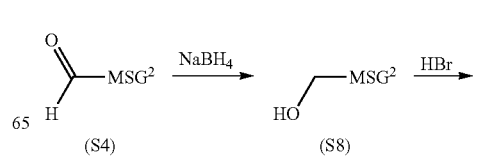

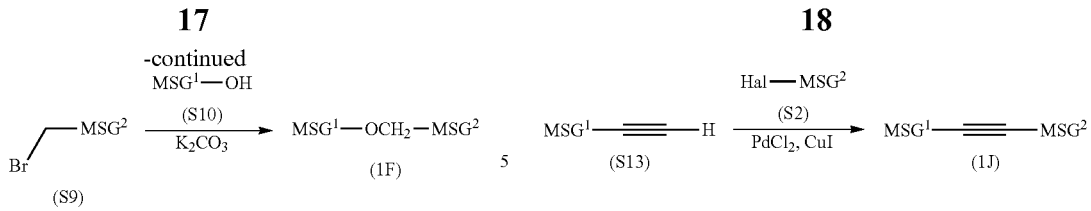

Scheme 7: Compounds where Z is —COO— or —OCO—

The compound (S3) is allowed to react with n-butyllithium and then with carbon dioxide, giving the carboxylic acid (S11). The compound (1G) having —COO— is prepared by the dehydration of the compound (S11) and phenol (S10) in the presence of DCC (1,3-dicyclohexylcarbodiimide) and DMAP (4-dimethylaminopyridine). The compound having —OCO— can also be prepared in the same manner. The compound (1G) can also be prepared by the reaction of thionyl chloride or oxalyl chloride with the compound (S11), giving the corresponding acid chloride, and then by the reaction of the compound (S10) with the acid chloride in the presence of a base such as pyridine or triethylamine.

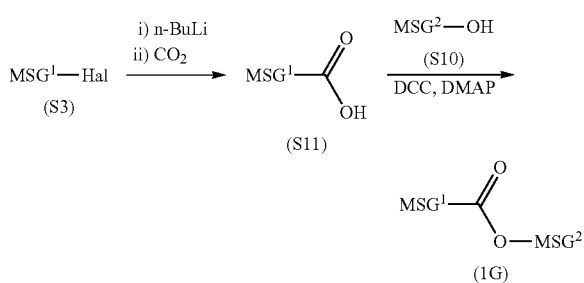

Scheme 8: Compounds where Z is —CF=CF—

The compound (S3) is treated with n-butyllithium, and then allowed to react with tetrafluoroethylene, giving the compound (S12). The compound (1H) is prepared by the treatment of the compound (S2) with n-butyllithium, and then by the reaction with the compound (S12). A cis-isomer of the compound (1H) can also be produced by selecting the reaction conditions.

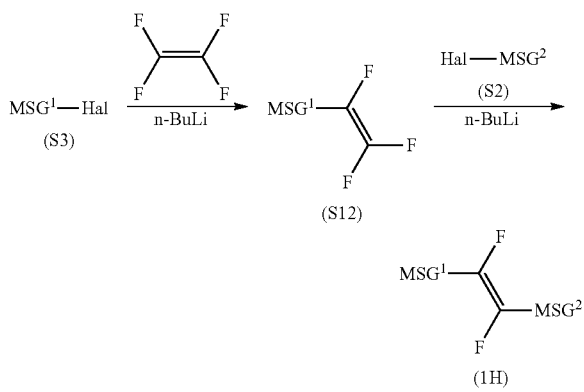

Scheme 9: Compounds where Z is —C≡C—

The compound (1J) is prepared by the reaction of the compound (S13) with the compound (S2) in the presence of a catalyst of dichloropalladium and a copper halide.

Scheme 10: Compound where Z is —C≡C—COO—

The compound (S13) is lithiated with n-butyllithium, and then allowed to react with carbon dioxide, giving the carboxylic acid (S14). The compound (1K) having —C≡C—COO— is prepared by the dehydration of the carboxylic acid (S14) and the phenol (S10) in the presence of DCC and DMAP. The compound having —OCO—C≡C— can also be prepared in the same manner. The compound (1K) can also be prepared via an acid chloride in the same way as described in the derivation of the compound (1G) from the compound (S11) in Scheme 7.

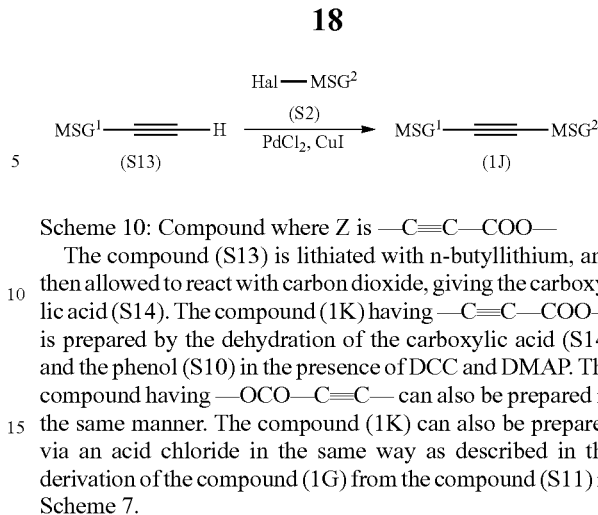

Scheme 11: Compound where Z is —C≡C—CH=CH— or —CH=CH—C≡C—

The compound (1L) having —C≡C—CH=CH— is prepared by the cross-coupling reaction of the compound (S13) with vinyl bromide (S15). The cis isomer of the compound (1L) can be prepared when the cis isomer of the compound (S15) is used.

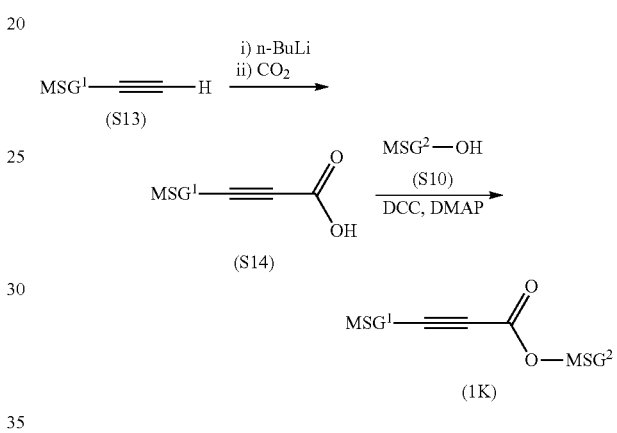

Scheme 12: Compound where Z is —CF$_2$O— or —OCF$_2$—

The compound (1G) is treated with a thionating agent such as Lawesson's reagent, giving the compound (S16). The compound (1M) having —CF$_2$O— is prepared by fluorination of the compound (S16) with a hydrogen fluoride-pyridine complex and NBS (N-bromosuccinimide). The compound (1M) can also be prepared by fluorination of the compound (S16) with (diethylamino) sulfur trifluoride (DAST). The compound having —OCF$_2$— can also be prepared in the same manner. These bonding groups can also be formed by the method described in P. Kirsch et al., Angew. Chem. Int. Ed. 2001, 40, 1480.

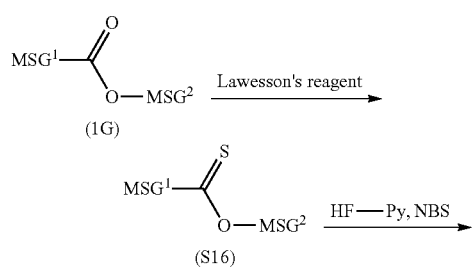
(1G)
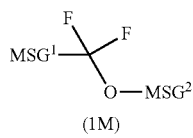
(1M)
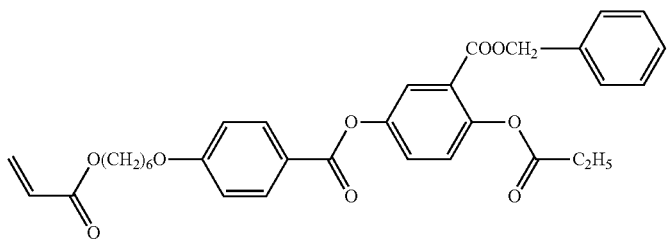
(S16)
Examples of the compounds prepared by the method described above are as follows. Incidentally, the structures of compounds prepared in the manner described above can be confirmed by means, for example, of proton NMR spectra.
1-A-1
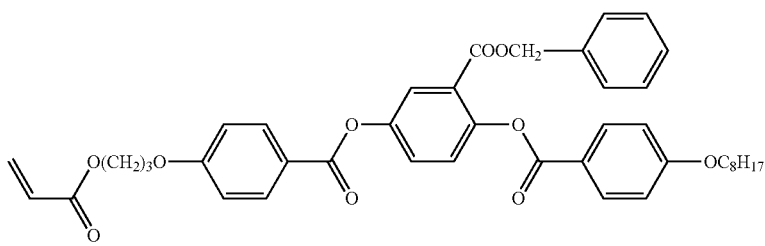
1-A-2
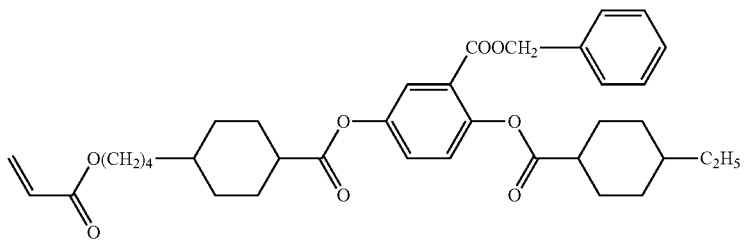
1-A-3
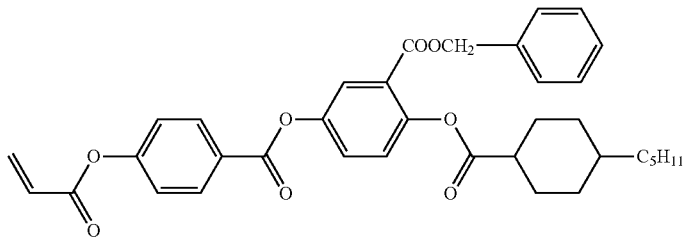
1-A-4
1-A-5
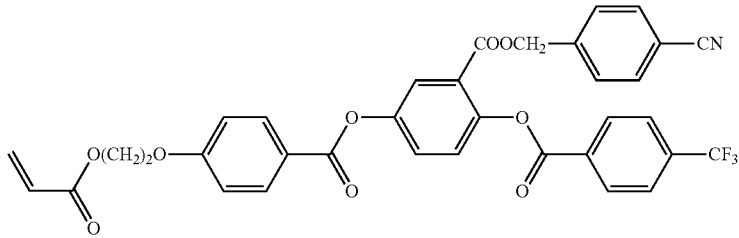

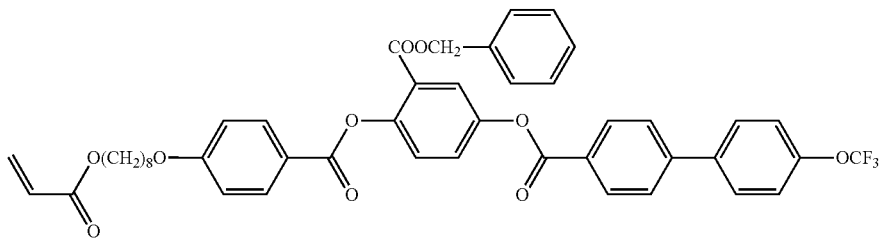
1-A-6
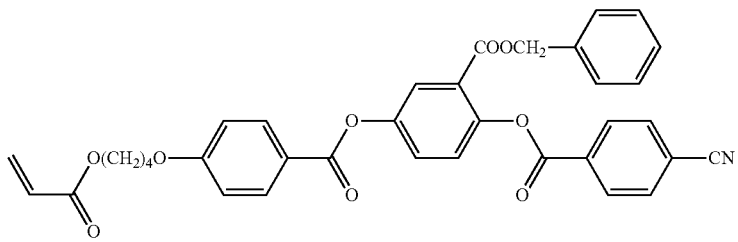
1-A-7
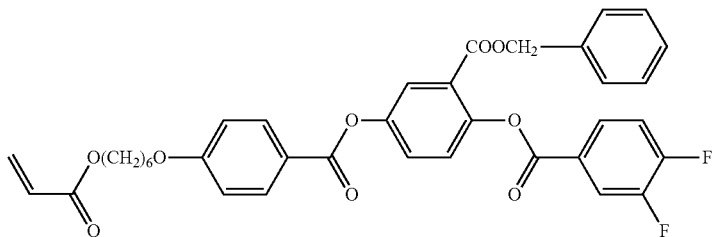
1-A-8
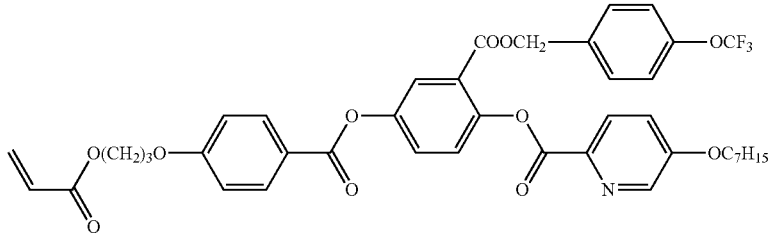
1-A-9
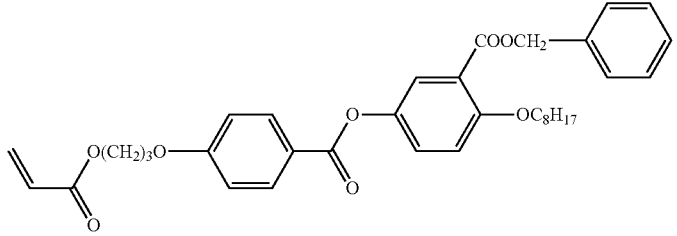
1-A-10
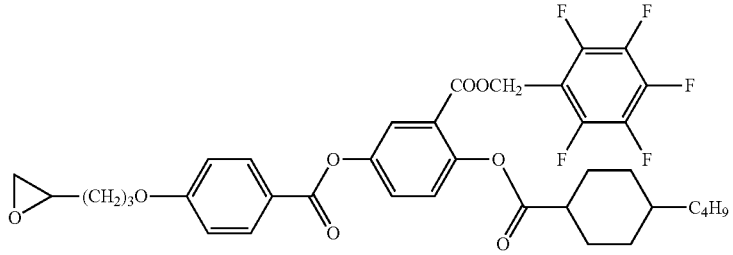
1-A-11

-continued
1-A-12
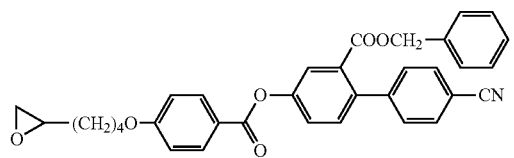
1-A-13
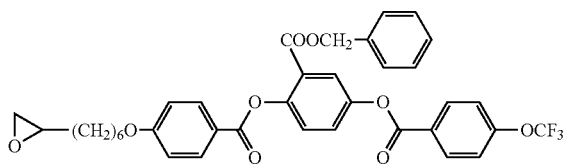
1-A-14
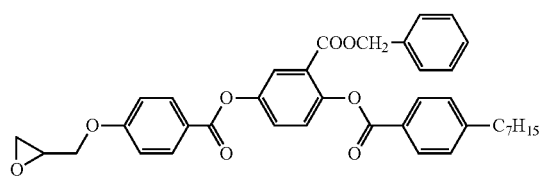
1-A-15
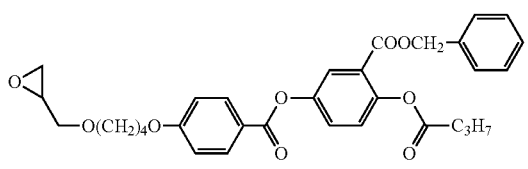
1-A-16
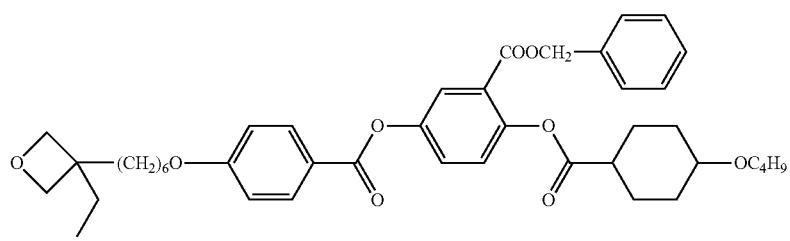
1-A-17
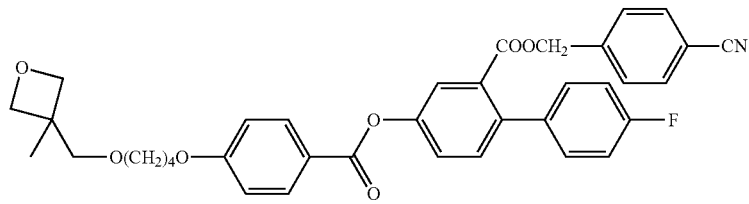
1-A-18
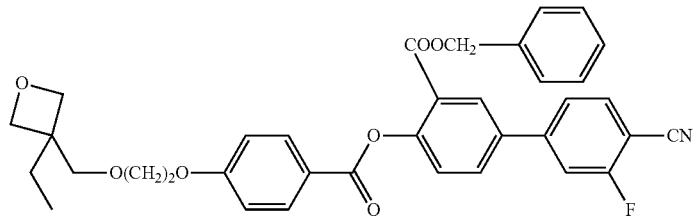
1-A-19
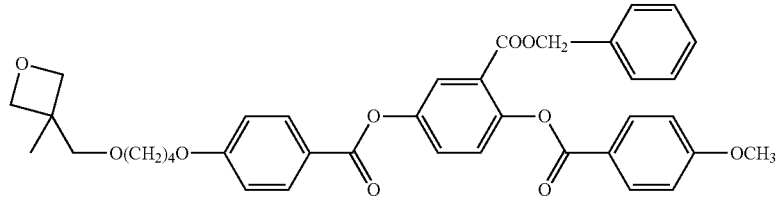
1-A-20
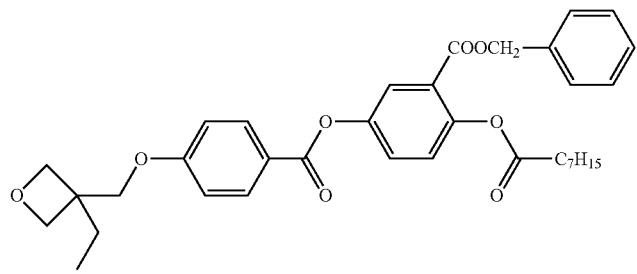

-continued
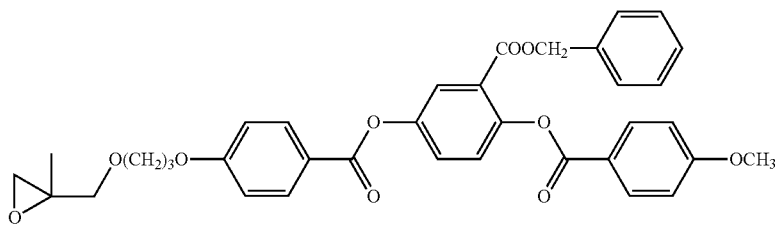
1-A-21
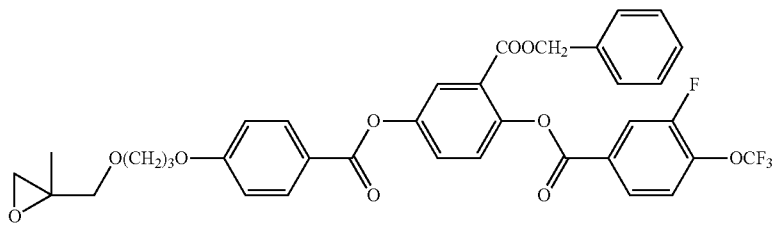
1-A-22
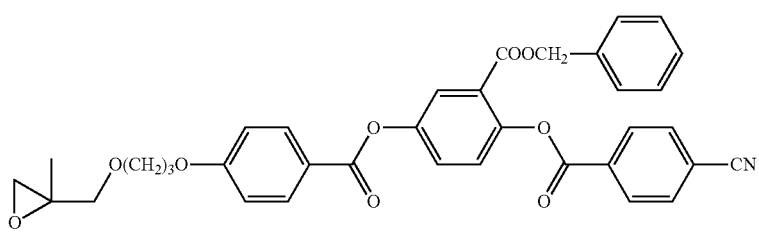
1-A-23
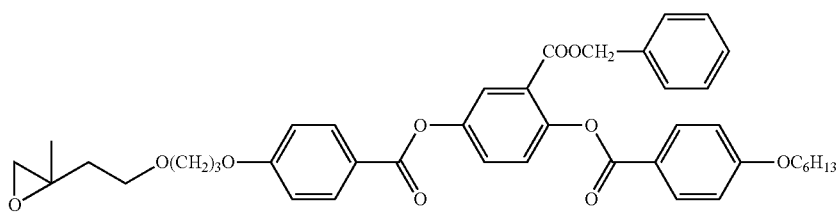
1-A-24
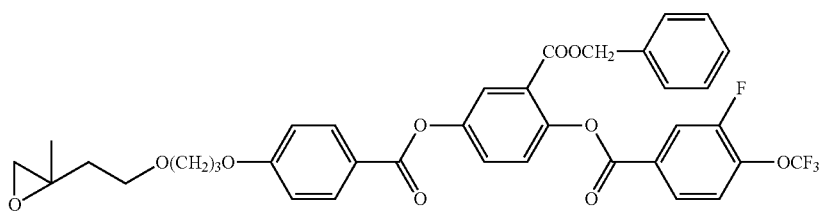
1-A-25
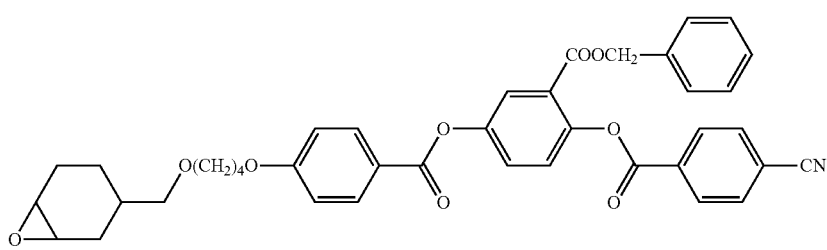
1-A-26
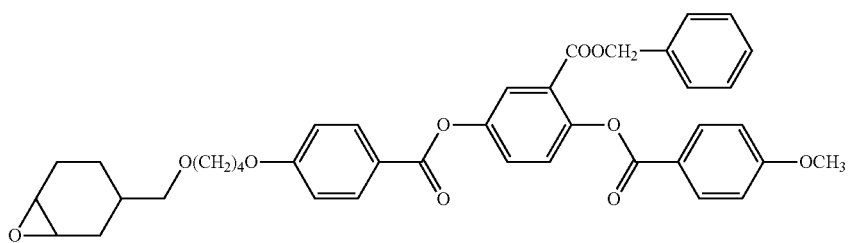
1-A-26

-continued
1-A-26
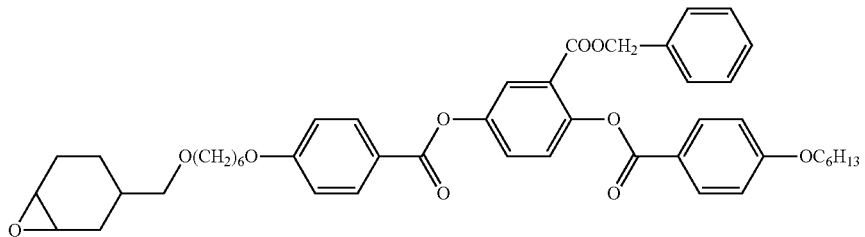
1-A-26
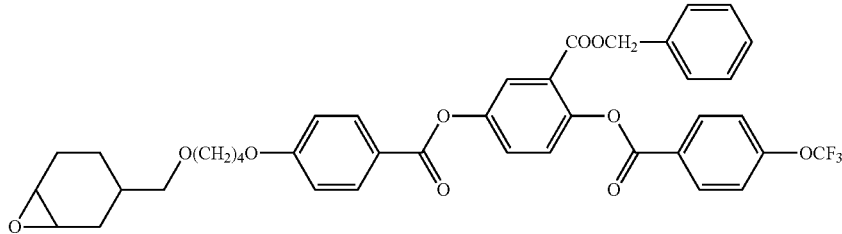
1-B-1
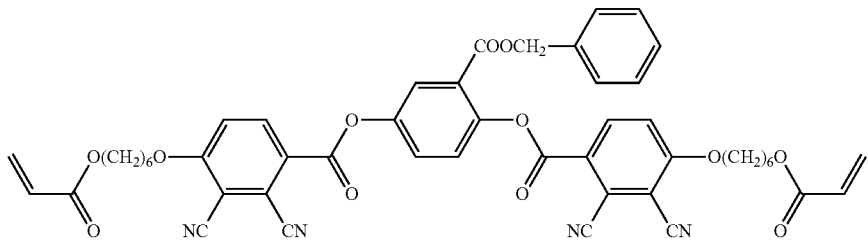
1-B-2
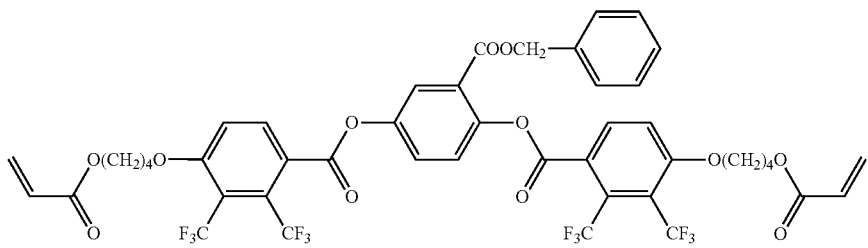
1-B-3
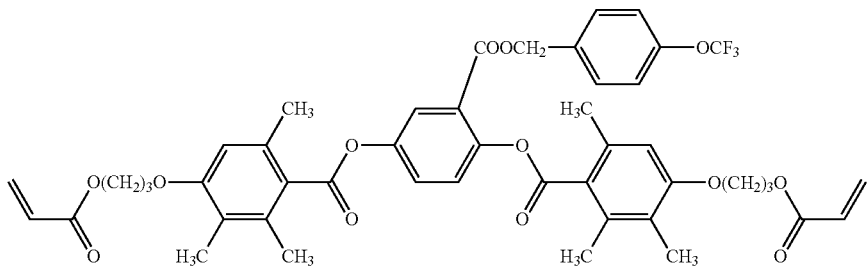
1-B-4
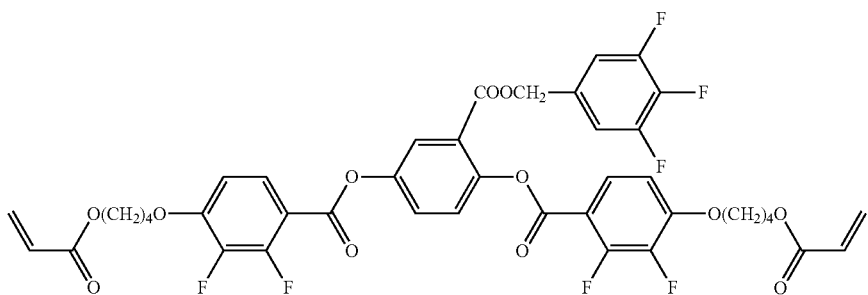

-continued
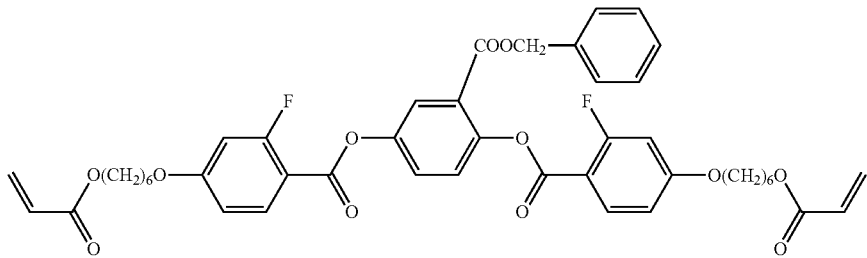
1-B-5
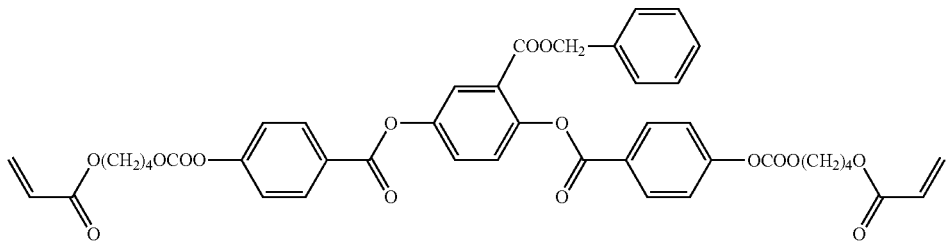
1-B-6
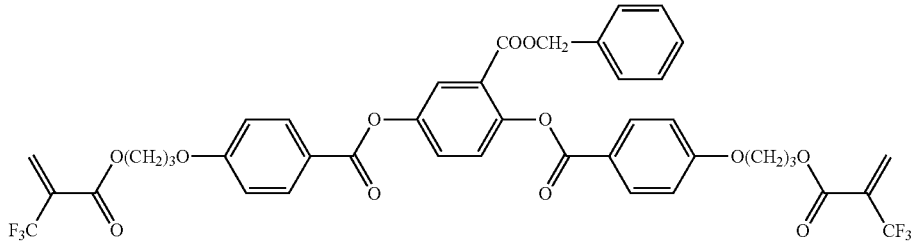
1-B-7
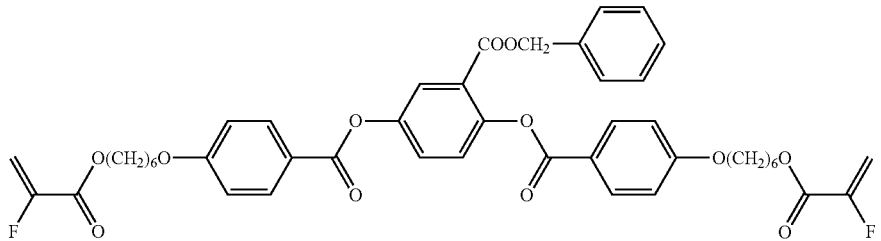
1-B-8
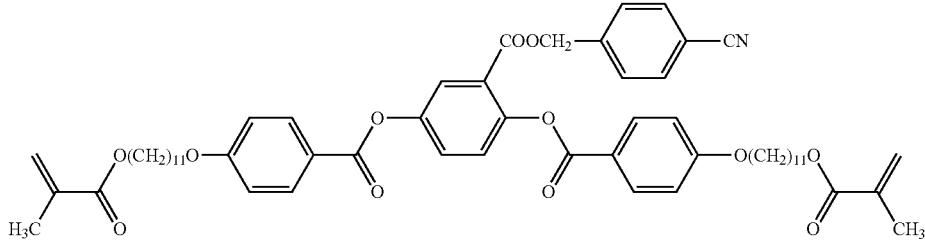
1-B-9
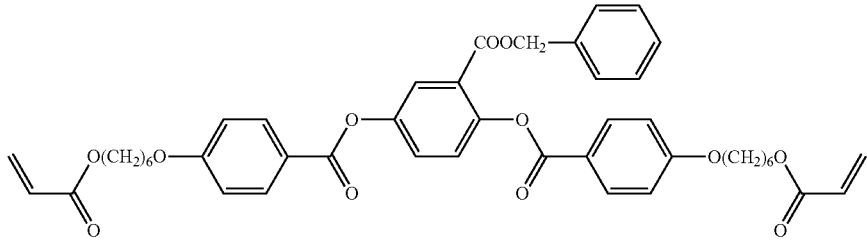
1-B-10

-continued
1-B-11
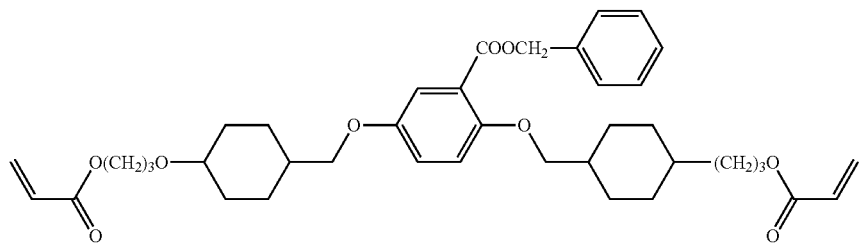
1-B-12
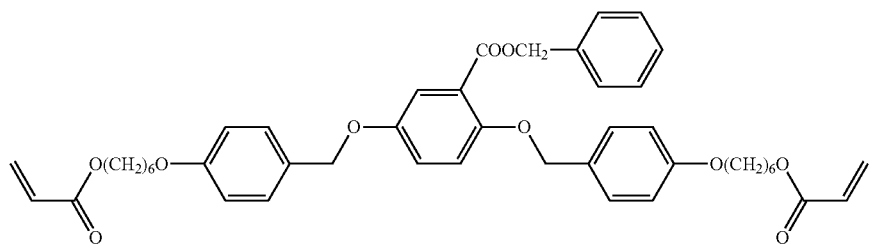
1-B-13
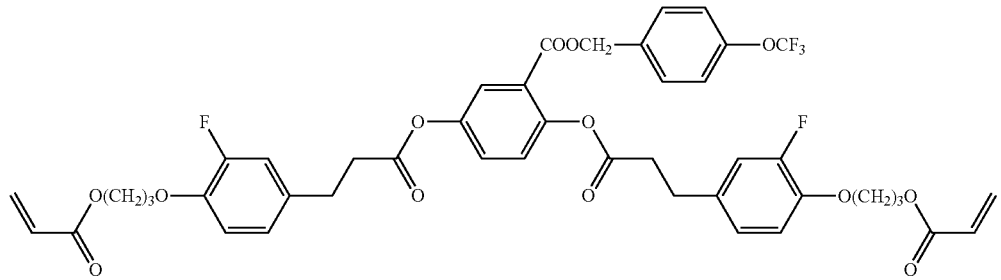
1-B-14
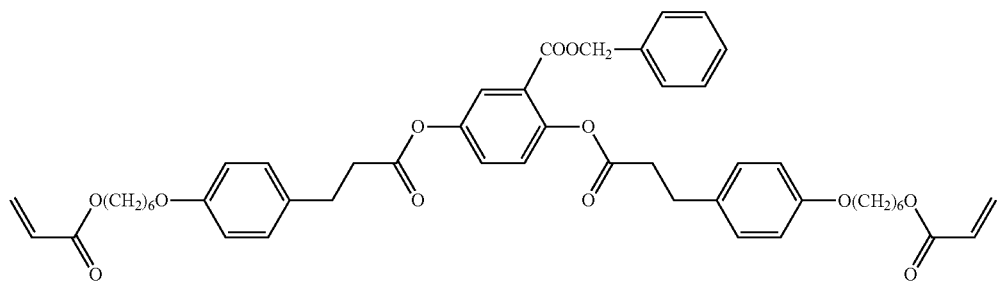
1-B-15
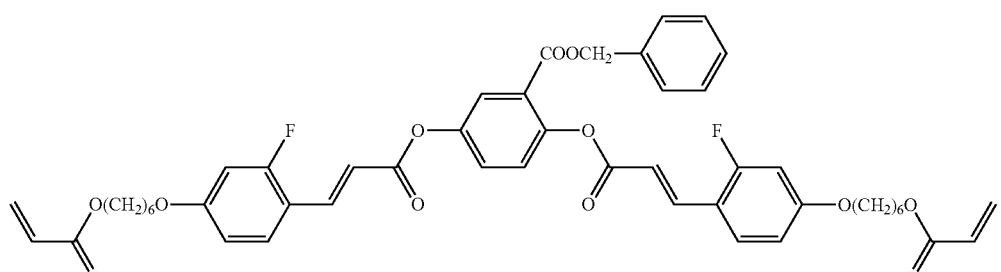
1-B-16
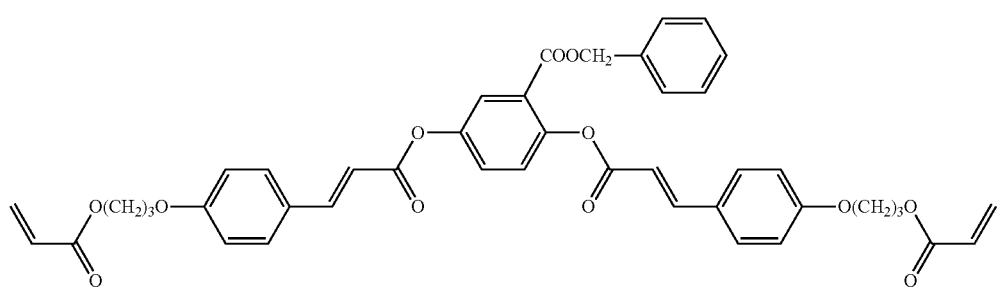

-continued
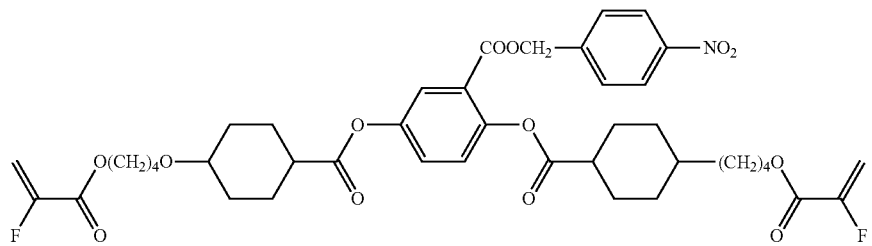
1-B-17
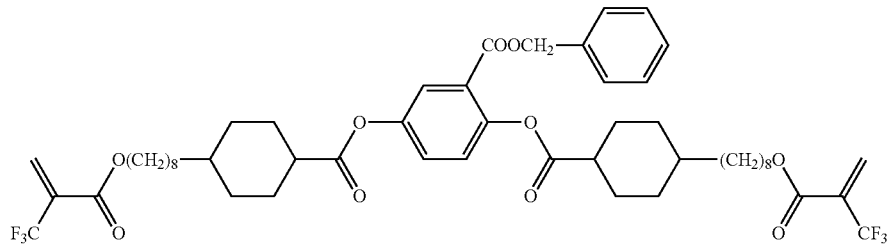
1-B-18
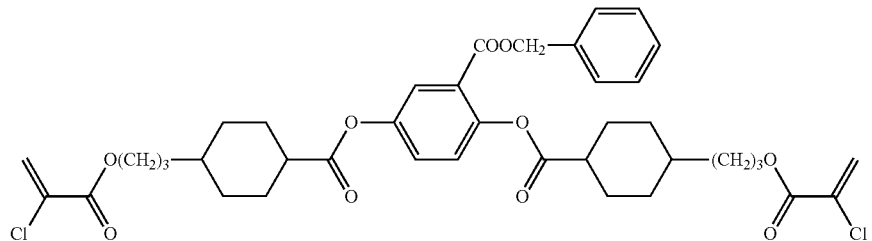
1-B-19
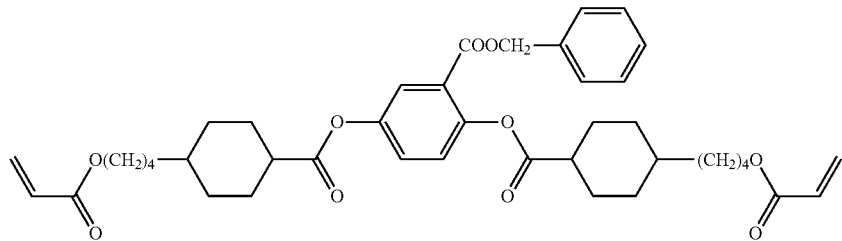
1-B-20
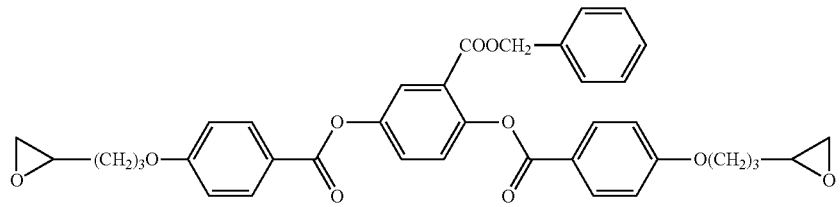
1-B-21
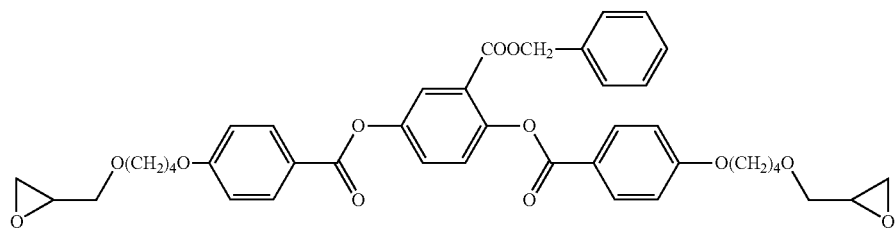
1-B-22

-continued
1-B-23
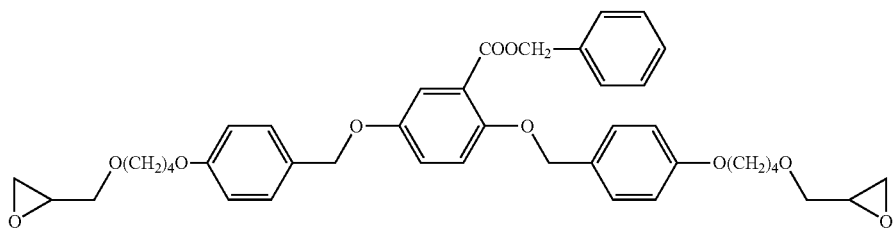
1-B-24
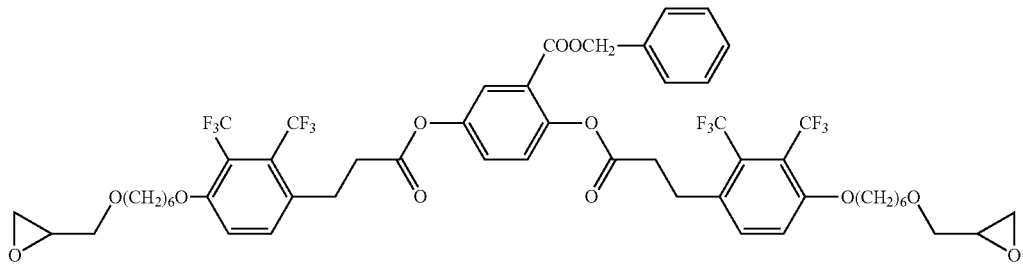
1-B-25
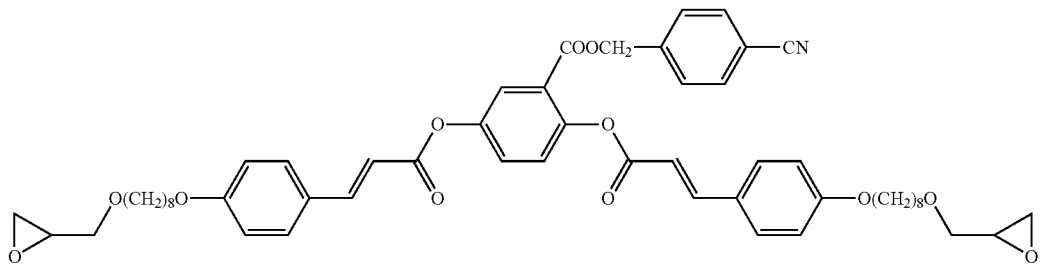
1-B-26
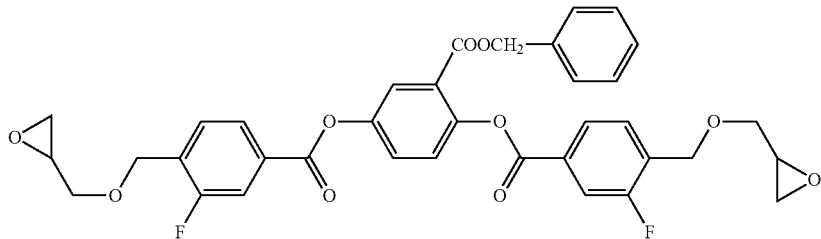
1-B-27
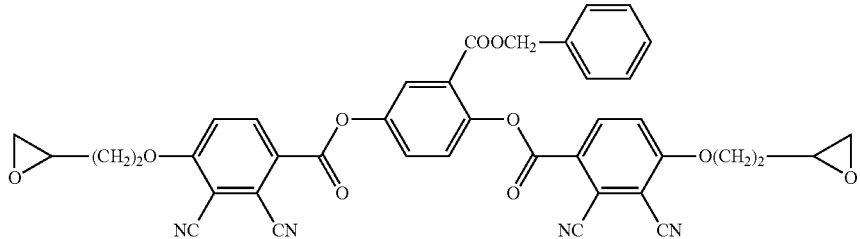
1-B-28
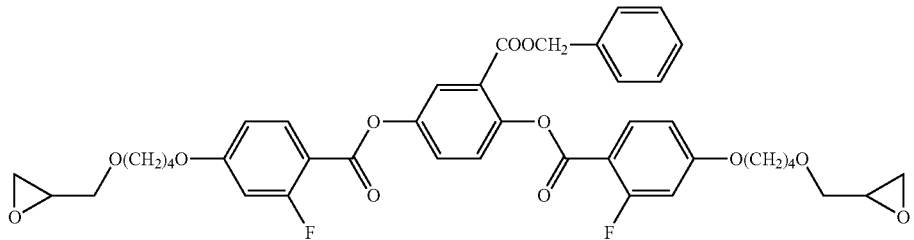

-continued
1-B-29
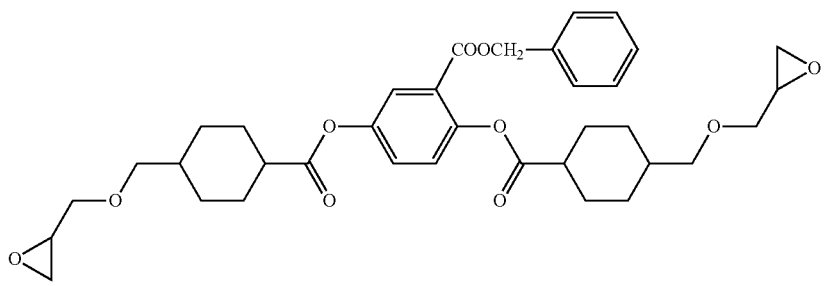
1-B-30
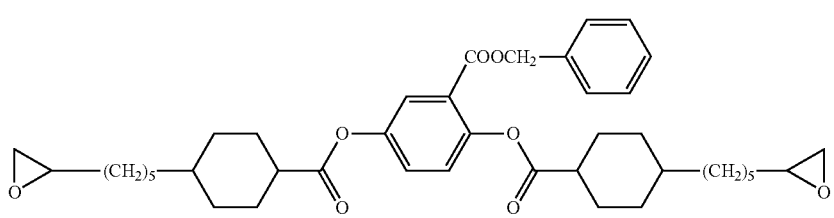
1-B-31
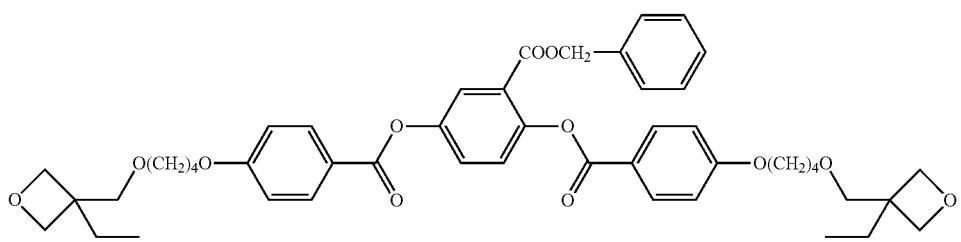
1-B-32
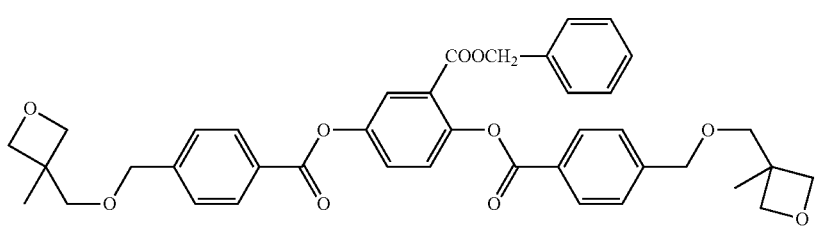
1-B-33
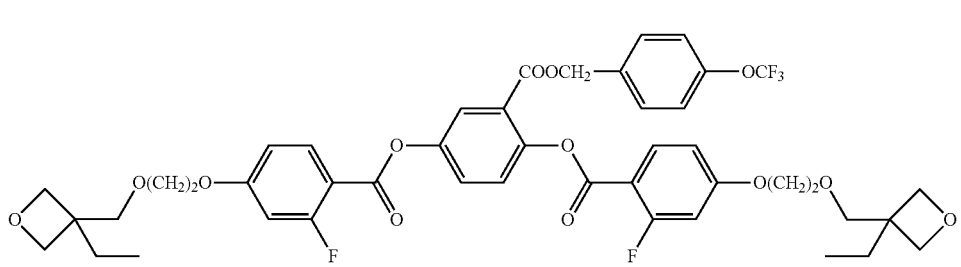
1-B-34
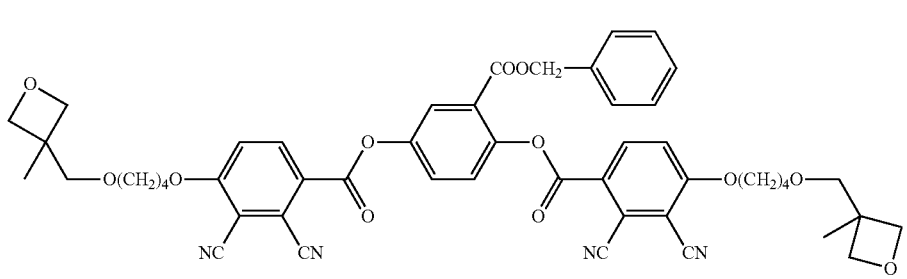

1-B-35
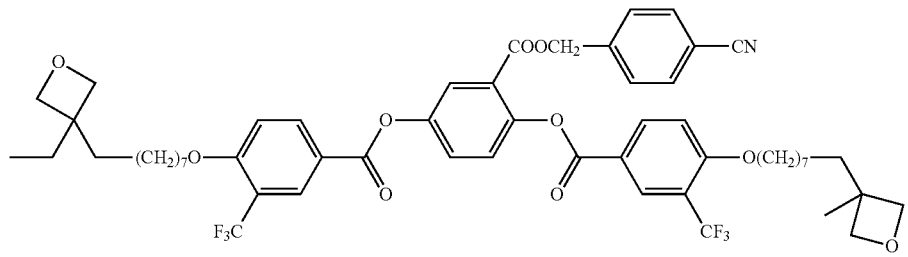
1-B-36
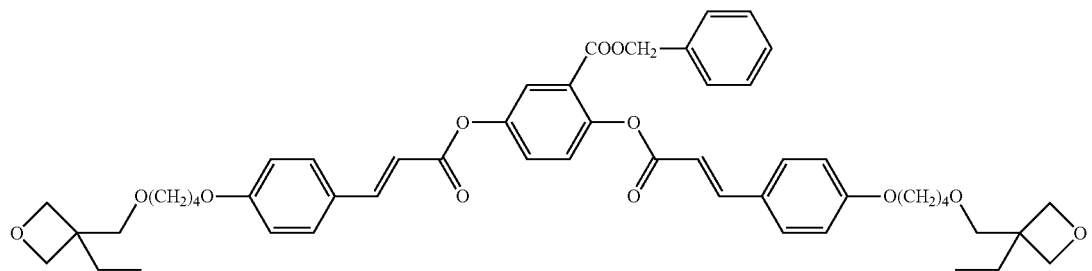
1-B-37
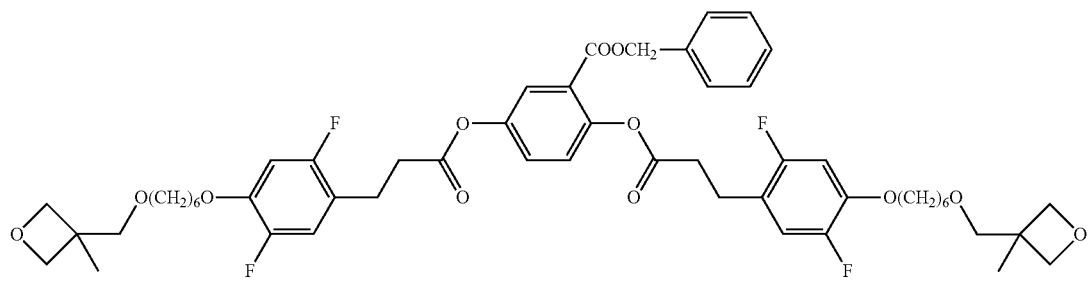
1-B-38
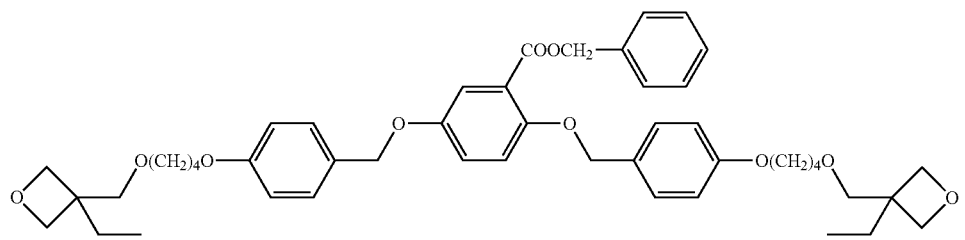
1-B-39
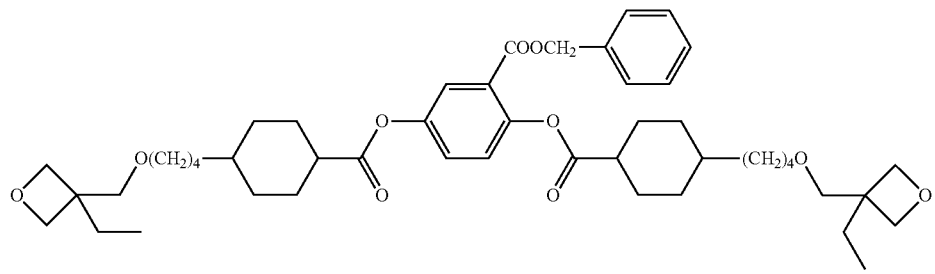
1-B-40
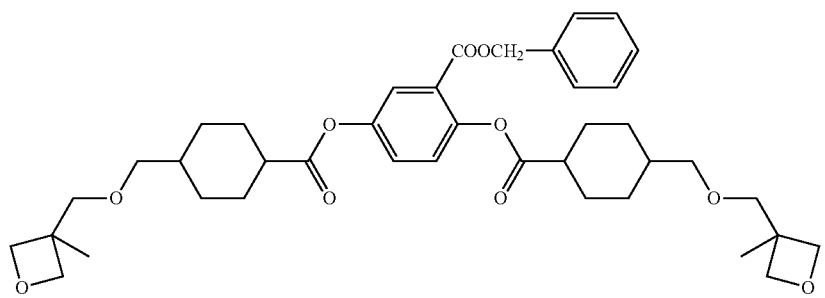

-continued
1-B-41
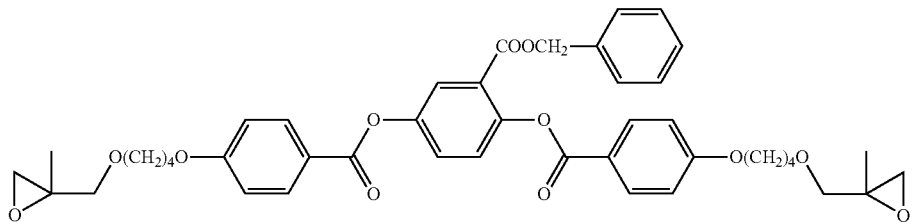
1-B-42
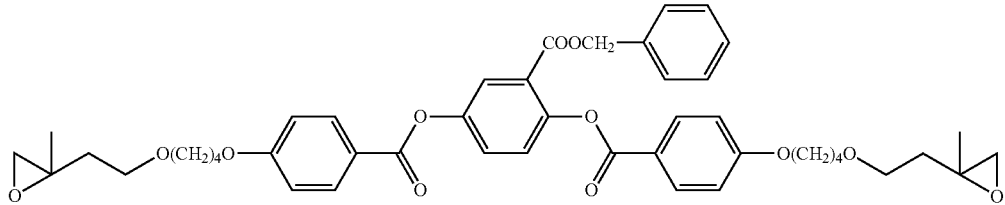
1-B-43
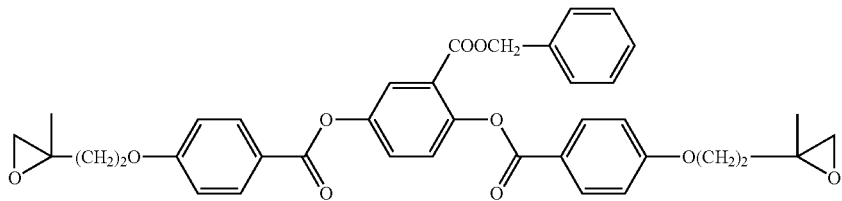
1-B-44
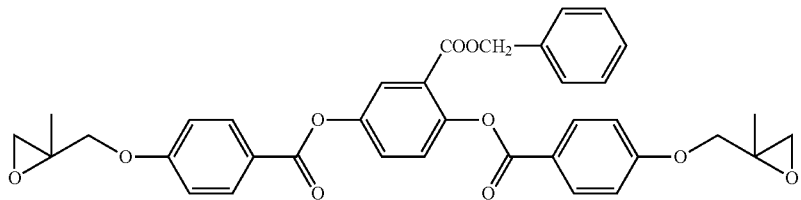
1-B-45
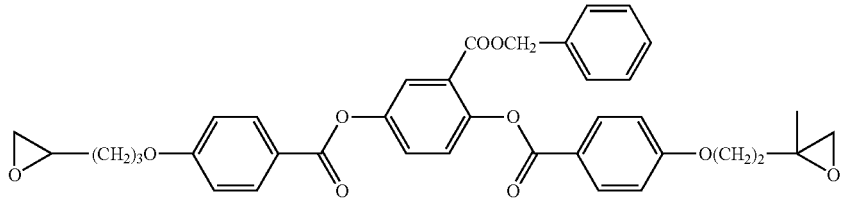
1-B-46
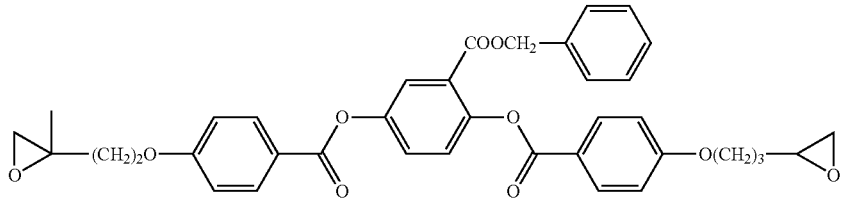
1-B-47
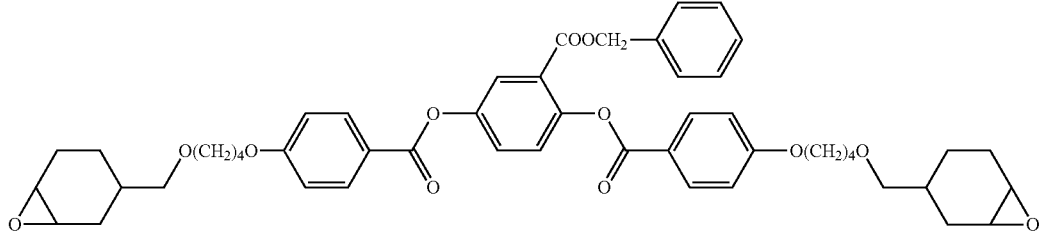

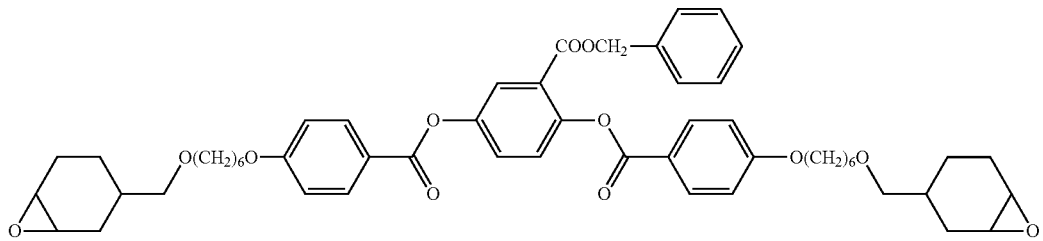

1-B-48

Compositions

The composition (1) of the invention has characteristics such as excellent coating properties. In the first aspect, the composition (1) includes one compound selected from the compound (1). Polymerization of this composition gives a homopolymer. In the second aspect, the composition includes at least two compounds selected from the compound (1). A copolymer is formed by polymerization of this composition. These compositions may further include an additive. In the third aspect, the composition (1) includes at least one compound selected from the compound (1) and another polymerizable compound. Although another polymerizable compound has a polymerizable group, it is different from the compound (1). A copolymer is also formed by polymerization of this composition. The composition (1) may further include another polymerizable compound, a liquid crystal compound, an optically active compound, a polymerization initiator, a solvent, an additive and so forth. The additive includes a surfactant, an organosilicon compound, a chain-transfer agent, a polymerization inhibitor, an oxygen inhibitor, an ultraviolet absorber. These compounds and the additive will be sequentially explained.

The composition (1) may include another polymerizable compound. It is desirable for another polymerizable compound that the ability to form a coat of the composition and mechanical strength of the polymer are not decreased. Another polymerizable compound is classified into a compound having liquid crystallinity and a compound having no liquid crystallinity.

Another polymerizable compound having liquid crystallinity is suitable to adjust the temperature range of a liquid crystal phase, the optical anisotropy, the coating properties and so forth of the composition (1). Examples of such compounds include liquid crystal compounds having a functional group such as an acryloyloxy group, a methacryloyloxy group, a fumaroyloxy group, a maleimidyl group, an oxirane ring or an oxetane ring, and being different from the compound (1).

It is desirable that the composition (1) includes a polymerizable compound other than the compound (1) preferably in the range of approximately 10% to approximately 97% by weight, and more preferably in the range of approximately 20 to approximately 85% by weight in order to markedly exhibit characteristics of the polymer of the invention and characteristics of a copolymer. The ratio of the polymerizable compound having no liquid crystallinity to the polymerizable compound having liquid crystallinity can be varied without any restraint if the total weight of these compounds falls into the range described above. Only one of these compounds may be included.

Desirable examples of another polymerizable compound having liquid crystallinity are compounds represented by formula (M1), formula (M2-1), formula (M2-2), formula (M2-3), formula (M2-4), formula (M2-5), formula (M3) and formula (M4). These compounds are generically referred to as the compound (M).

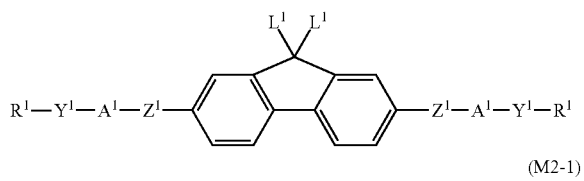

(M1)

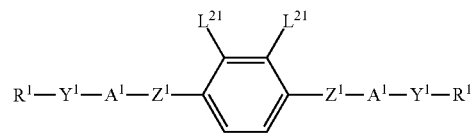

(M2-1)

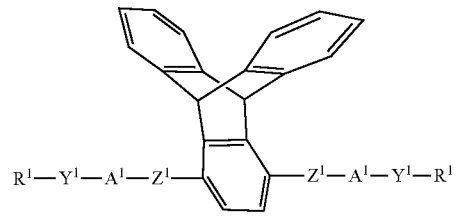

(M2-2)

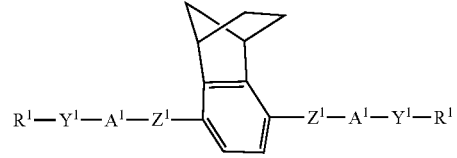

(M2-3)

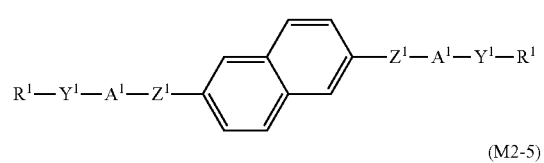

(M2-4)

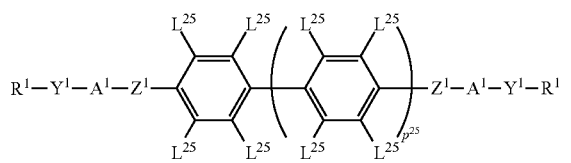

(M2-5)

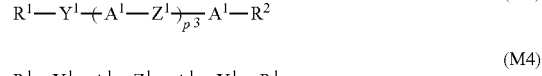

(M3)

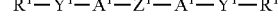

(M4)

In formula (M1), formula (M2-1) to formula (M2-5), formula (M3) and formula (M4), $R^1$ is independently a substituent represented by formula (a-4), formula (a-5) or formula (a-9):

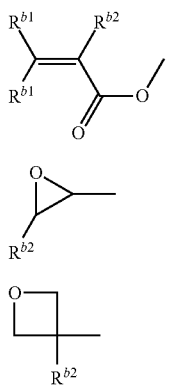

wherein $R^{b1}$ and $R^{b2}$ are each independently hydrogen, halogen, alkyl having 1 to 5 carbons or halogenated alkyl having 1 to 5 carbons. A desirable example of $R^{b1}$ is hydrogen and desirable examples of $R^{b2}$ are hydrogen, methyl and ethyl.

In formula (M-3), $R^2$ is alkyl having 1 to 10 carbons, alkoxy having 1 to 10 carbons, chlorine, fluorine, cyano, —$CF_3$ or —$OCF_3$. Desirable examples of $R^2$ are alkyl having 1 to 8 carbons, alkoxy having 1 to 8 carbons, chlorine, fluorine, cyano, —$CF_3$ and —$OCF_3$. More desirable examples of $R^2$ are alkyl having 1 to 8 carbons, alkoxy having 1 to 8 carbons, fluorine, cyano and —$OCF_3$.

In formula (M1), formula (M2-1) to formula (M2-5), formula (M3) and formula (M4), $A^1$ is independently 1,4-cyclohexylene or 1,4-phenylene, and in the 1,4-phenylene, arbitrary hydrogen may be replaced by fluorine. Desirable examples of $A^1$ are 1,4-cyclohexylene, 1,4-phenylene, monofluoro-1,4-phenylene and difluoro-1,4-phenylene.

In formula (M1), formula (M2-1) to formula (M2-5), formula (M3) and formula (M4), $Z^1$ is independently a single bond, —$CH_2CH_2$—, —$CH_2O$—, —$OCH_2$—, —COO—, —OCO—, —CH=CH—, —C≡C—, —CH=CHCOO—, —OCOCH=CH—, —$(CH_2)_2COO$— or —$OCO(CH_2)_2$—. Desirable examples of $Z^1$ are a single bond, —$CH_2O$—, —$OCH_2$—, —COO—, —OCO—, —C≡C—, —CH=CHCOO—, —OCOCH=CH—, —$(CH_2)_2COO$— and —$OCO(CH_2)_2$—. More desirable examples of $Z^1$ are a single bond, —COO—, —OCO—, —CH=CHCOO—, —OCOCH=CH—, —$(CH_2)_2COO$— and —OCO$(CH_2)_2$—.

In formula (M1), formula (M2-1) to formula (M2-5), formula (M3) and formula (M4), $Y^1$ is independently a single bond or alkylene having 1 to 20 carbons, and in the alkylene, arbitrary —$CH_2$— may be replaced by —O—, —CO—, —COO—, —OCO—, —OCOO— or —CH=CH—. Desirable examples of $Y^1$ are a single bond or alkylene having 1 to 12 carbons, and in the alkylene, arbitrary —$CH_2$— may be replaced by —O—, —COO—, —OCP— or —OCOO. More desirable examples of $Y^1$ area single bond or alkylene having 1 to 10 carbons, and in the alkylene, —$CH_2$— that is bonded to the ring $A^1$ may be replaced by —O—, —COO—, —OCO— or —OCOO.

In formula (M1), $L^1$ is independently hydrogen, fluorine or methyl. Desirable examples of $L^1$ are hydrogen and methyl. $L^{21}$ in formula (M2-1) is independently hydrogen, halogen, cyano, alkyl having 1 to 8 carbons or halogenated alkyl having 1 to 8 carbons. Desirable examples of $L^{21}$ are hydrogen, halogen, cyano, alkyl having 1 to 5 carbons and halogenated alkyl having 1 to 5 carbons, and more desirable examples are hydrogen, fluorine, methyl, cyano, isopropyl, tert-butyl and trifluoromethyl. $L^{25}$ in formula (M2-5) is independently hydrogen, halogen, alkyl having 1 to 8 carbons, alkoxy having 1 to 8 carbons, cyano or halogenated alkyl having 1 to 8 carbons. Desirable examples of $L^{25}$ are hydrogen, halogen, cyano, alkyl having 1 to 5 carbons, alkoxy having 1 to 5 carbons and halogenated alkyl having 1 to 5 carbons. More desirable examples are hydrogen, fluorine, methyl and methoxy. $p^{25}$ in formula (M2-5) is 1 or 2. $p^3$ in formula (M4) is 1 or 2. Desirable $p^3$ is 2.

The compound (M1), the compound (M2-1) to the compound (M2-5) and the compound (M4) have two polymerizable groups, together with a wide temperature range of a liquid crystal phase. These polymerizable groups can form a three-dimensional network structure, making it possible to form a polymer having a high mechanical strength.

The compound (M2-2) has an especially large internal free volume because of the presence of a triptycene ring in the structure, and thus decreases the optical anisotropy when it is used together with the compound (1). The compound (M2-3) has also the same effect as the compound (M2-2). Since the compound (M3) has only one polymerizable group, a substituent such as a polar group can be introduced to the opposite side of the major axis direction of the molecule, thus making it possible to adjust orientation in the liquid-crystal state. In any of the compound (M1), the compound (M2-1) to the compound (M2-5), the compound (M3) and the compound (M4), a composition that has a large optical anisotropy (Δn) can be prepared when the ring $A^1$ is 1,4-phenylene, and a composition that has a small optical anisotropy can be prepared when the ring $A^1$ is 1,4-cyclohexylene.

Desirable examples of the compound (M1), the compound (M2-1), the compound (M2-2), the compound (M2-3), the compound (M2-4), the compound (M2-5), the compound (M3) and the compound (M4) include the compounds (M1-1) to (M1-3), the compounds (M2-1-1) to (M2-1-12), the compounds (M2-2-1) to (M2-2-4), the compounds (M3-1) to (M3-16) and the compounds (M4-1) to (M4-5).

The meanings of $Y^1$ in the following compounds are the same with those of $Y^1$ in formula (M1), formula (M2-1), formula (M2-2), formula (M2-3), formula (M3) and formula (M4), and $R^1$ is a substituent represented by the following formula (a-4-1), formula (a-5-1), formula (a-9-1) or formula (a-9-2).

(a-4-1)

(a-5-1)

(a-9-1)

(a-9-2)

Desirable examples of the compound (M1) are shown below.

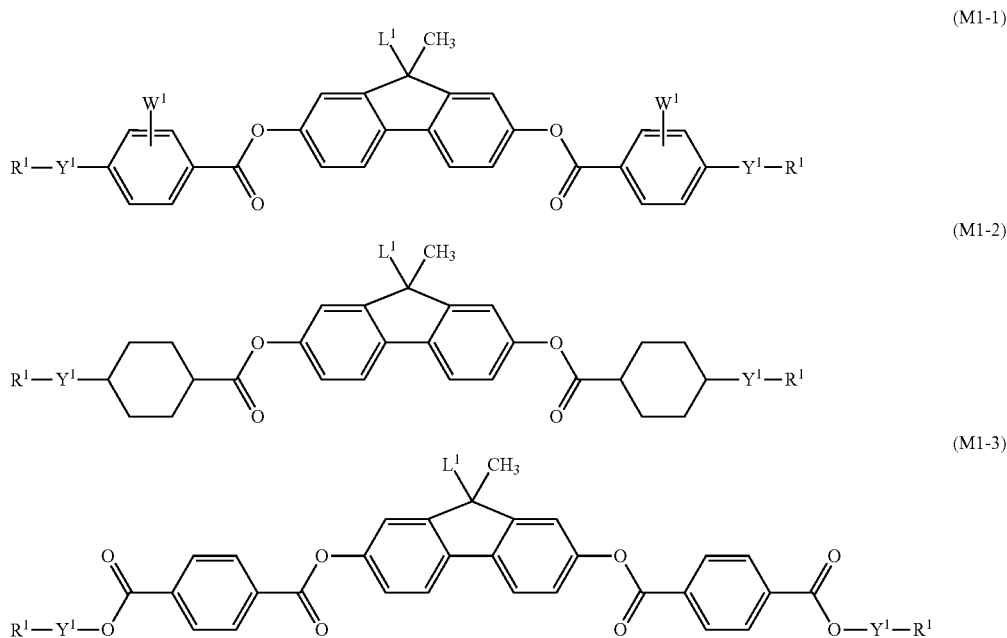

In formula (M1-1) to formula (M1-3) above, $Y^1$ is alkylene having 2 to 12 carbons, and in the alkylene, one or two non-adjacent —$CH_2$— may be replaced by —O—, $W^1$ is hydrogen or fluorine, $L^1$ is hydrogen or methyl, and $R^1$ is a substituent represented by formula (a-4-1), formula (a-5-1) or formula (a-9-2).

Concrete examples of the compound (M1-1) to the compound (M1-3) are shown below. In the following concrete examples, n and m are each independently an integer from 2 to 12.

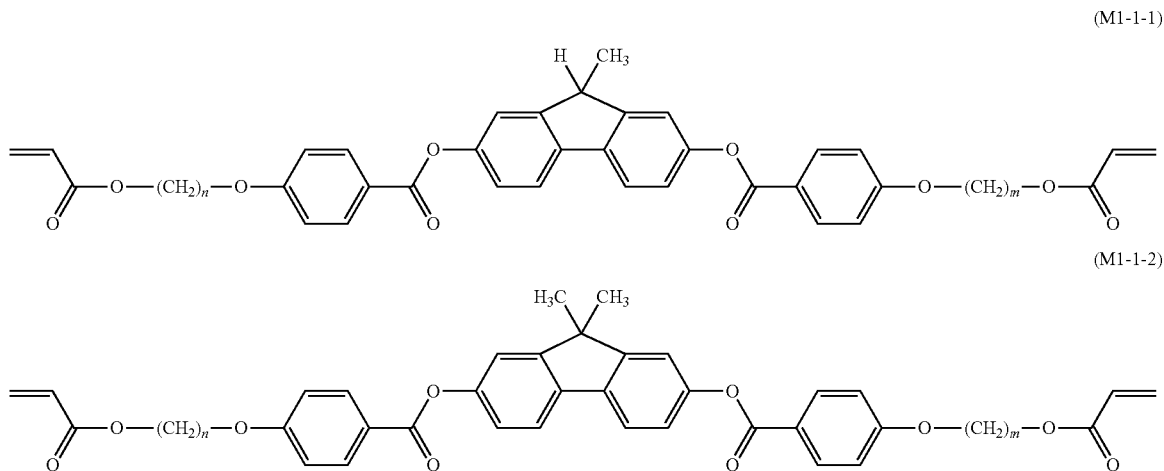

(M1-1-3)
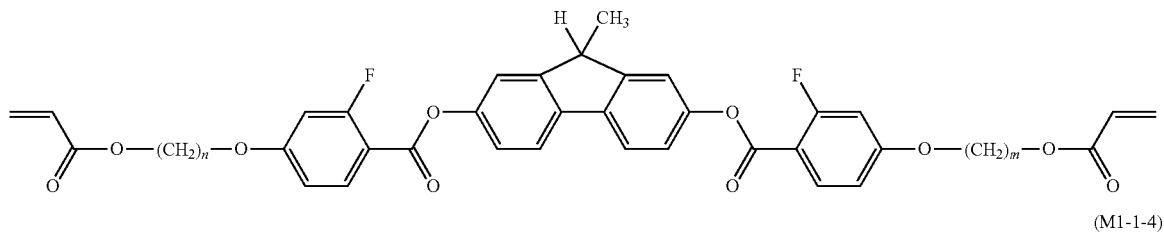
(M1-1-4)
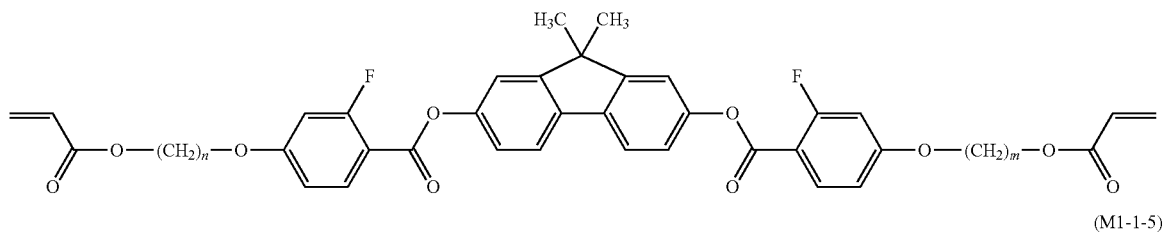
(M1-1-5)
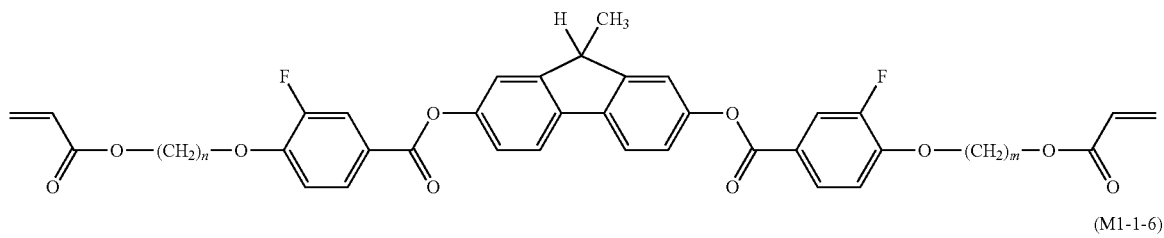
(M1-1-6)
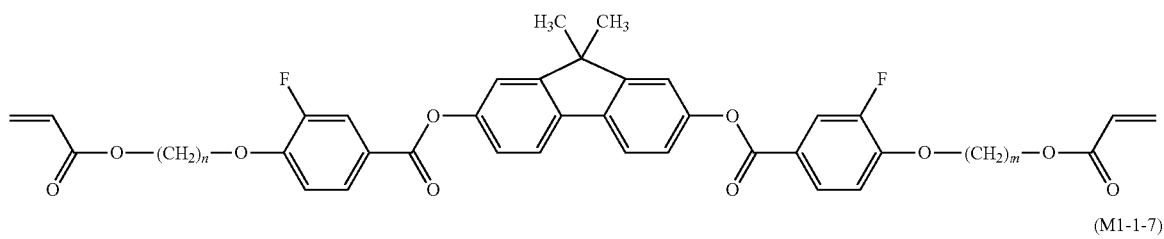
(M1-1-7)
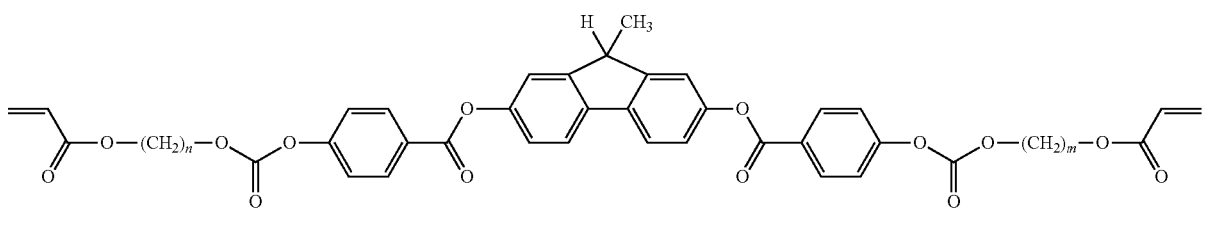
(M1-1-8)
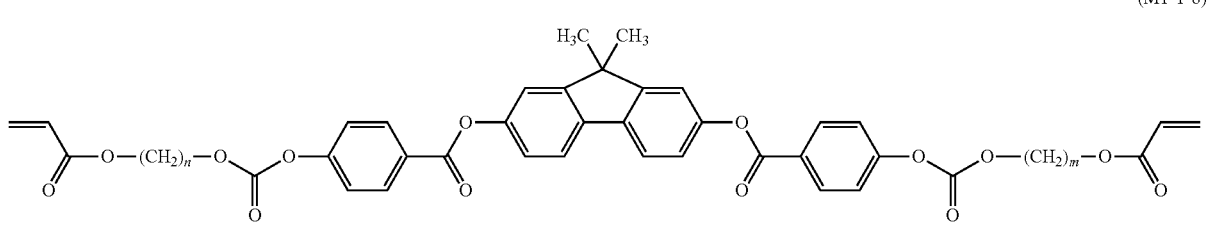
(M1-2-1)
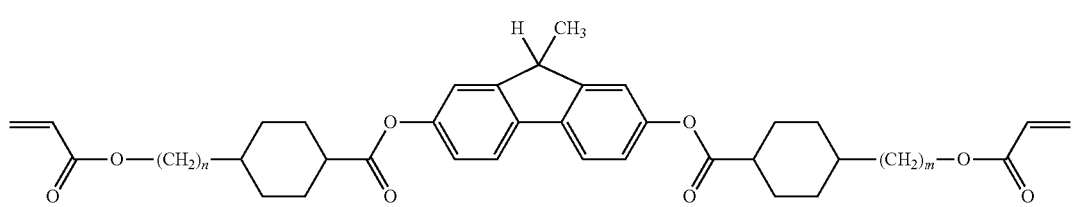

-continued
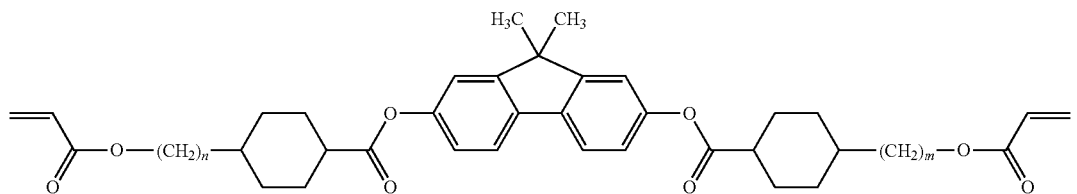
(M1-2-2)
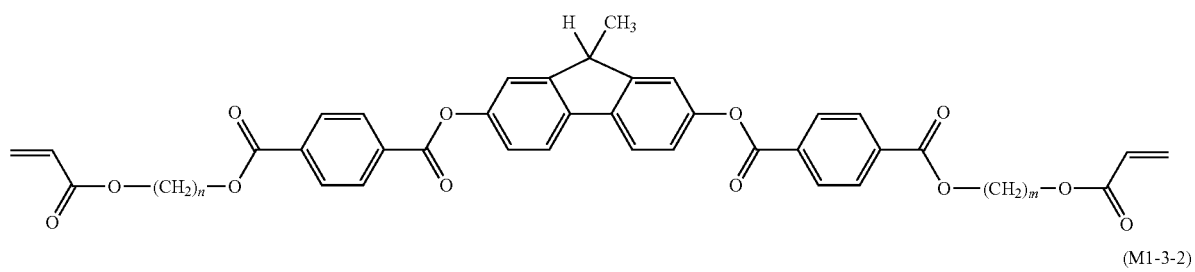
(M1-3-1)
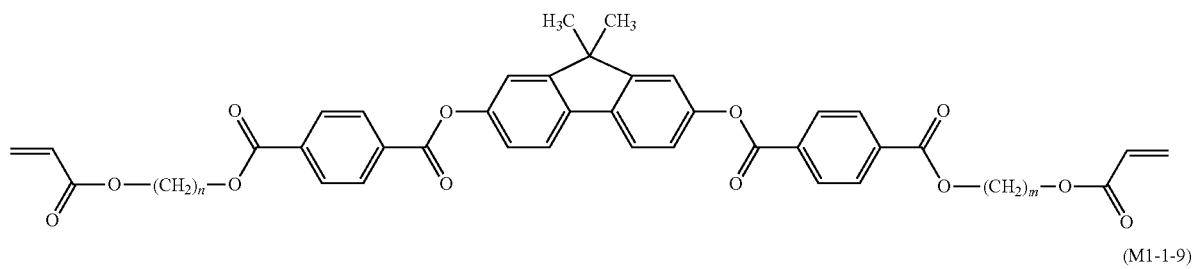
(M1-3-2)
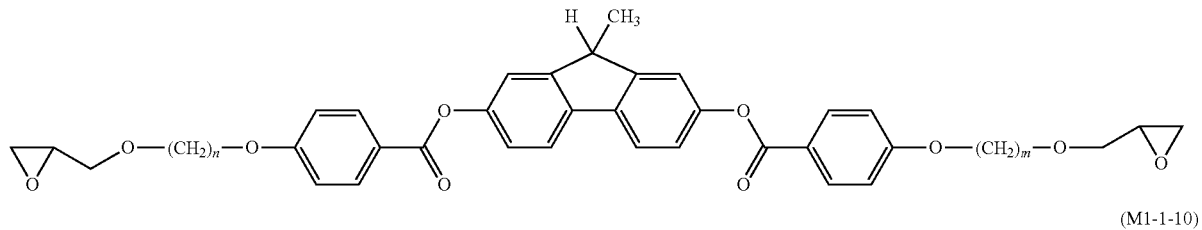
(M1-1-9)
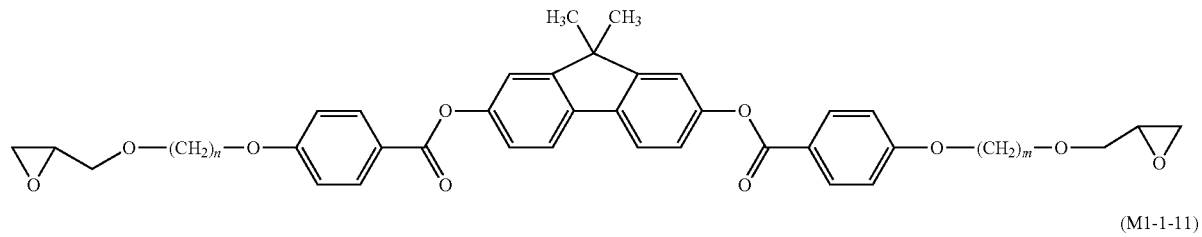
(M1-1-10)
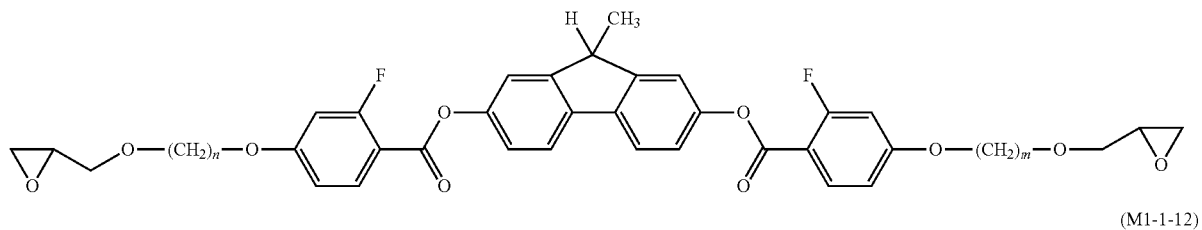
(M1-1-11)
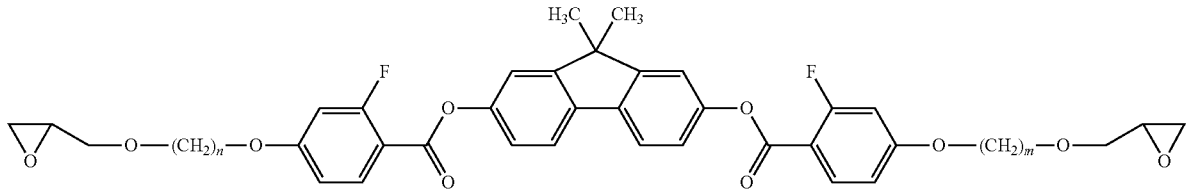
(M1-1-12)

(M1-1-13)
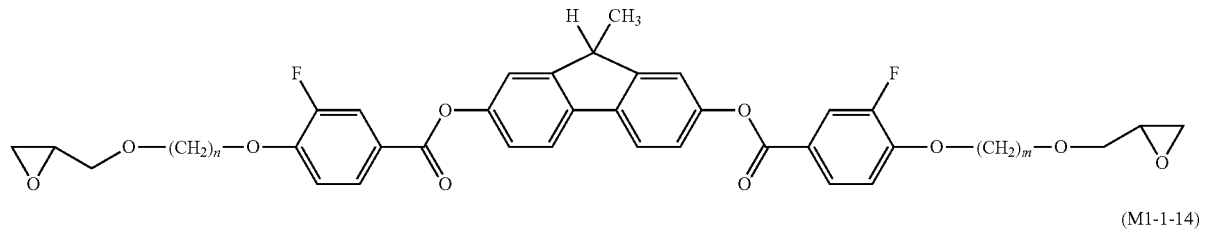
(M1-1-14)
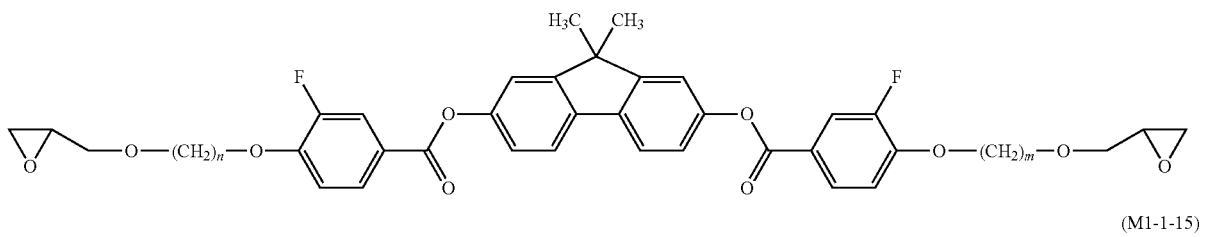
(M1-1-15)
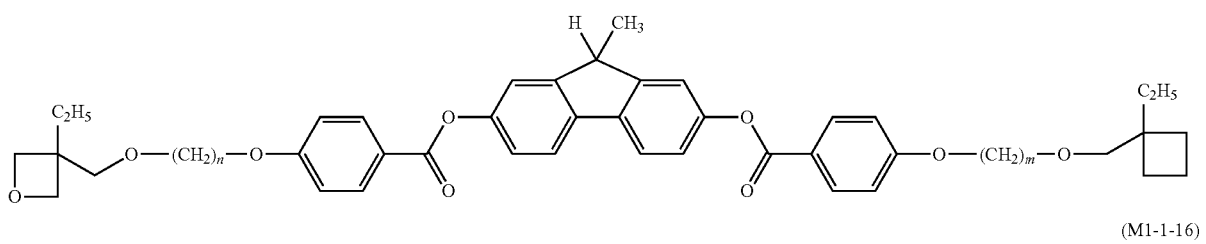
(M1-1-16)
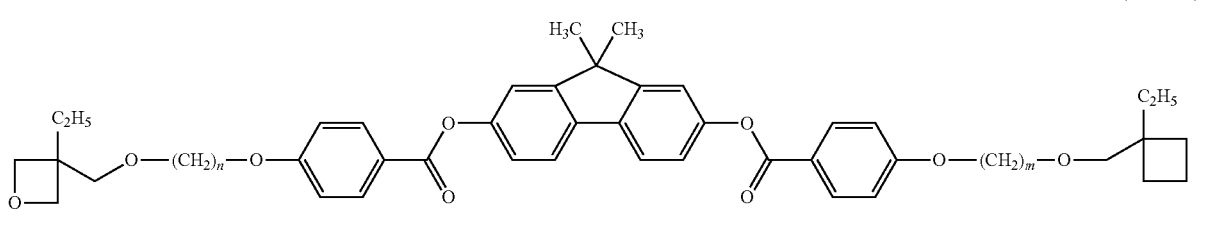
(M1-1-17)
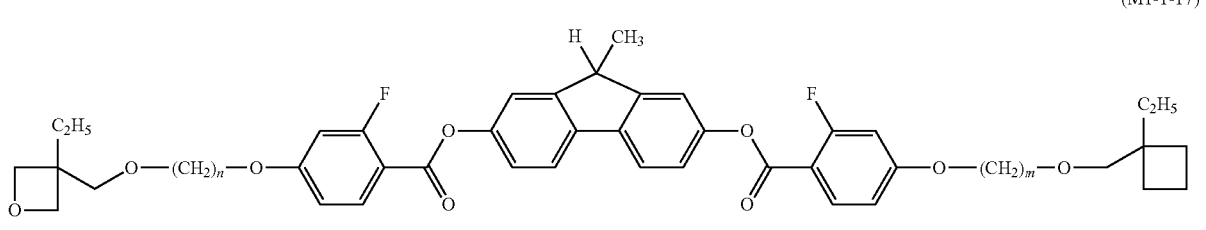
(M1-1-18)
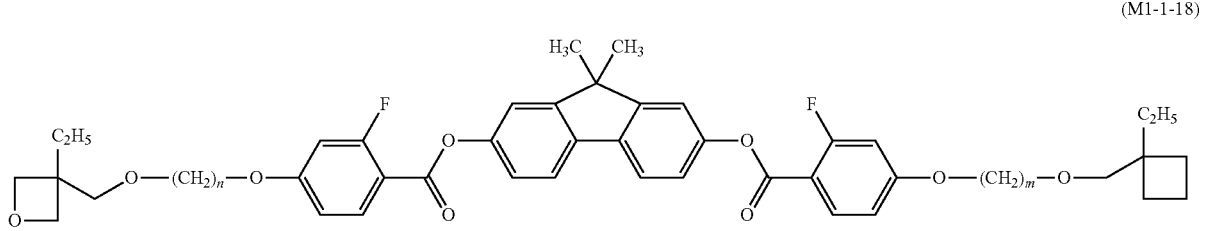
(M1-1-19)
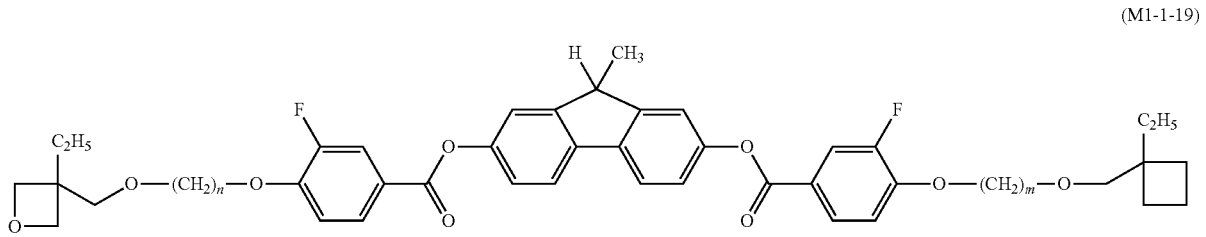

(M1-1-20)
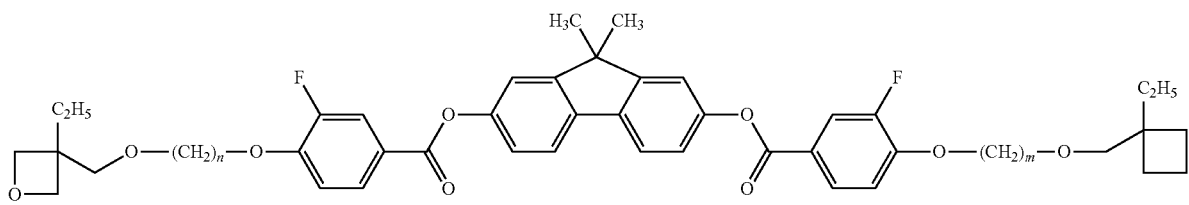
Desirable examples of the compound (M2-1) are shown below.
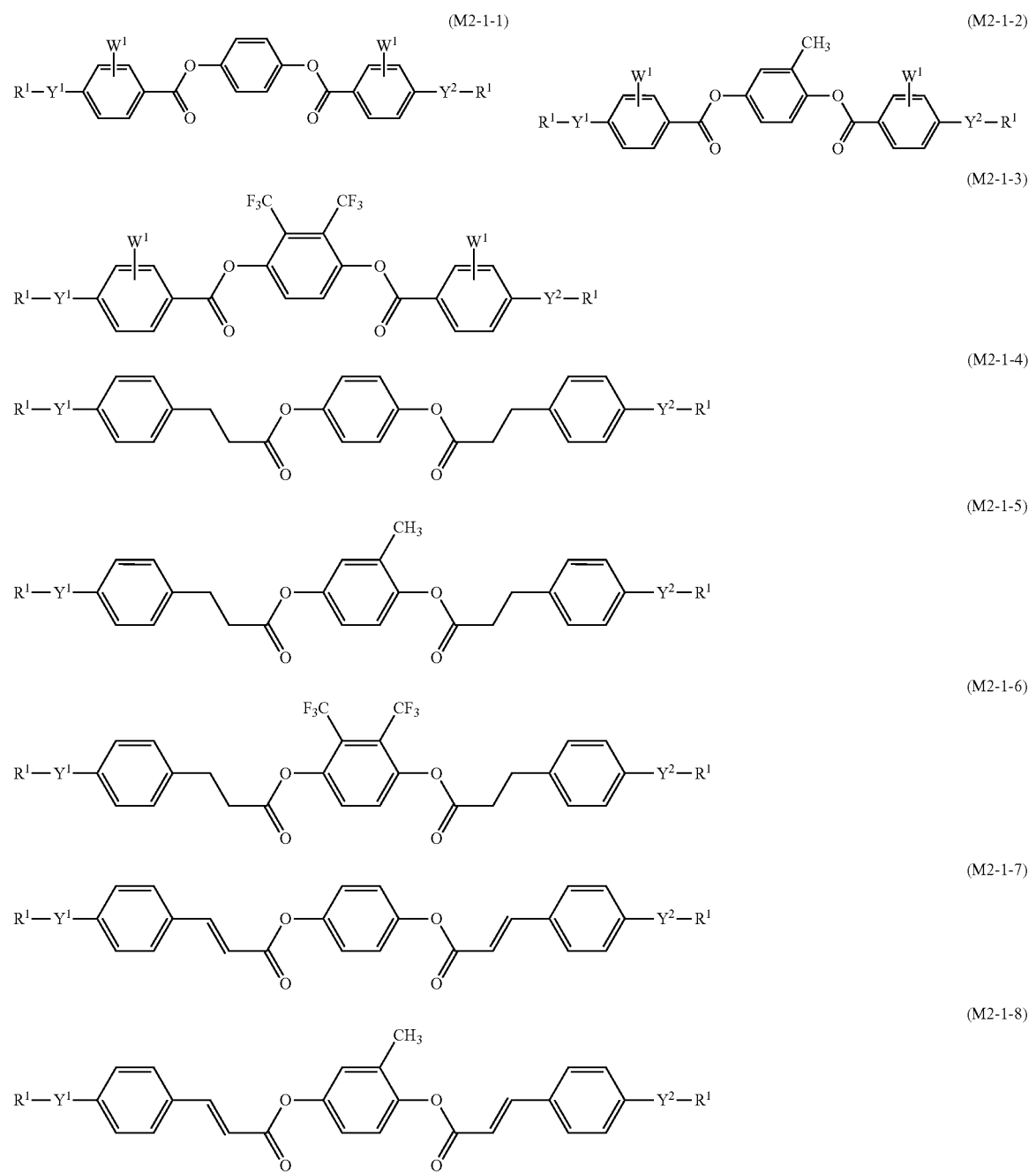

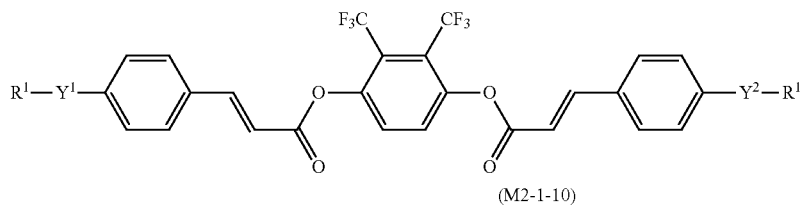
(M2-1-9)

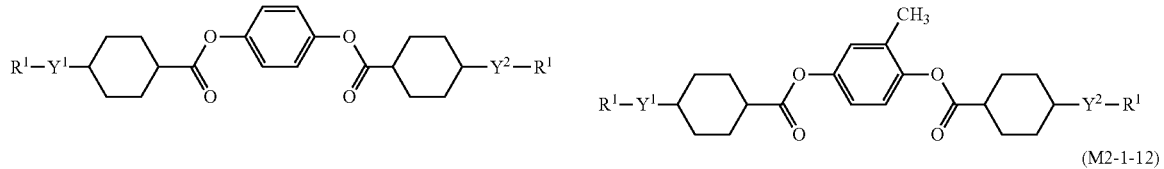
(M2-1-10)

(M2-1-11)

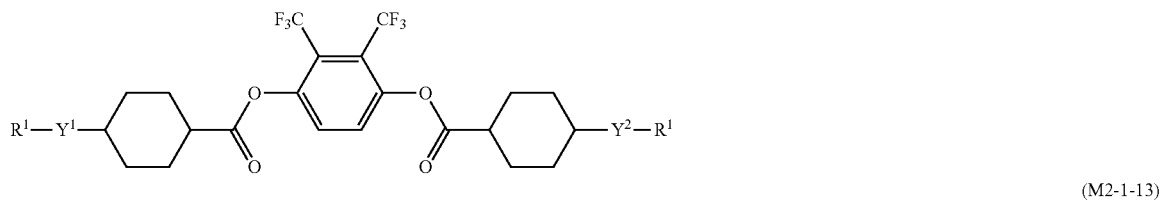
(M2-1-12)

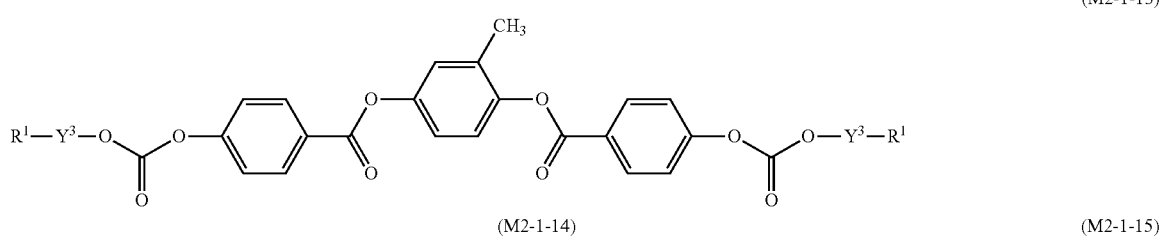
(M2-1-13)

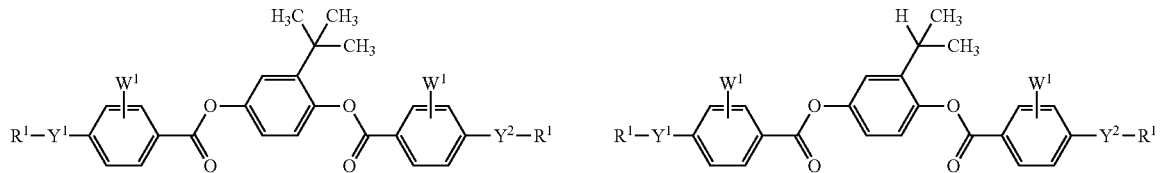
(M2-1-14)

(M2-1-15)

In formula (M2-1-1) to formula (M2-1-15) above, $Y^1$ is alkylene having 2 to 12 carbons or alkyleneoxy having 2 to 12 carbons, $Y^2$ is alkylene having 2 to 12 carbons or oxyalkylene having 2 to 12 carbons, $Y^3$ is alkylene having 2 to 12 carbons, $W^1$ is hydrogen or fluorine, and $R^1$ is a substituent represented by formula (a-4-1) described above.

Concrete examples of the compound (M2-1-1) to the compound (M2-1-15) are shown below. In the following concrete examples, n and m are each independently an integer from 2 to 12.

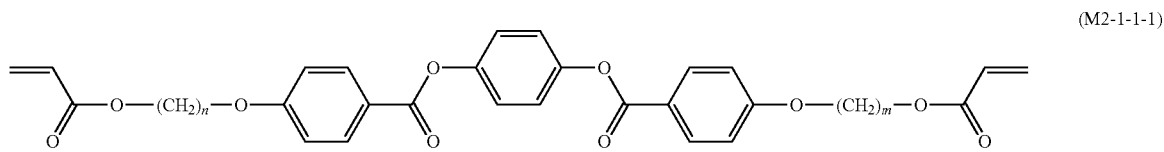
(M2-1-1-1)

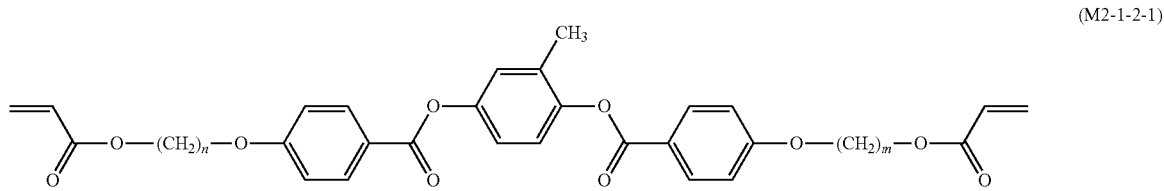
(M2-1-2-1)

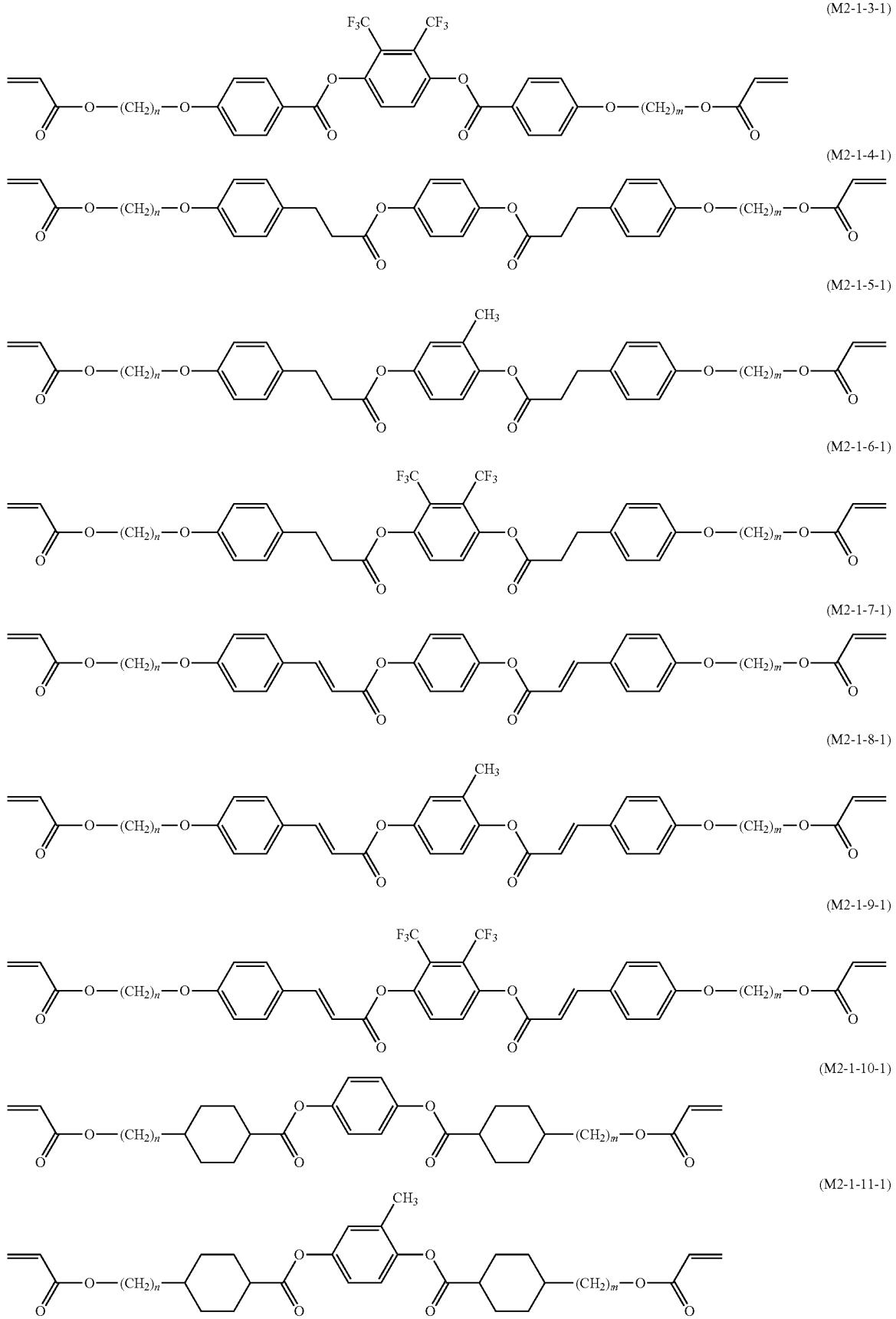

-continued
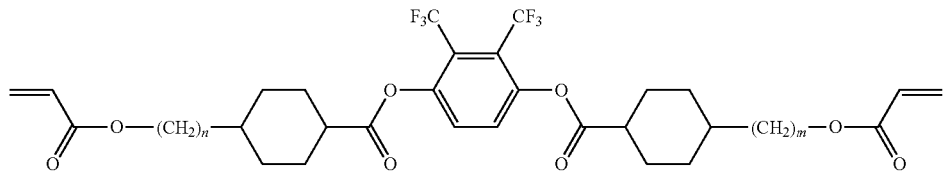
(M2-1-12-1)
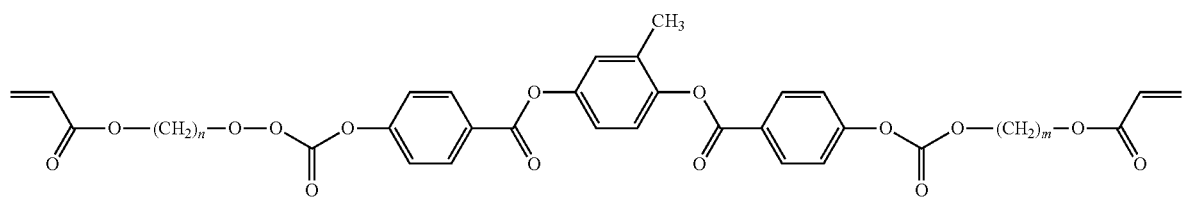
(M2-1-13-1)
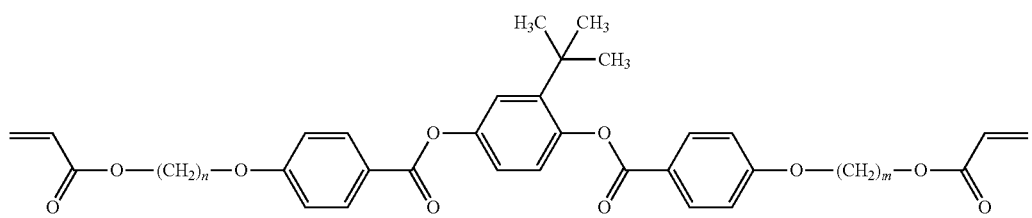
(M2-1-14-1)
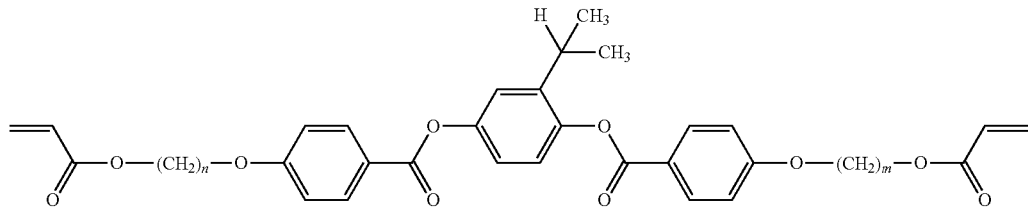
(M2-1-15-1)
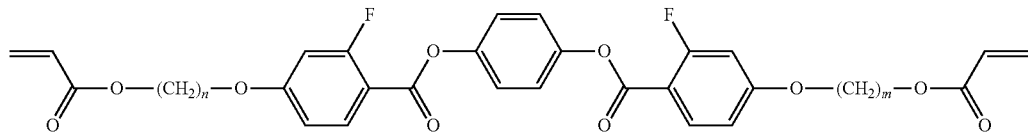
(M2-1-16-1)
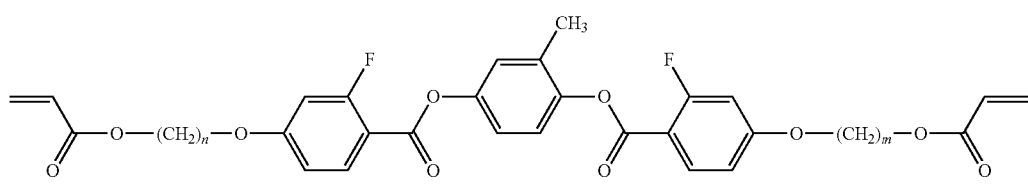
(M2-1-17-1)
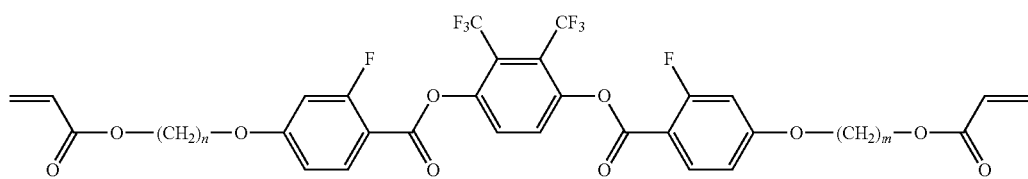
(M2-1-18-1)

Desirable examples of the compound (M2-2) are shown below.
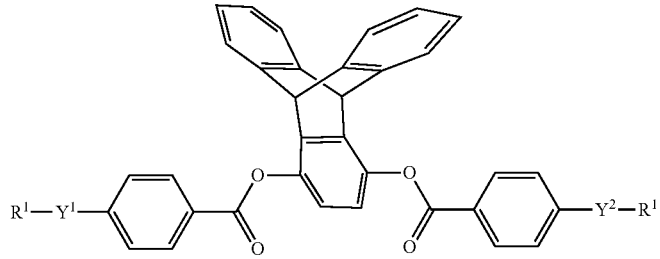
(M2-2-1)
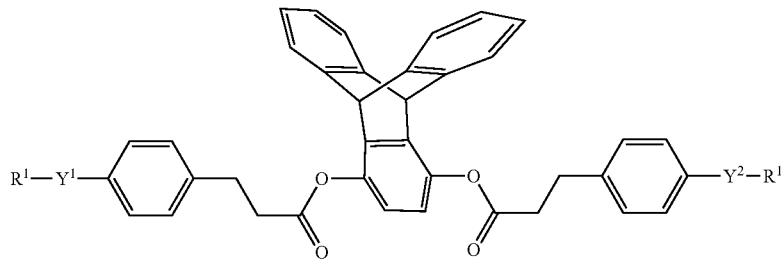
(M2-2-2)
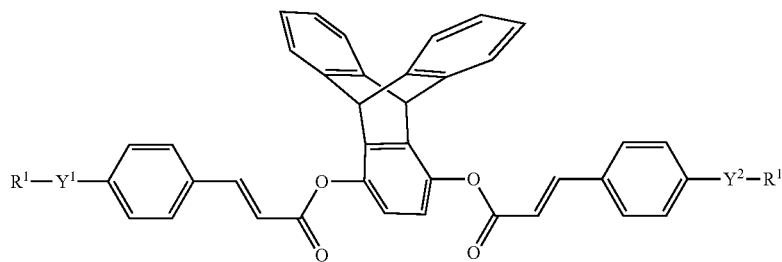
(M2-2-3)
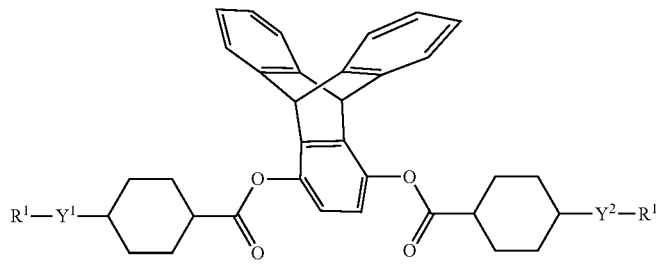
(M2-2-4)
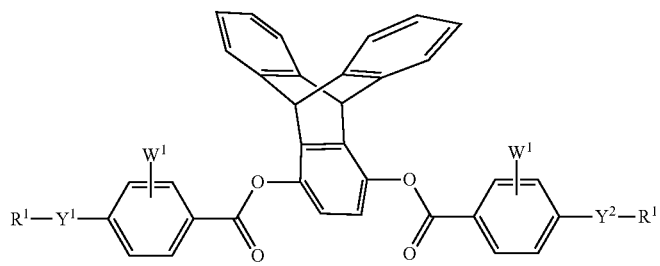
(M2-2-5)

In these formulas, $Y^1$ is alkylene having 2 to 12 carbons or alkyleneoxy having 2 to 12 carbons, $Y^2$ is alkylene having 2 to 12 carbons or oxyalkylene having 2 to 12 carbons, $W^1$ is hydrogen or fluorine, and $R^1$ is a substituent represented by formula (a-4-1) described above.

Concrete examples of the compound (M2-2-1) to the compound (M2-2-5) are shown below. In the following concrete examples, n and m are each independently an integer from 2 to 12.

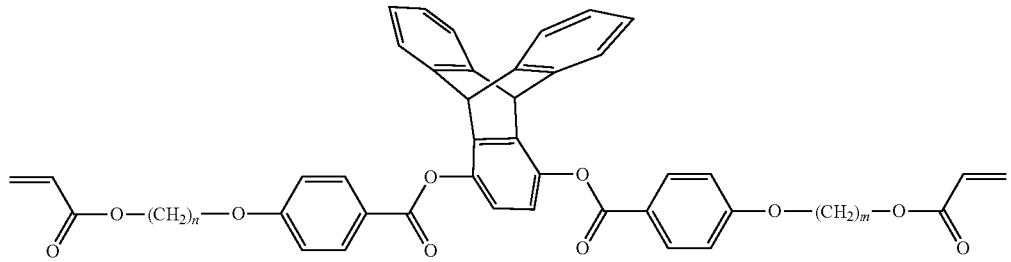

(M2-2-1)

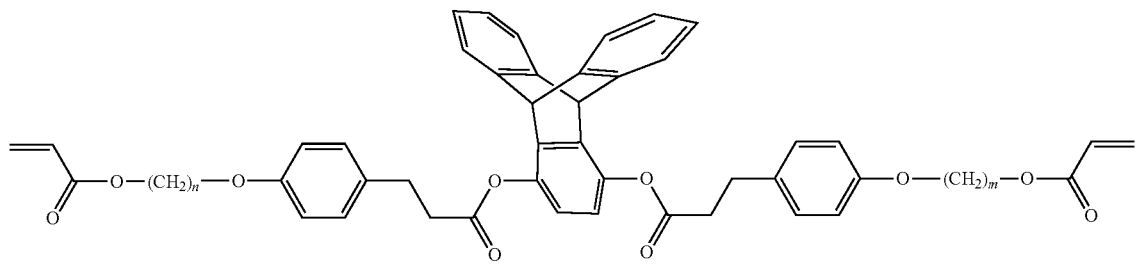

(M2-2-2-1)

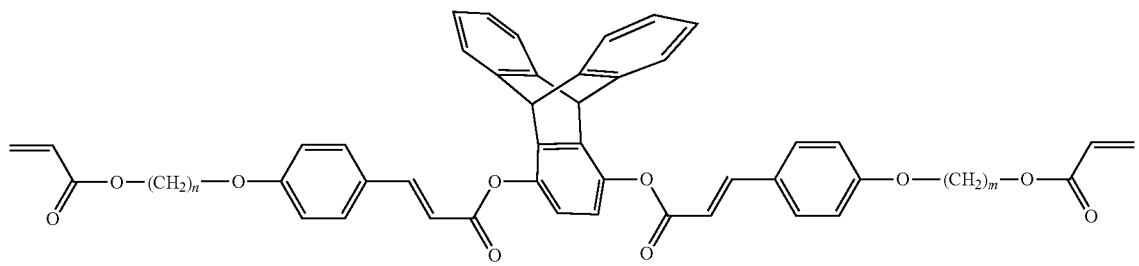

(M2-2-3-1)

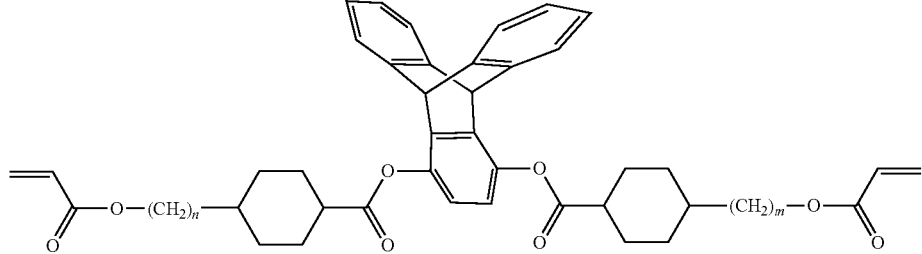

(M2-2-4-1)

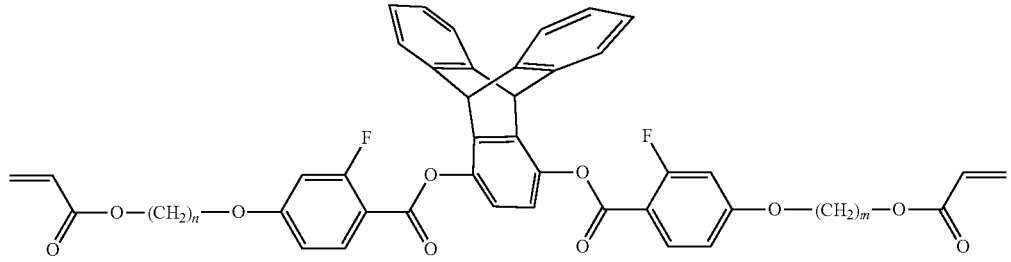

(M2-2-5-1)

Desirable examples of the compound (M2-3) are shown below.

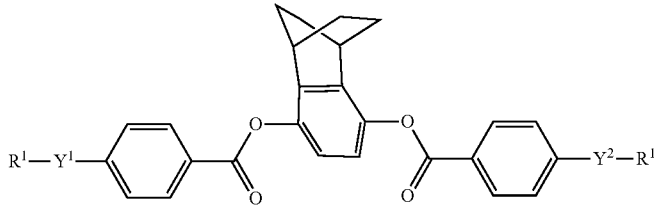
(M2-3-1)

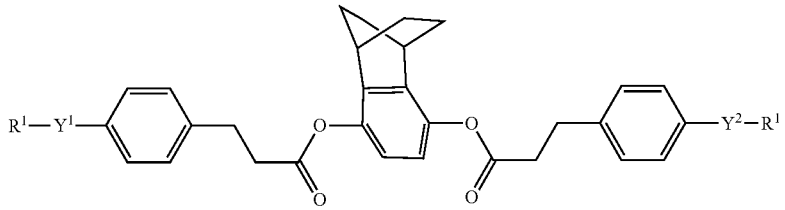
(M2-3-2)

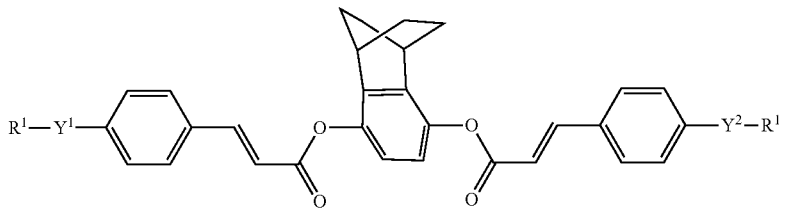
(M2-3-3)

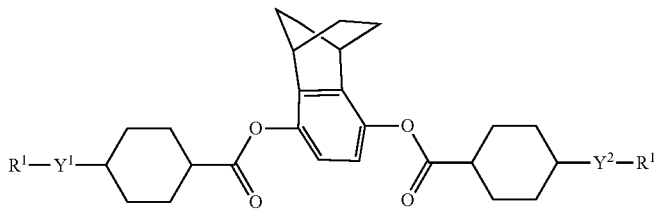
(M2-3-4)

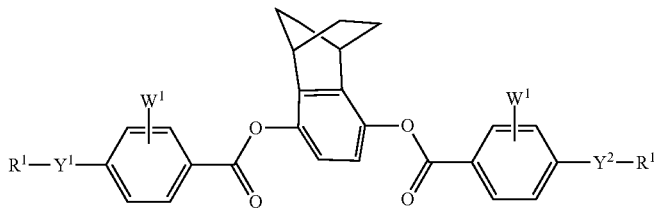
(M2-3-5)

In these formulas, $Y^1$ is alkylene having 2 to 12 carbons or alkyleneoxy having 2 to 12 carbons, $Y^2$ is alkylene having 2 to 12 carbons or oxyalkylene having 2 to 12 carbons, $W^1$ is hydrogen or fluorine, and $R^1$ is a substituent represented by formula (a-4-1) described above.

Concrete examples of the compound (M2-3-1) to the compound (M2-3-5) are shown below. In the following concrete examples, n and m are each independently an integer from 2 to 12.

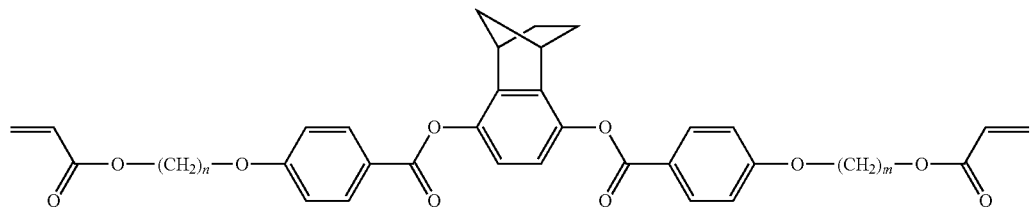
(M2-3-1-1)

(M2-3-2-1)
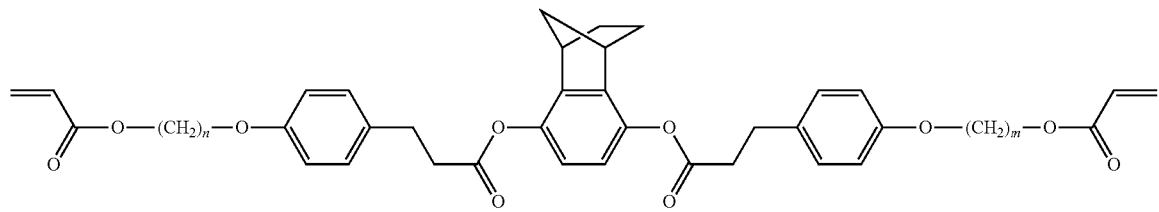
(M2-3-3-1)
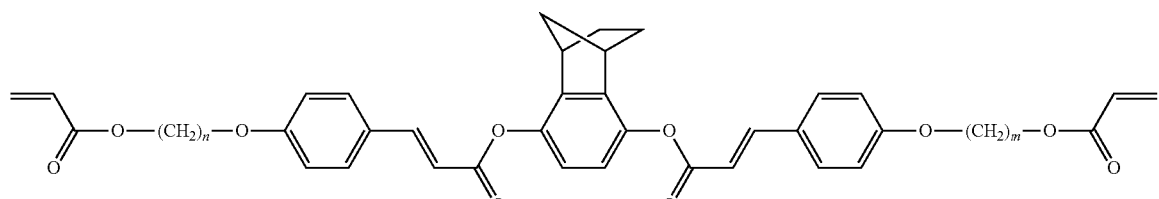
(M2-3-4-1)
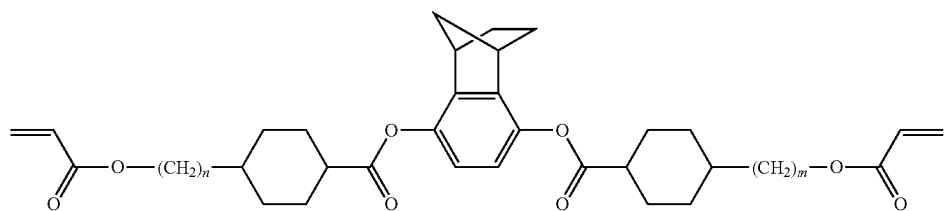
(M2-3-5-1)
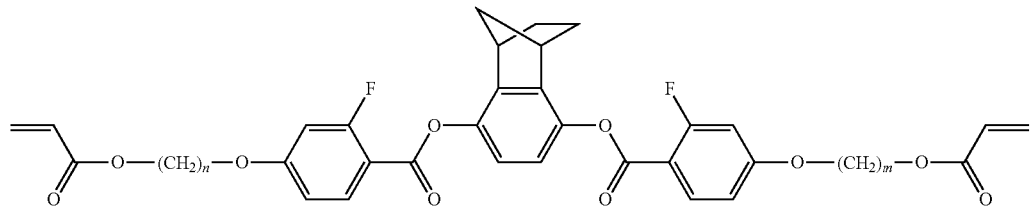
Desirable examples of the compound (M2-4) are shown below.
(M2-4-1)
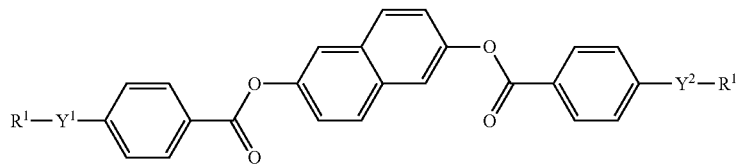
(M2-4-2)
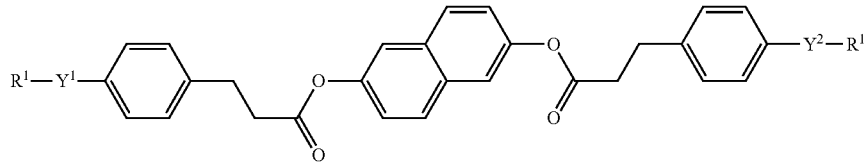
(M2-4-3)
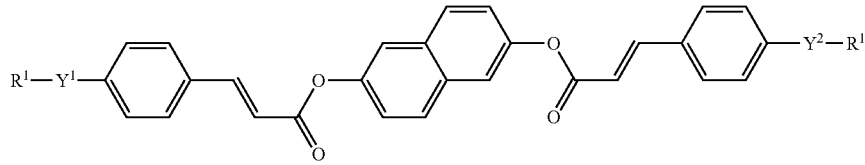

(M2-4-4)

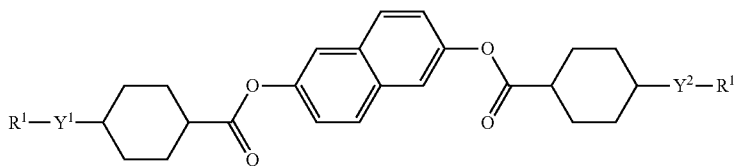

(M2-4-5)

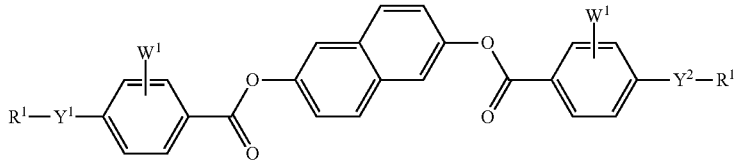

In these formulas, $Y^1$ is alkylene having 2 to 12 carbons or alkyleneoxy having 2 to 12 carbons, $Y^2$ is alkylene having 2 to 12 carbons or oxyalkylene having 2 to 12 carbons, $W^1$ is hydrogen or fluorine, and $R^1$ is a substituent represented by formula (a-4-1) described above.

Concrete examples of the compound (M2-4-1) to the compound (M2-4-5) are shown below. In the following concrete examples, n and m are each independently an integer from 2 to 12.

(M2-4-1-1)

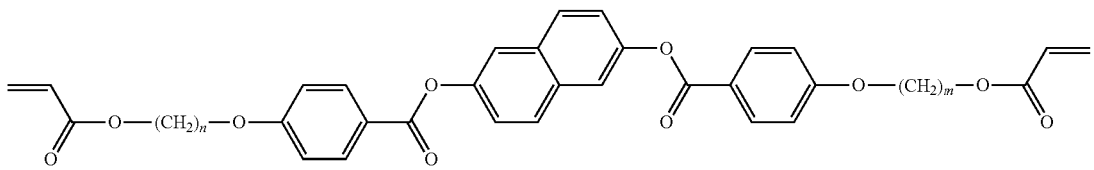

(M2-4-2-1)

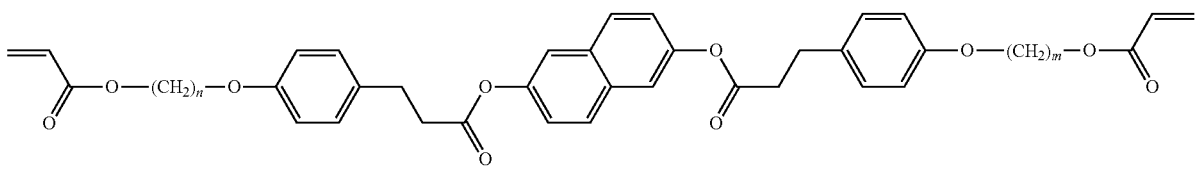

(M2-4-3-1)

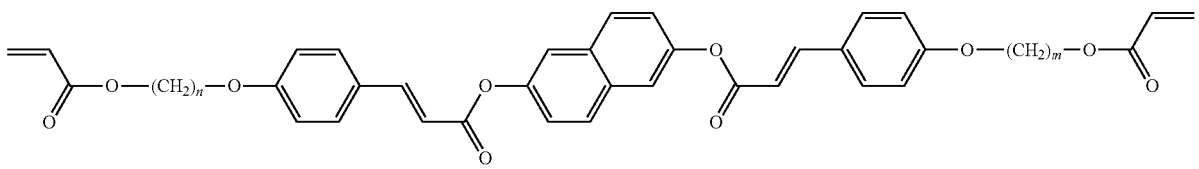

(M2-4-4-1)

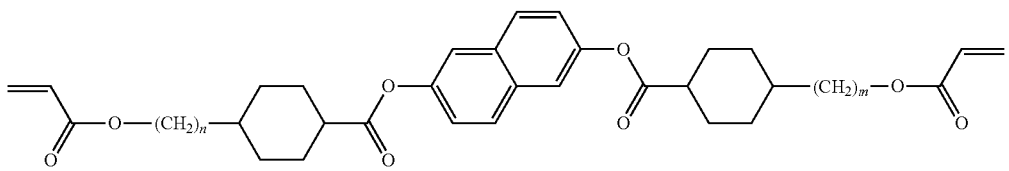

(M2-4-5-1)

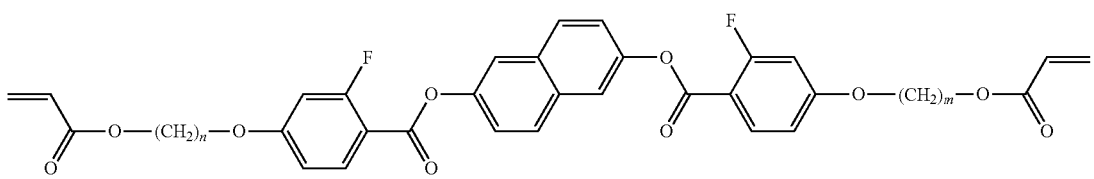

Desirable examples of the compound (M2-5) are shown below.
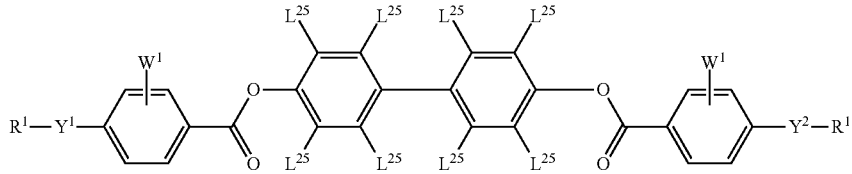 (M2-5-1)
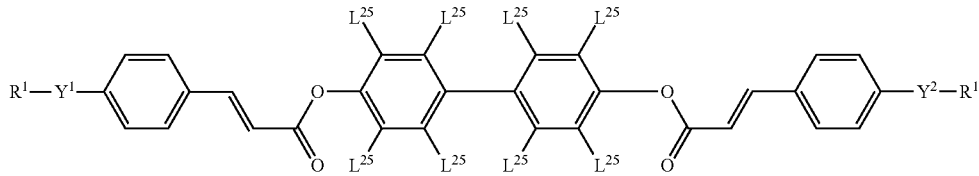 (M2-5-2)
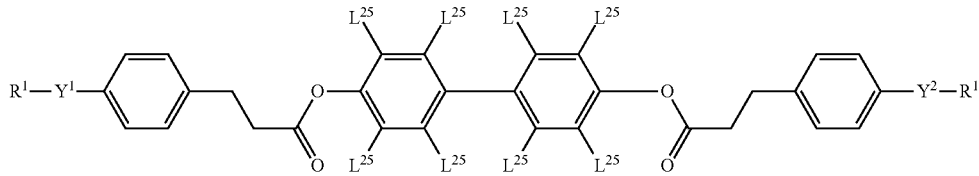 (M2-5-3)
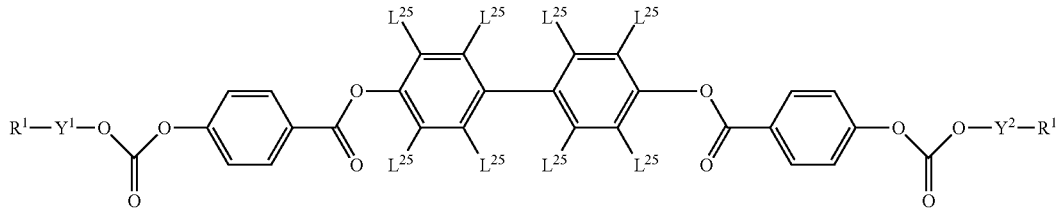 (M2-5-4)
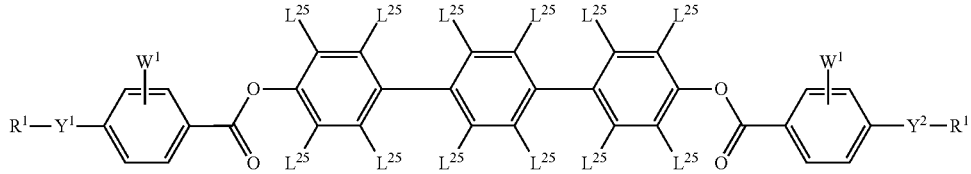 (M2-5-5)
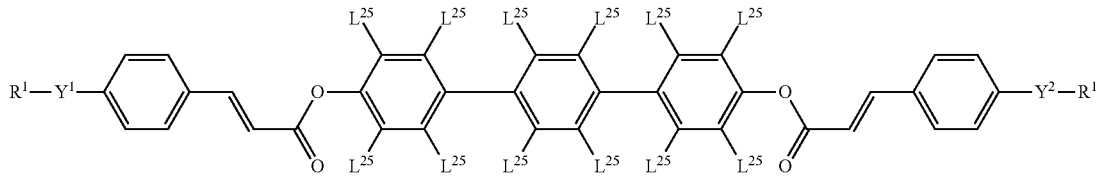 (M2-5-6)
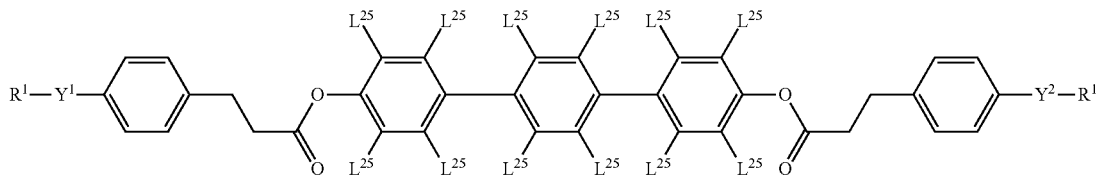 (M2-5-7)

(M2-5-8)

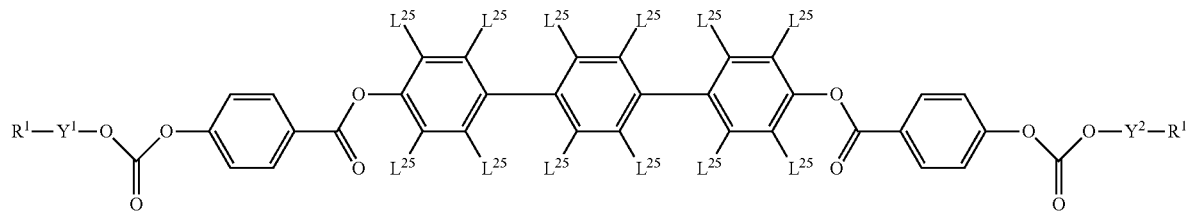

In these formulas, $Y^1$ is alkylene having 2 to 12 carbons or alkyleneoxy having 2 to 12 carbons, $Y^2$ is alkylene having 2 to 12 carbons or oxyalkylene having 2 to 12 carbons, $W^1$ is hydrogen or fluorine, $L^{25}$ は hydrogen, fluorine, methyl or methoxy, and $R^1$ is a substituent represented by formula (a-4-1) described above.

Concrete examples of the compound (M2-5-1) to the compound (M2-5-8) are shown below. In the following concrete examples, n and m are each independently an integer from 2 to 12.

(M2-5-1-1)

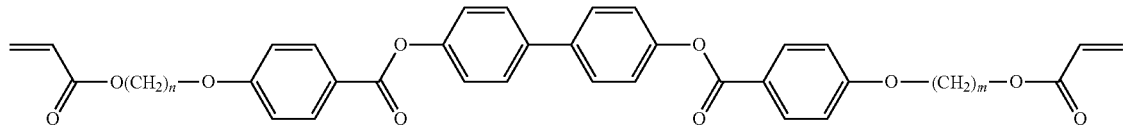

(M2-5-1-2)

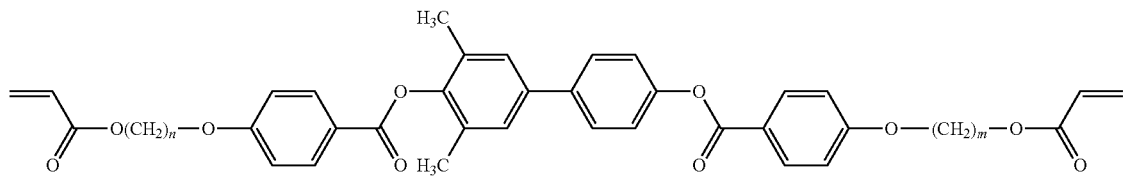

(M2-5-1-3)

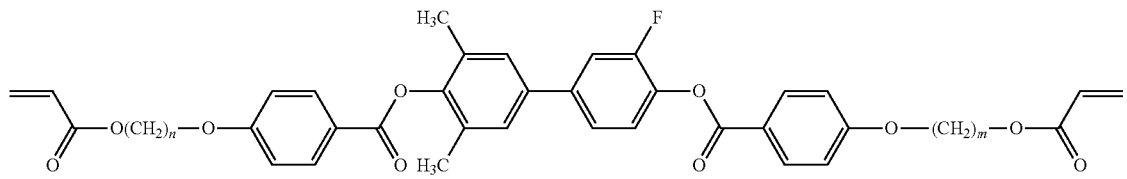

(M2-5-1-4)

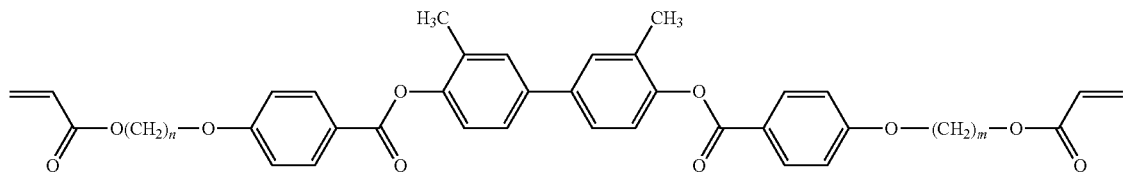

(M2-5-1-5)

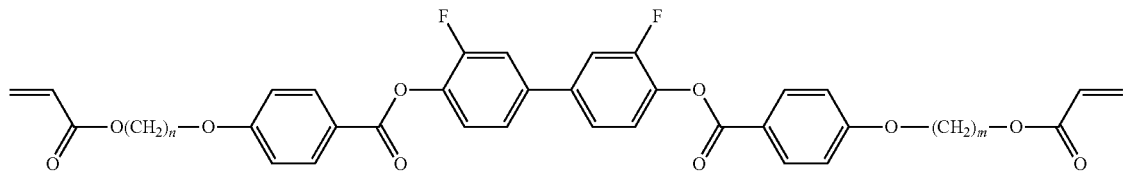

-continued
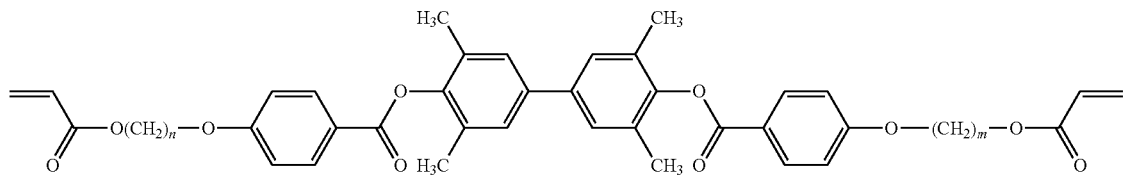
(M2-5-1-6)
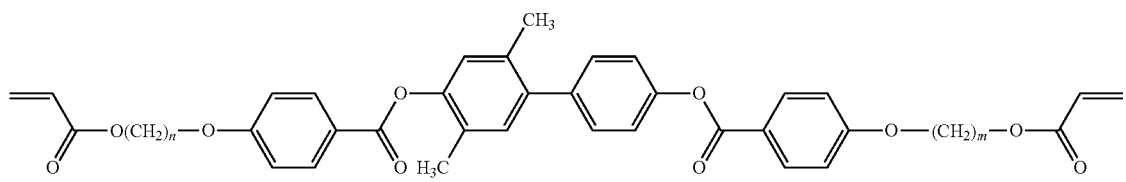
(M2-5-1-7)
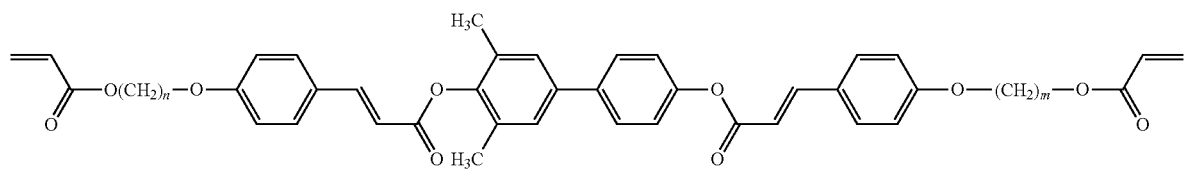
(M2-5-2-1)
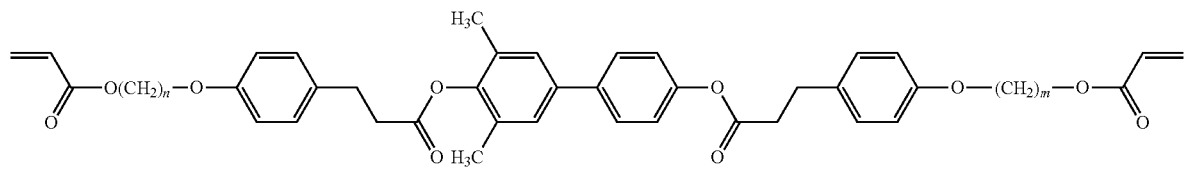
(M2-5-3-1)
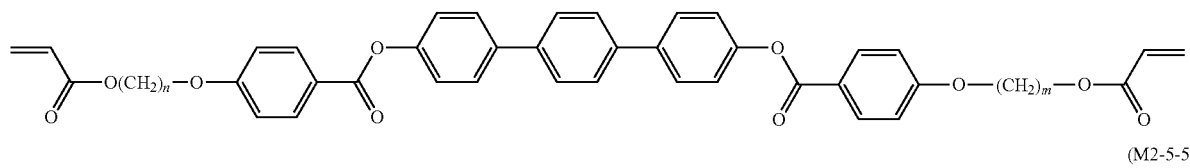
(M2-5-5-1)
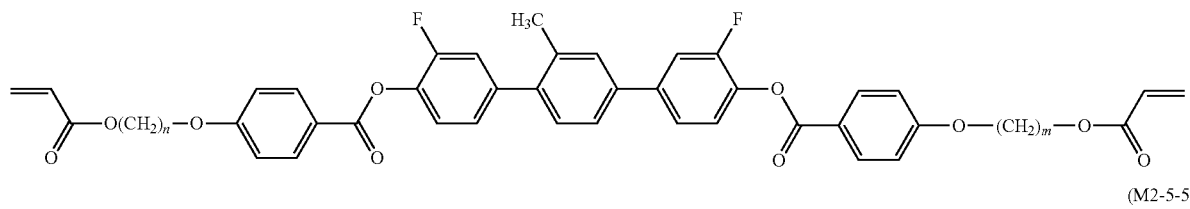
(M2-5-5-2)
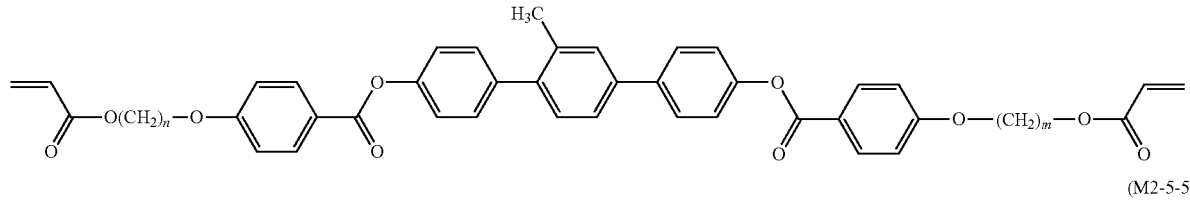
(M2-5-5-3)
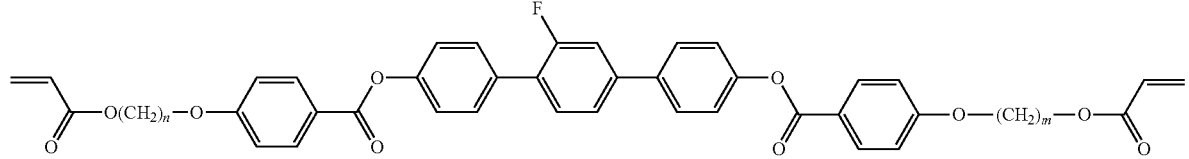
(M2-5-5-4)

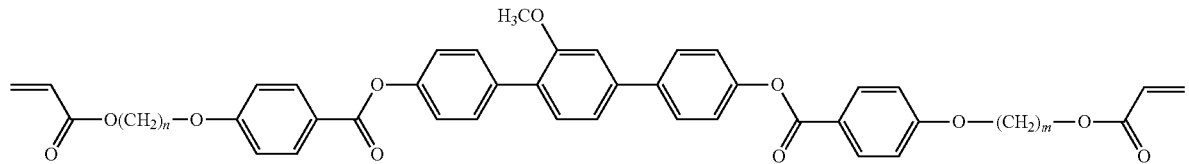

Desirable examples of the compound (M3) are shown below:

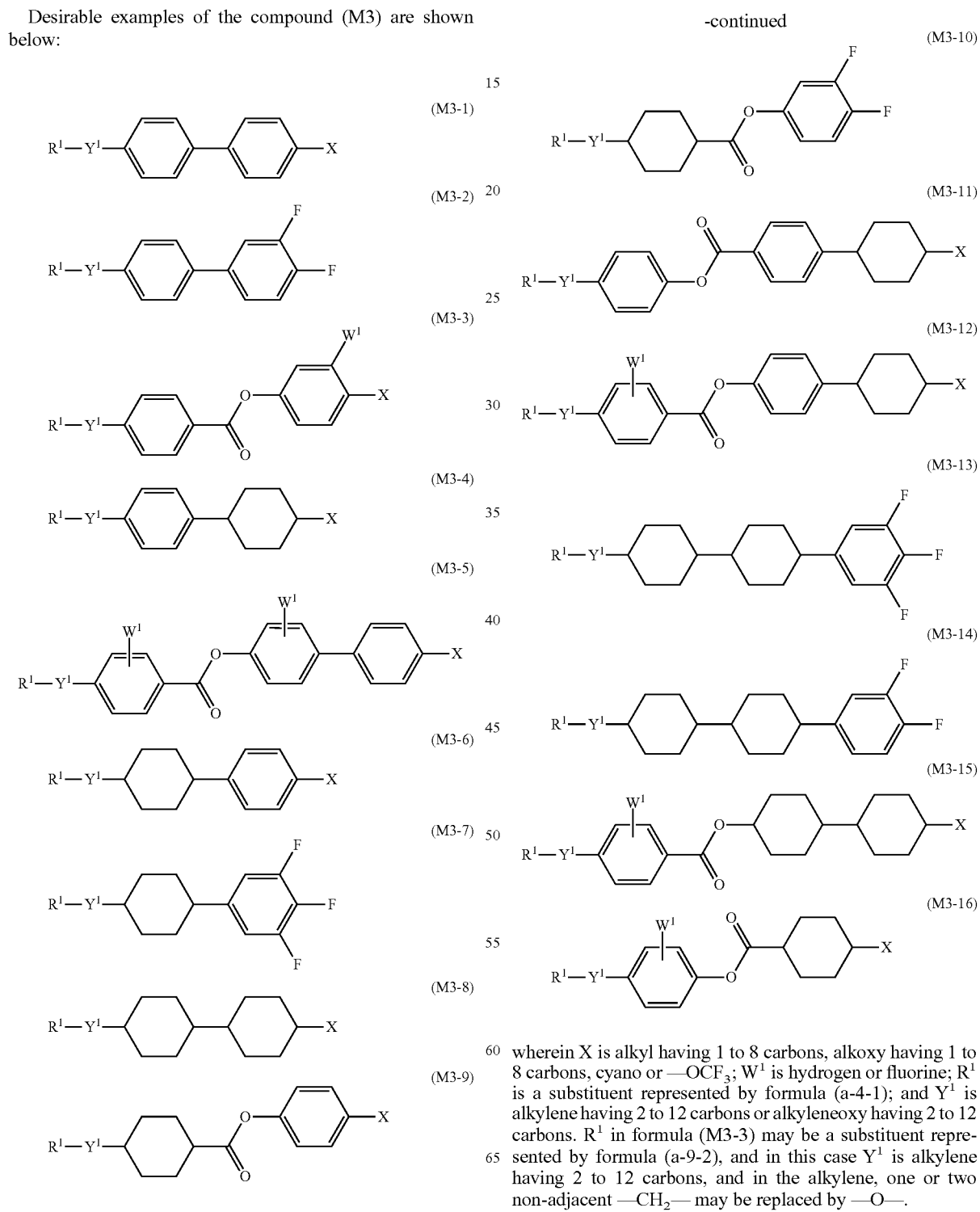

wherein X is alkyl having 1 to 8 carbons, alkoxy having 1 to 8 carbons, cyano or —OCF$_3$; W$^1$ is hydrogen or fluorine; R$^1$ is a substituent represented by formula (a-4-1); and Y$^1$ is alkylene having 2 to 12 carbons or alkyleneoxy having 2 to 12 carbons. R$^1$ in formula (M3-3) may be a substituent represented by formula (a-9-2), and in this case Y$^1$ is alkylene having 2 to 12 carbons, and in the alkylene, one or two non-adjacent —CH$_2$— may be replaced by —O—.

Concrete examples of the compound (M3-1) to the compound (M3-16) where $R^1$ is a substituent represented by formula (a-4-1) are shown below. In the following concrete examples, n is independently an integer from 2 to 12.
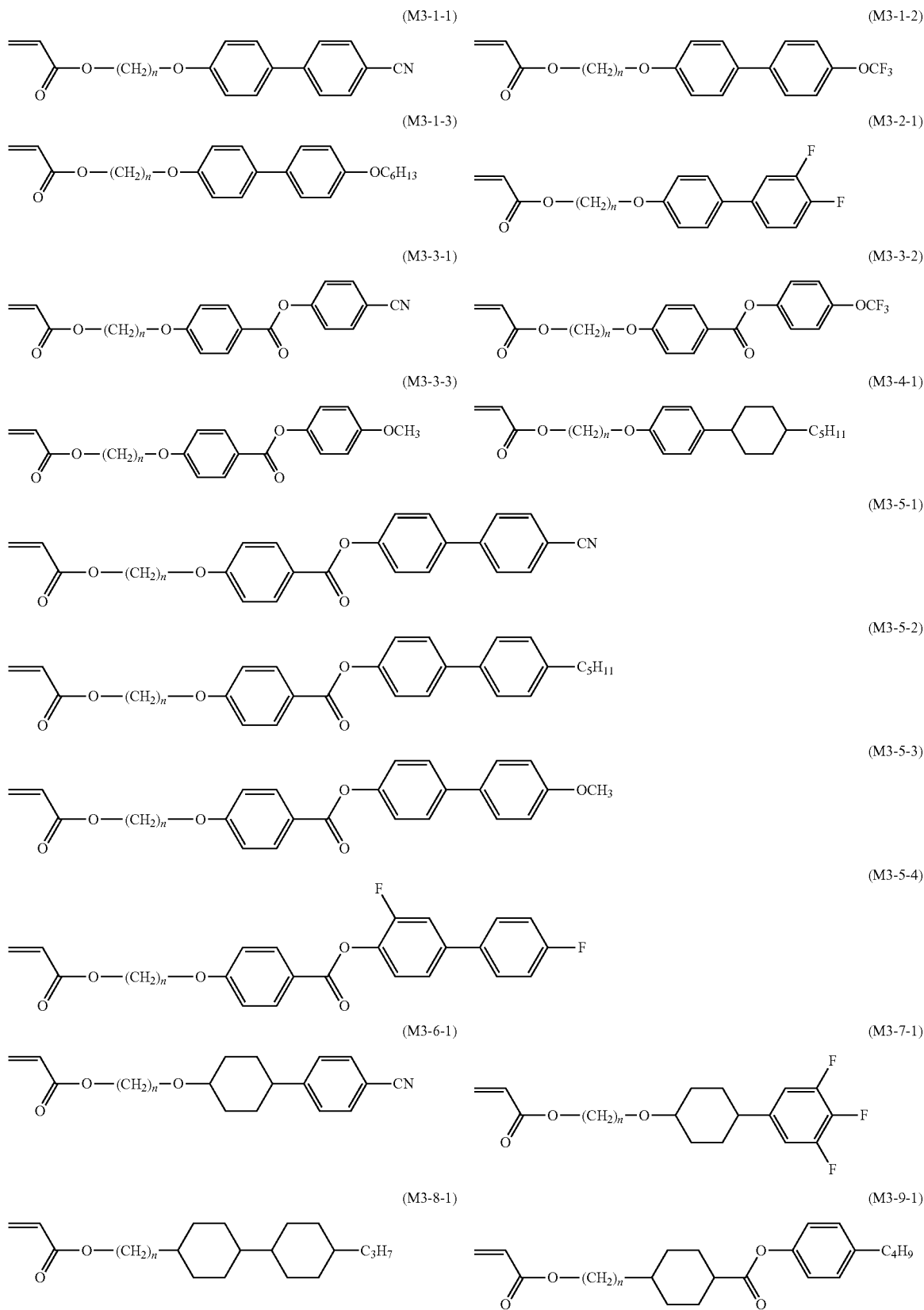

-continued
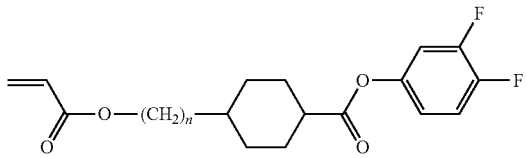
(M3-10-1)
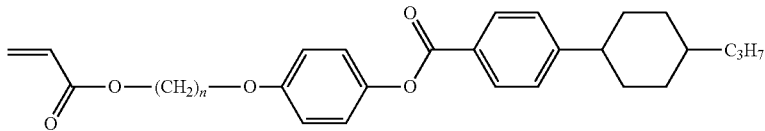
(M3-11-1)
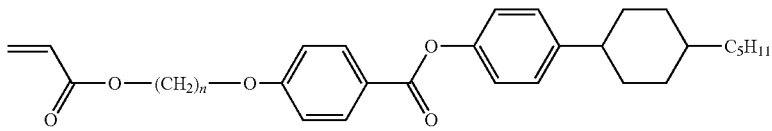
(M3-12-1)
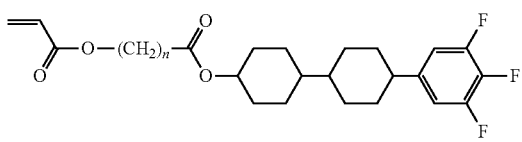
(M3-13-1)
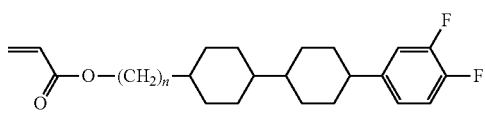
(M3-14-1)
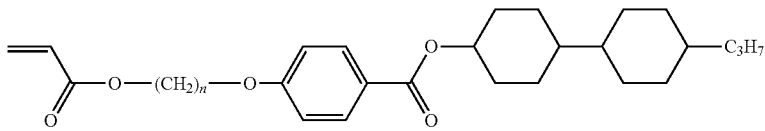
(M3-15-1)
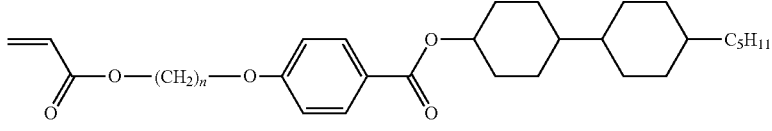
(M3-15-2)
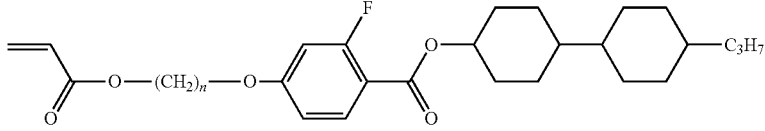
(M3-15-3)
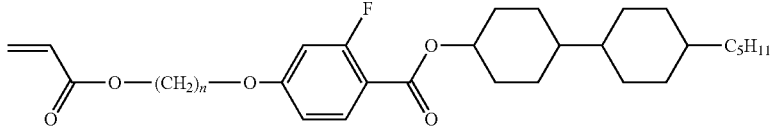
(M3-15-4)
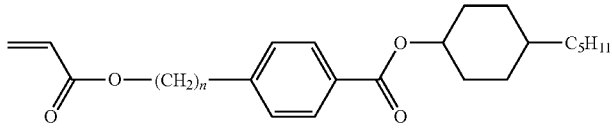
(M3-16-1)

Concrete examples of the compound (M3-3) where $R^1$ is a substituent represented by formula (a-9-2) are shown below. In the following concrete examples, n is independently an integer from 2 to 12.

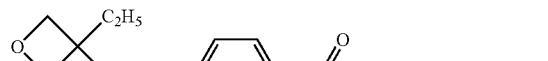
(M3-3-4)

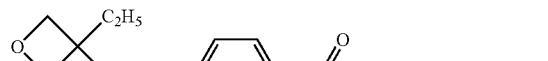
(M3-3-5)

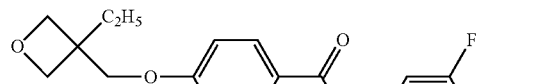
(M3-3-6)

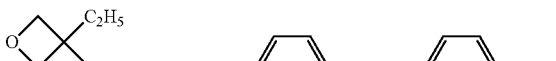
(M3-3-7)

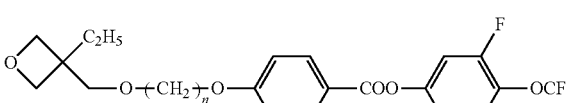

Desirable examples of the compound (M4) are shown below:

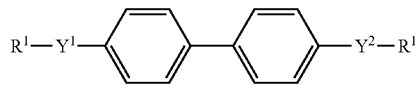
(M4-1)

(M4-2)

(M4-3)

(M4-4)

(M4-5)

wherein $R^1$ is a substituent represented by formula (a-4-1); $Y^1$ is alkylene having 2 to 12 carbons or alkyleneoxy having 2 to 12 carbons; and $Y^2$ is alkylene having 2 to 12 carbons or oxyalkylene having 2 to 12 carbons. $R^1$ in formula (M4-2) may be a substituent represented by formula (a-5-1), and in this case $Y^1$ is alkylene having 2 to 12 carbons or alkyleneoxy having 2 to 12 carbons, $Y^2$ is alkylene having 2 to 12 carbons or oxyalkylene having 2 to 12 carbons.

Concrete examples of the compound (M4-1) to the compound (M4-5) where $R^1$ is a substituent represented by formula (a-4-1) are shown below. In the following concrete examples, n and m are each independently an integer from 2 to 12.

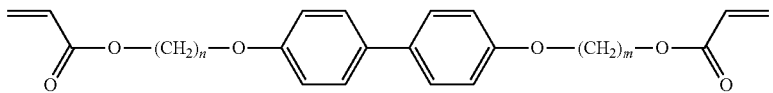
(M4-1-1)

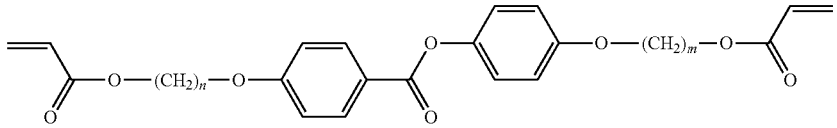
(M4-2-1)

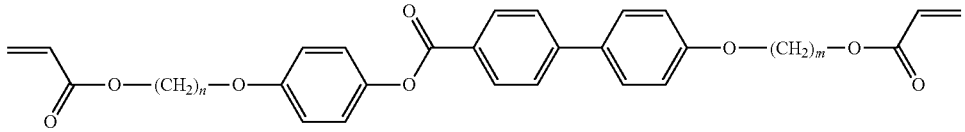
(M4-3-1)

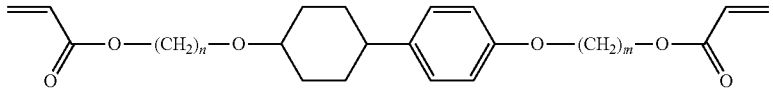
(M4-4-1)

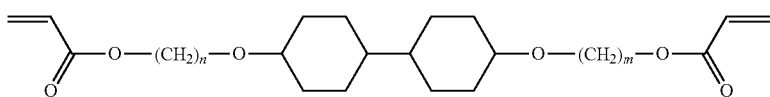
(M4-5-1)

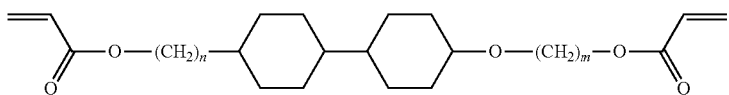
(M4-5-2)

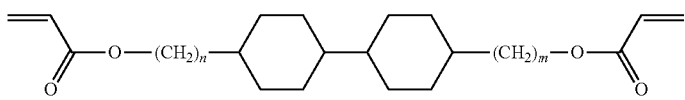
(M4-5-3)

Concrete examples of the compound (M4-2) where $P^1$ is a substituent represented by formula (a-5-1) are shown below. In the following concrete examples, n and m are each independently an integer from 2 to 12.

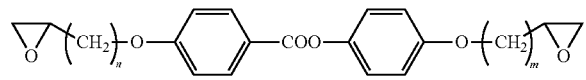
(M4-2-2)

The compound (M) can be prepared by means of a combination of techniques in synthetic organic chemistry. Methods for an introduction of objective terminal groups, rings and bonding groups to starting materials are described in books such as Houben-Wyle, Methods of Organic Chemistry, Georg Thieme Verlag, Stuttgart; Organic syntheses, John Wily & Sons, Inc.; Organic Reactions, John Wily & Sons Inc.; Comprehensive Organic Synthesis, Pergamon Press; and New Experimental Chemistry Course (Shin Jikken Kagaku Kouza, in Japanese title), Maruzen Co., LTD. Concrete methods for the preparation of the compound (M) are described in the following references. For the compound (M1-1-9) to the compound (M1-1-14) and the compound (M1-1-15) to the compound (M1-1-20), see JP 2005-060373 A; for the compound (M1-3-1) to the compound (M1-3-2), see WO2008/136265 A; for the compound (M2-1-1-1) and the compound (M2-1-2-1), see Makromol. Chem., 190, 3201-3215 (1998); for the compound (M2-1-3-1) and the compound (M2-1-9-1), see JP 2004-231638 A; for the compound (M2-1-3-1), see JP 2006-337565 A; for the compound (M2-1-13-1), see WO 97/000600 A; for the compound (M2-2-1-1), see JP 2006-111571 A; for the compound (M2-5), see JP 2008-239873 A; for the compound (M3-3-4) to (M3-3-7), see JP 2005-320317 A; and for the compound (M4-2-2), see Macromolecules, 26, 1244-1247 (1993).

The compound (M5) may further be added to a composition including a compound having a polymerizable group represented by formula (a-4-1) described above. The ratio of the compound (M5) is in the range of 0 to approximately 0.20 by weight based on the total weight of the compound (M1) to the compound (M4).

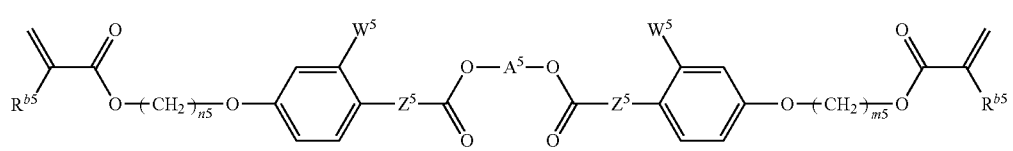
(M5)

In formula (M5), $R^{b5}$ is independently hydrogen or methyl, $W^5$ is independently hydrogen or fluorine, $Z^5$ is independently a single bond, —CH$_2$CH$_2$— or —CH=CH—, n5 and m5 are each independently an integer from 2 to 12, and $A^5$ is any one of formula (A5-1) to formula (A5-18).
(A5-1)
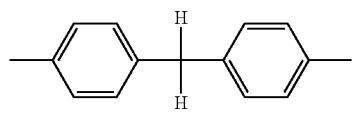
(A5-2)
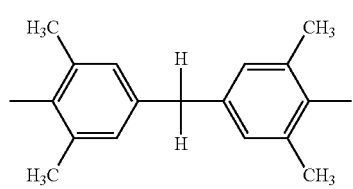
(A5-3)
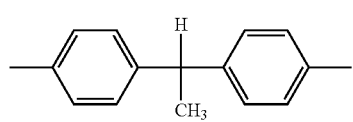
(A5-4)
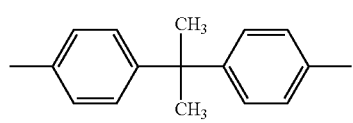
(A5-5)
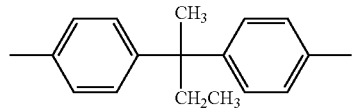
(A5-6)
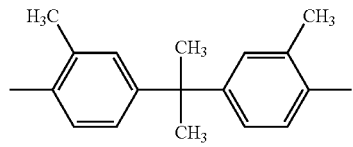
(A5-7)
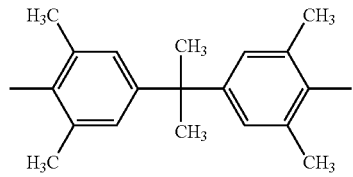
(A5-8)
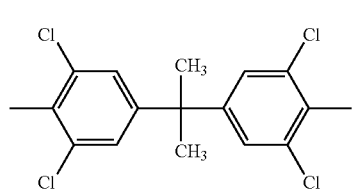
(A5-9)
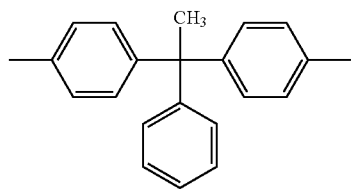
(A5-10)
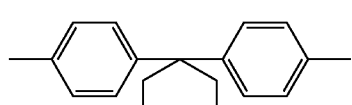
(A5-11)
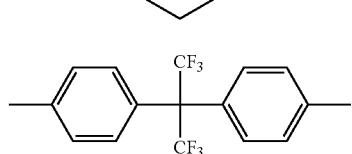
(A5-12)
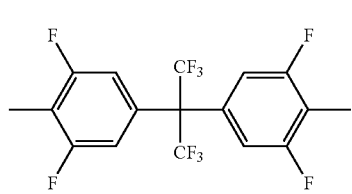
(A5-13)
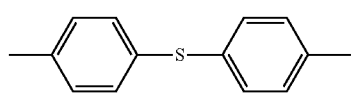
(A5-14)
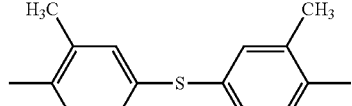
(A5-15)
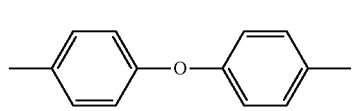
(A5-16)
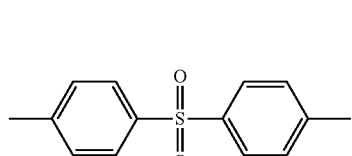
(A5-17)
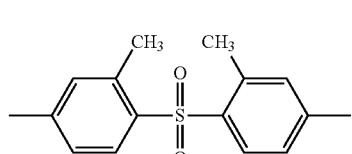
(A5-18)
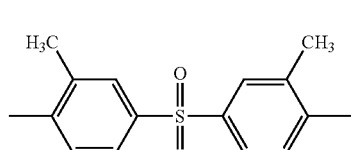
Desirable examples of the compound (M5) are shown below.

(M5-A5-10-1)
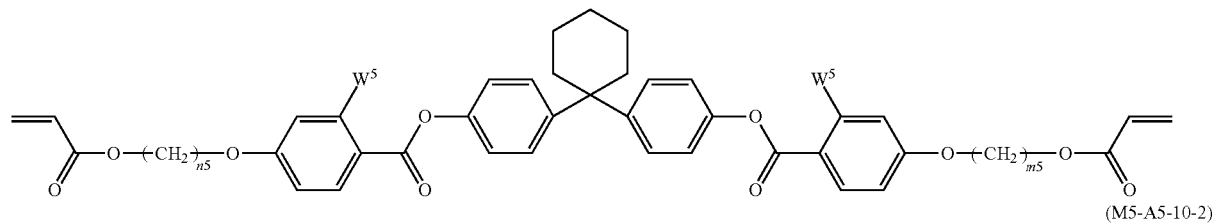
(M5-A5-10-2)
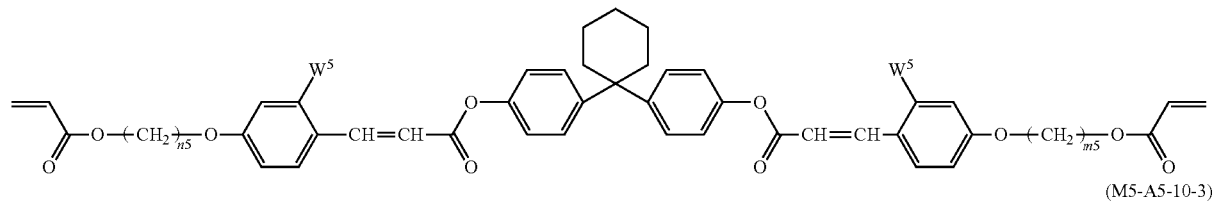
(M5-A5-10-3)
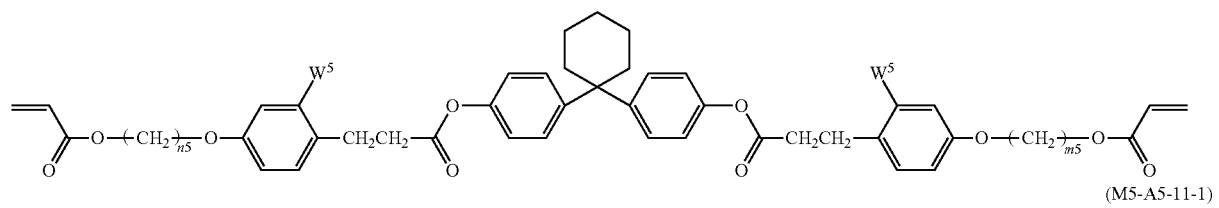
(M5-A5-11-1)
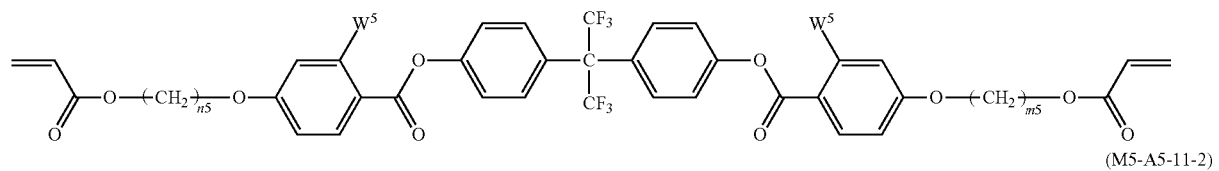
(M5-A5-11-2)
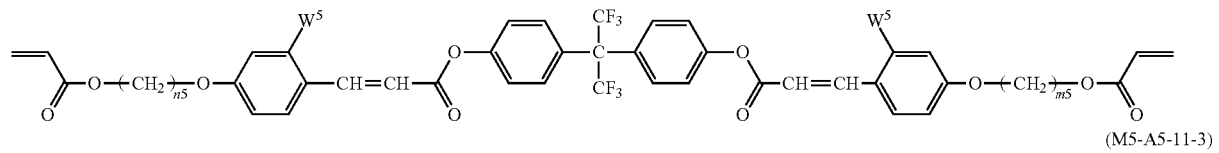
(M5-A5-11-3)
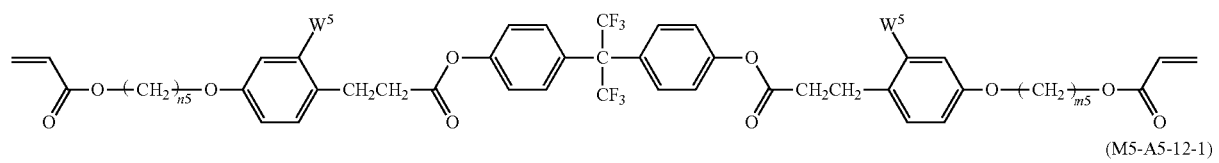
(M5-A5-12-1)
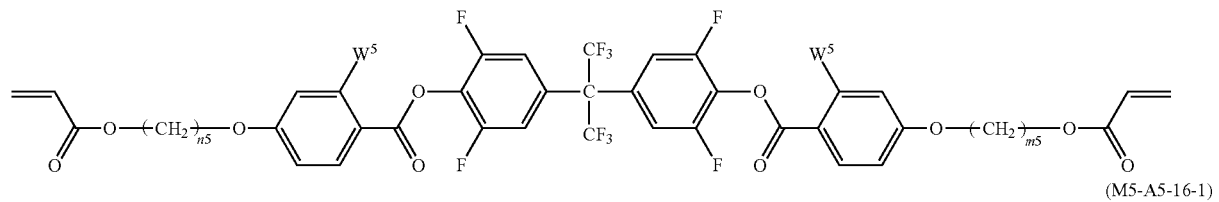
(M5-A5-16-1)
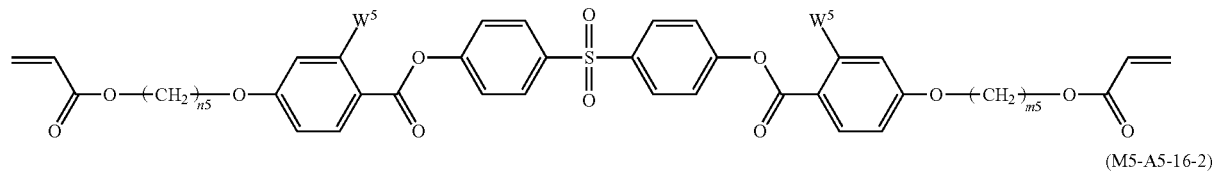
(M5-A5-16-2)
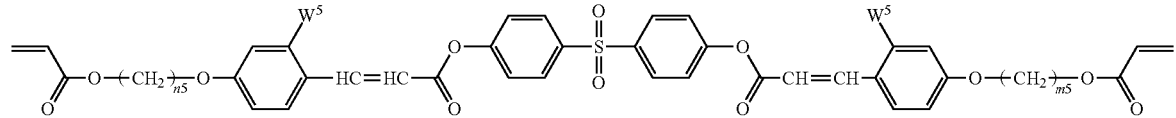

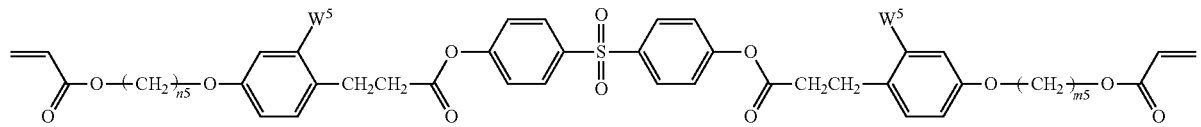

(M5A5-16-3)

The methods for the preparation of these compounds are described in JP 2007-016213 A and JP 2008-133344 A.

The polymerizable liquid crystal composition of the invention may include another polymerizable compound other than the compound (M) and the compound (M5). A compound that does not decrease the ability to form a coat and mechanical strength is desirable for another polymerizable compound. The compound is classified into a compound having no liquid crystallinity and a compound having liquid crystallinity.

Another polymerizable compound having no liquid crystallinity includes a vinyl derivative, a styrene derivative, a (meth)acrylic acid derivative, an oxirane derivative, an oxetane derivative, a sorbic acid derivative, a fumaric acid derivative and an itaconic acid derivative. These compounds are suitable to adjust the viscosity or the orientation of the composition, and have a large effect of making the thickness of the paint film uniform.

Examples of another polymerizable compound having no liquid crystallinity include a compound having one polymerizable group, a compound having two polymerizable groups and a polyfunctional compound having three or more polymerizable groups. The compound having one polymerizable group is exemplified in the paragraph 0097 of page 47 in JP 2008-266632 A, and the compound is suitable to adjust the viscosity, the melting point or the like.

The compound having two or more polymerizable groups is exemplified in the paragraph 0098 of page 48 in JP 2008-266632 A, and the compound is suitable to adjust mechanical strength of the polymer.

Epoxyacrylate resins may be used as another polymerizable compound. Concrete examples of the resins include phenol novolac-type epoxyacrylate resins cresol novolac-type epoxyacrylate resins, phenol novolac-type acid modified-epoxyacrylate resins, cresol novolac-type acid modified-epoxyacrylate resins and trisphenol methane-based epoxyacrylate resins.

Examples of epoxy resins include epoxy resins that can be derived from dihydric phenols, such as bisphenol A-type epoxy resins, bisphenol F-type epoxy resins, bisphenol S-type epoxy resins, bisphenol AD-type epoxy resins, resorcinol-type epoxy resins, hydroquinone-type epoxy resins, catechol-type epoxy resins, dihydroxynaphthalene-type epoxy resins, biphenyl-type epoxy resins and tetramethylbiphenyl-type epoxy resins. Examples of the epoxy resins include epoxy resins that can be derived from trihydric or polyhydric phenols, such as phenol novolac-type epoxy resins, cresol novolac-type epoxy resins, triphenylmethane-type epoxy resins, tetraphenylethane-type epoxy resins, dicyclopentadiene-phenol modified epoxy resins, phenol aralkyl-type epoxy resins, biphenyl aralkyl-type epoxy resins, naphthol novolac-type epoxy resins, naphthol aralkyl-type epoxy resins, naphthol-phenol cocondensated novolac-type epoxy resins, naphthol-cresol cocondensated novolac-type epoxy resins, aromatic hydrocarbon formaldehyde resin-modified phenol resin-type epoxy resins and biphenyl-modified novolac-type epoxy resins. Additional examples of the epoxy resins include tetrabromobisphenol A-type epoxy resins, brominated phenol novolac-type epoxy resins, polycarboxylic acid polyglycidyl ester, polyol polyglycidyl ether, aliphatic acid-type epoxy resins, alicyclic epoxy resins, glycidylamine-type epoxy resins, triphenolmethane-type epoxy resins and dihydroxybenzene-type epoxy resins. These epoxy resins may be solely used or two or more epoxy resins may be mixed.

An epoxy-based compound may be used as another polymerizable compound. The epoxy-based compound is exemplified in the paragraph 0101 of page 49 in JP 2008-266632 A, and the compound is suitable to adjust mechanical strength of the polymer.

The following polymerizable compound having a bisphenol moiety may be used as another polymerizable compound. The compound is suitable to support the ability to form a coat of the polymer or the uniform orientation of polymerizable liquid crystals.

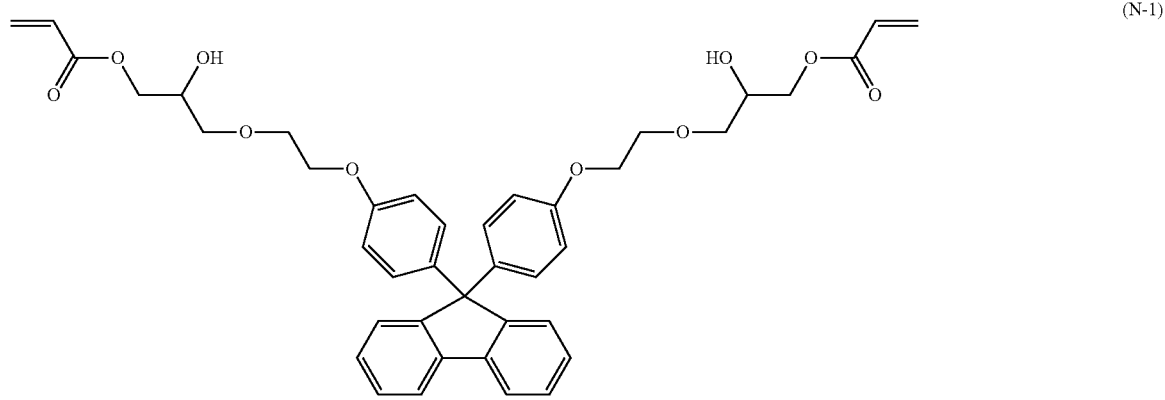

(N-1)

(N-2)
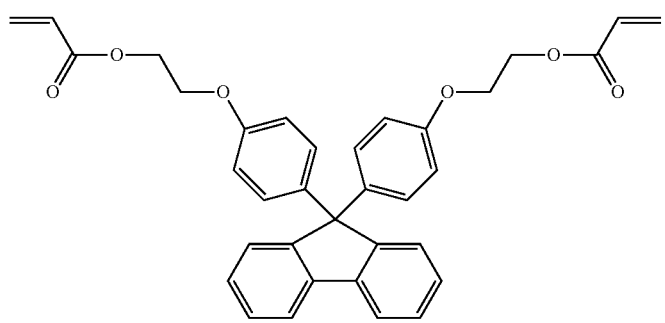
(N-3)
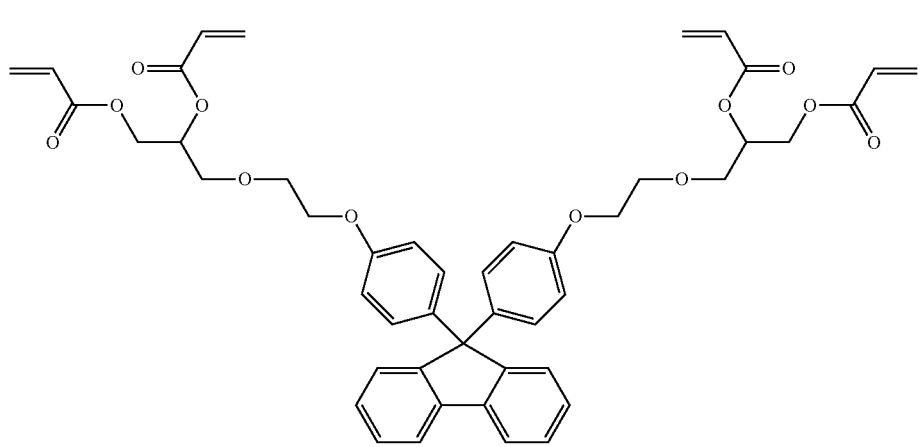
(N-4)
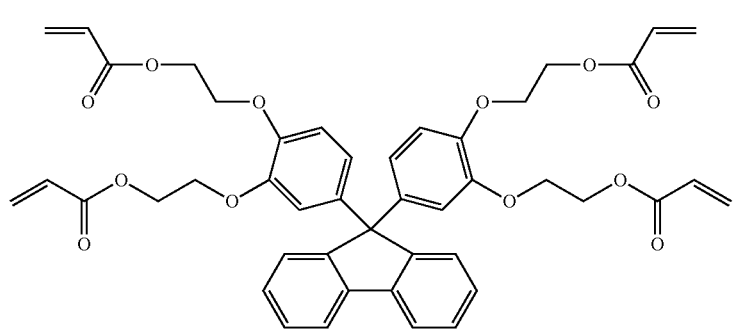
(N-5)
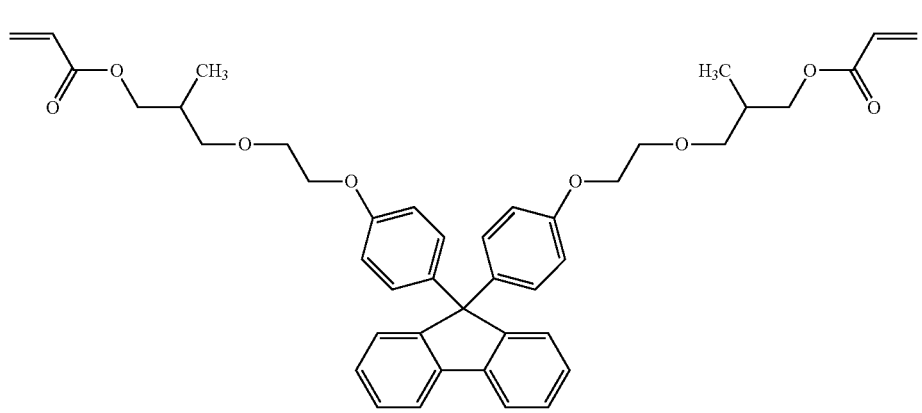

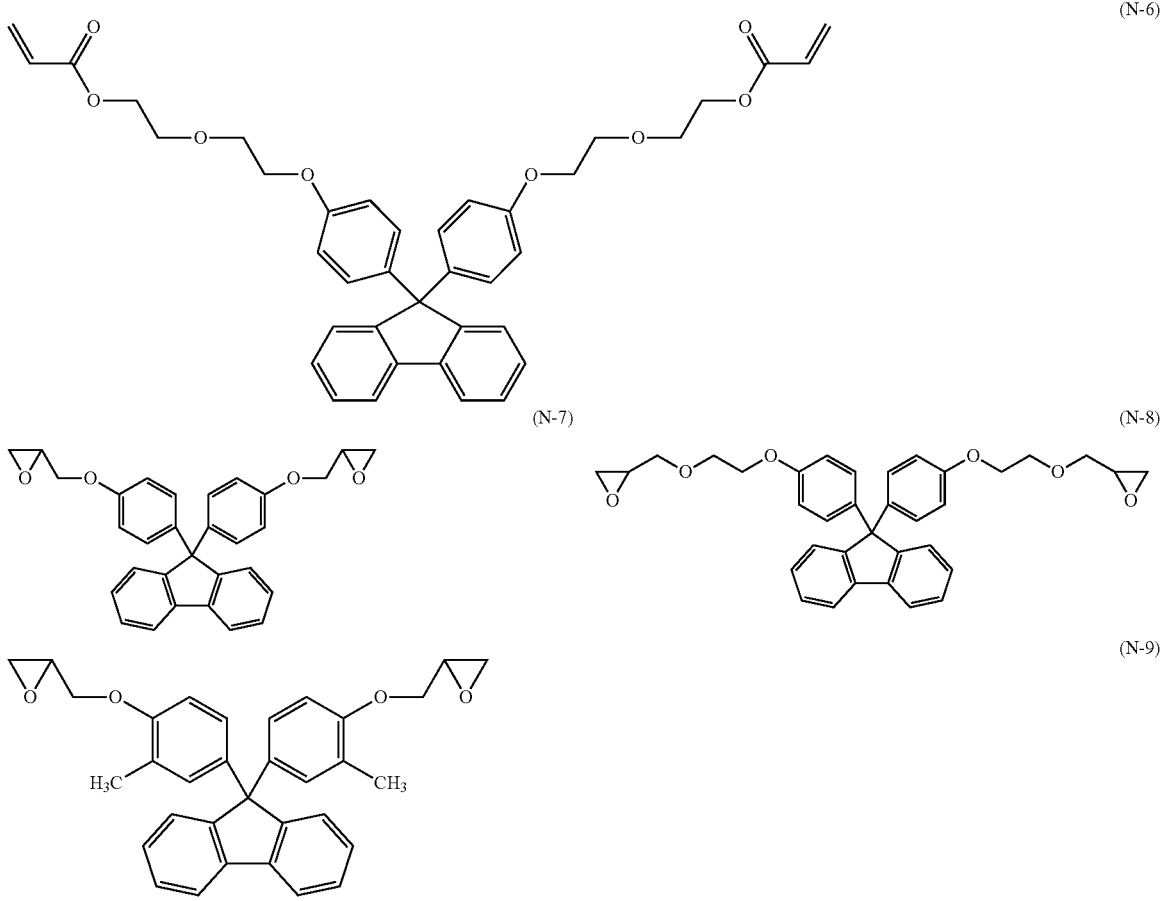

The methods for the preparation of the above compounds are described in JP 2002-348357 A, JP 2005-041925 A, JP 2005-266739 A and so forth. A commercial product including the compound (N-1), the compound (N-7), the compound (N-8) or the compound (N-9) includes ONF-1, Oncoat EX-1010, Oncoat EX-1020 and Oncoat EX-1040, those of which are available from Osaka Gas Chemicals Co., Ltd. These commercial products may be used.

The polymerizable liquid crystal composition may include a liquid crystal compound having no polymerizable groups. Examples of such a non-polymerizable liquid crystal compound are described in LiqCryst (LCI Publisher GmbH, Hamburg, Germany) that are databases of liquid crystal compounds, and so forth. The polymerizable liquid crystal compound (M) has an excellent compatibility with another liquid crystal compound. Thus, a polymerizable liquid crystal composition including the liquid crystal compound can be used as a liquid crystal composition that is enclosed into a liquid crystal display element. Such polymerizable liquid crystal composition may further include an additive such as a dichroic dye. Polymerization of the polymerizable liquid crystal composition including the liquid crystal compound gives composite materials of the polymer of the polymerizable liquid crystal compound (M) and the liquid crystal compound.

The ratio of a liquid crystal compound having no polymerizable groups in the polymerizable liquid crystal composition is approximately 50% by weight or less, and preferably approximately 30% by weight or less, based on the total weight (100%) of the polymerizable liquid crystal compound (M) and another liquid crystal compound.

A liquid crystal compound having no polymerizable groups includes a compound represented by formula (A) described below.

In formula (A), the meanings of $A^4$ and n are the same with those in formula (M1) described above; $Z^A$ is independently a single bond or alkylene having 1 to 10 carbons, and in the alkylene, arbitrary —$CH_2$— may be replaced by —O—, —CO—, —COO—, —OCO—, —CH=CH—, —CF=CF— or —C≡C—, and arbitrary hydrogen may be replaced by halogen; $R^A$ is alkyl having 1 to 10 carbons, alkenyl having 2 to 10 carbons, alkoxy having 1 to 10 carbons, hydrogen, chlorine, fluorine, —CN, —$CF_3$ or —$OCF_3$. Concrete examples are as follows.

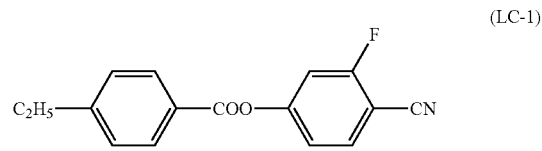

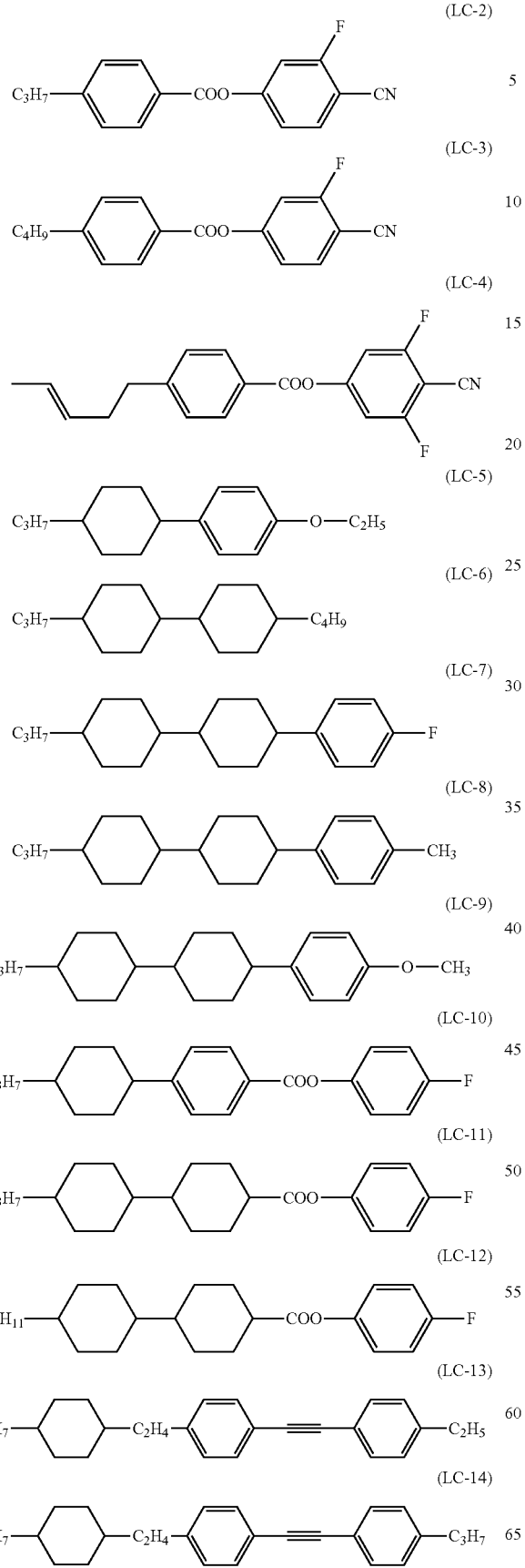
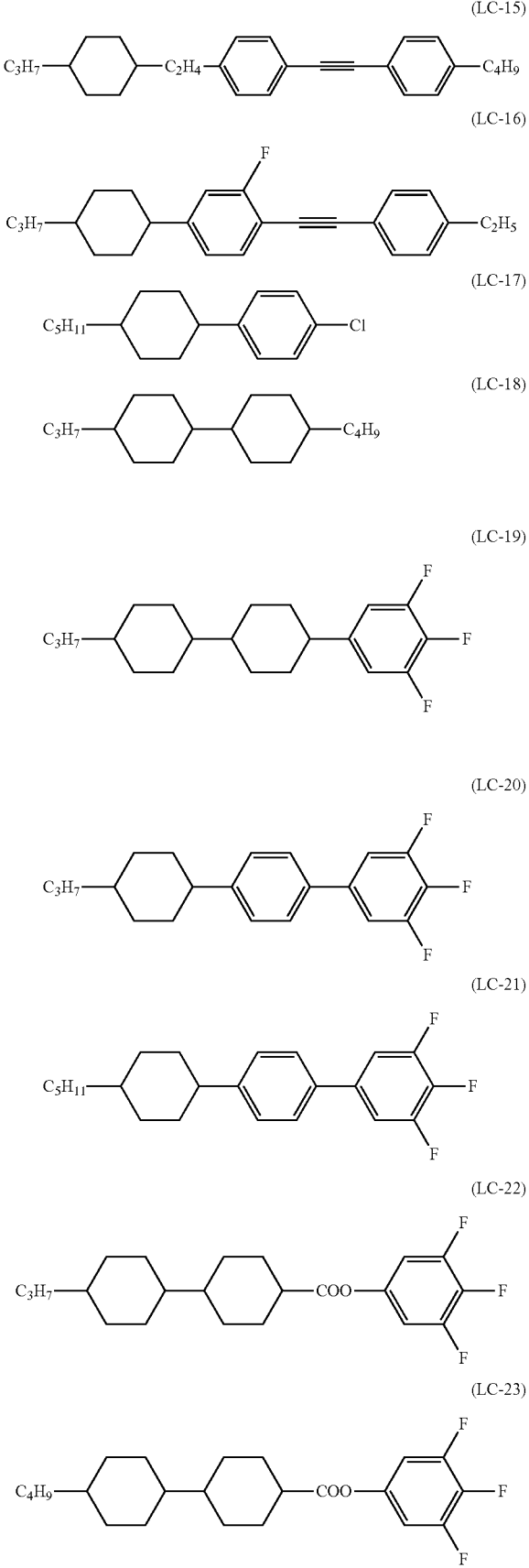

-continued (LC-24)
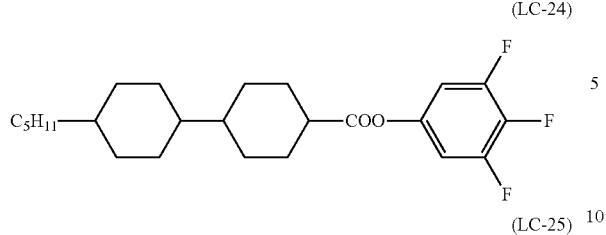

(LC-25)
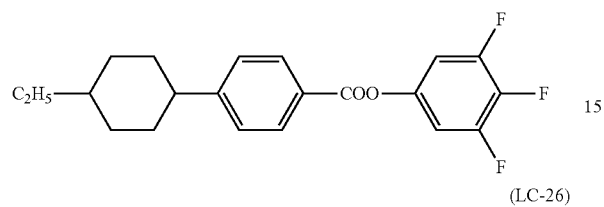

(LC-26)
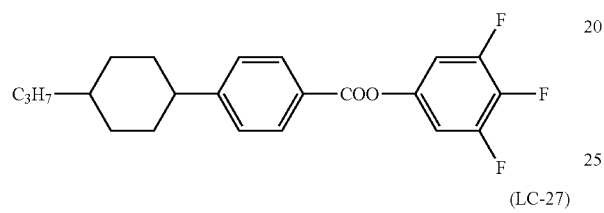

(LC-27)
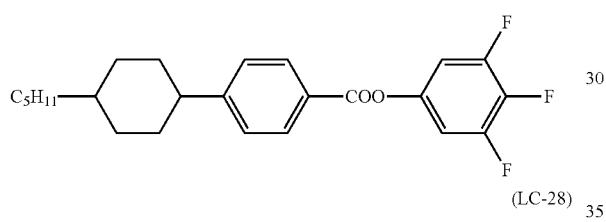

(LC-28)
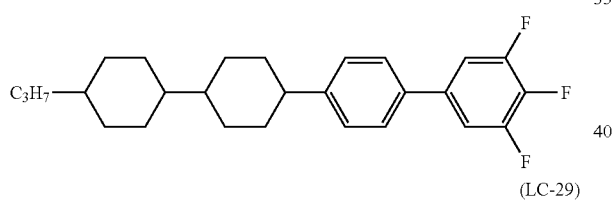

(LC-29)
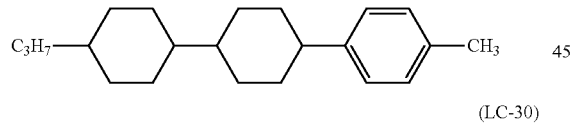

(LC-30)
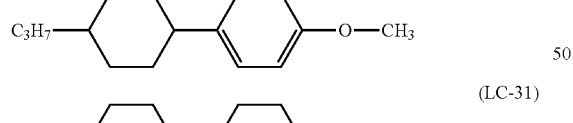

(LC-31)
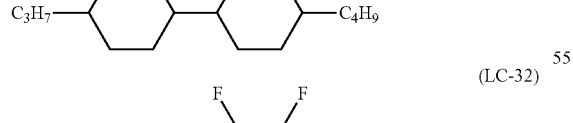

(LC-32)
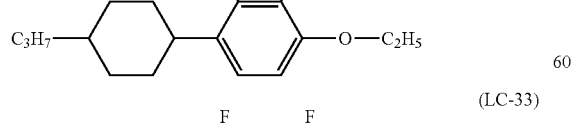

(LC-33)
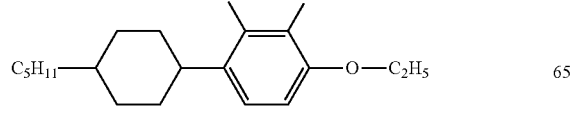

-continued (LC-34)
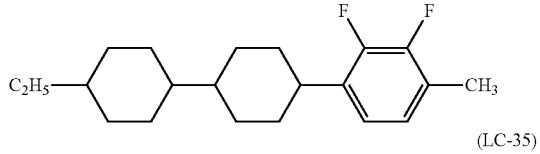

(LC-35)
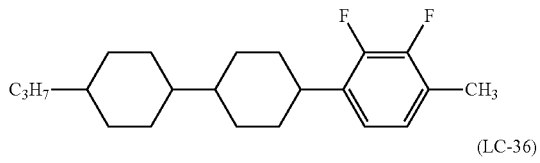

(LC-36)
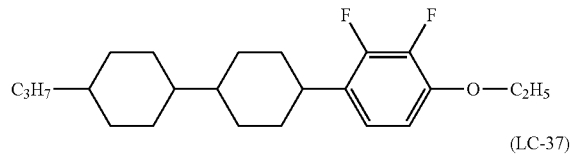

(LC-37)
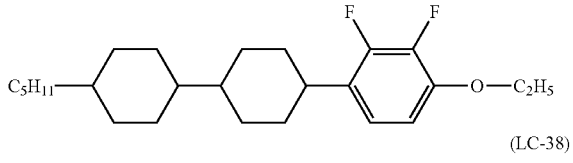

(LC-38)
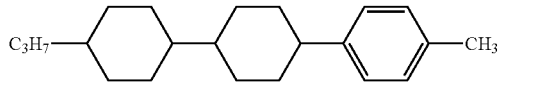

The polymerizable liquid crystal composition may include an optically active compound. The polymerizable liquid crystal composition to which a suitable amount of an optically active compound has been added or the polymerizable liquid crystal composition to which a suitable amount of an optically active polymerizable compound has been added is applied to a substrate subjected to alignment treatment and then is polymerized, giving an optical retardation film having a helical structure (a twist structure). The helical structure is fixed by polymerization of the polymerizable liquid crystal compound (M). Characteristics of the resulting anisotropic polymer depend on a helical pitch in the helical structure. The length of the helical pitch can be adjusted by the kinds and the amount of the optically active compound. Only one optically active compound may be added, or a plurality of optically active compounds may be added for the purpose of compensating the temperature dependence of the helical pitch. Incidentally, the polymerizable liquid crystal composition may include another polymerizable compound in addition to the polymerizable liquid crystal compound (M) and the optically active compound.

The selective reflection of visible light, which is the characteristics of the anisotropic polymer described above, arises from the action of a helical structure on incident light, which leads to the reflection of circularly polarized light or elliptically polarized light. Characteristics of the selective reflection are expressed as a function of $\lambda = n \cdot \text{Pitch}$; where $\lambda$ stands for the central wavelength of selective reflection, n stands for an average refractive index and Pitch stands for a helical pitch. Hence, the central wavelength ($\lambda$) or the wavelength width ($\Delta\lambda$) can be suitably adjusted by varying the value of n or Pitch. The wavelength width ($\Delta\lambda$) should be decreased for an improvement of color purity, and the wavelength width ($\Delta\lambda$) should be increased for broadband reflection. Furthermore, the selective reflection is greatly affected by polymer thickness. The thickness should not be made too small in order to maintain color purity. The thickness should not be made too large in order to maintain a uniform orientation. Thus, a suitable adjustment of the thickness is necessary, and a desirable thickness is in the range of approximately 0.5 μm to approximately 25 μm, and a more desirable cell thickness is in the range of approximately 1 μm to approximately 10 μm.

The negative-type C-plate (negative C-plate) described in W. H. de Jeu, Physical Properties of Liquid Crystalline Materials, Gordon and Breach, New York (1980) can be prepared by making the helical pitch shorter than the wavelengths of visible light. A shorter helical pitch can be achieved by use of an optically active compound having a large twisting power (HTP: helical twisting power) and by increasing the amount of the compound. The negative-type C-plate can be prepared when the central wavelength (λ) is approximately 350 nm or less, and preferably approximately 200 nm or less. This negative-type C-plate serves as an optical compensation film suitable for a liquid crystal display device of a VAN-type, a VAC-type, an OCB-type or the like.

The anisotropic polymer can be used for a reflection film described in JP 2004-333671 A, in which a wavelength range of reflection is set up in near infrared light (wavelengths from 800 nm to 2500 nm), by an increased helical pitch which is longer than that of visible light. Along helical pitch can be achieved by using an optically active compound having a small twisting power or by decreasing the amount of the optically active compound.

Any optically active compound may be used if the optically active compound can induce a helical structure and can be mixed appropriately with the polymerizable liquid crystal composition. The optically active compound may be polymerizable or non-polymerizable, and an optimum compound can be added in accordance with a purpose. The polymerizable compound is more suitable when heat resistance and solvent resistance are taken into consideration. Examples of a skeleton which exhibits optical activity include alkylene and alkenylene having one or more asymmetric carbons, or compounds having the following partial structures.

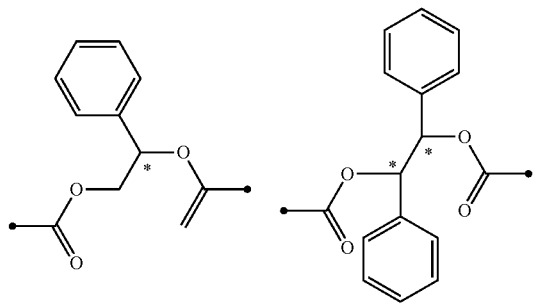

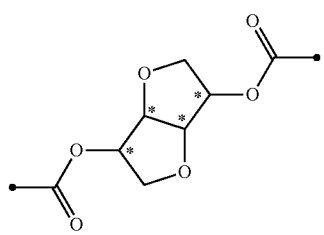

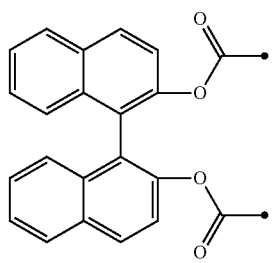

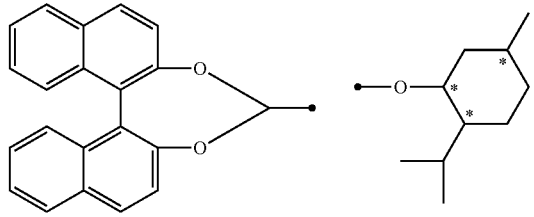

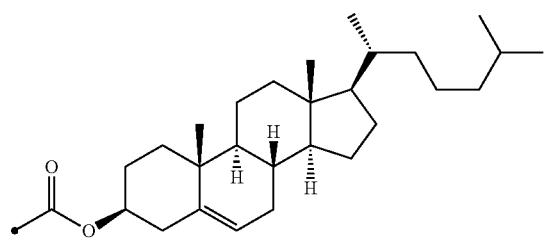

An optically active compound having a large twisting power (HTP: helical twisting power) among the compounds described above is suitable for decreasing the helical pitch. A representative example of a compound having a large twisting power is described in GB 2,298,202 and DE 10,221,751.

Concrete examples of a polymerizable optically active compound are shown below. In these examples, n and m are each independently an integer from 2 to 12. R is alkyl having 1 to 10 carbons.

(OP-1)
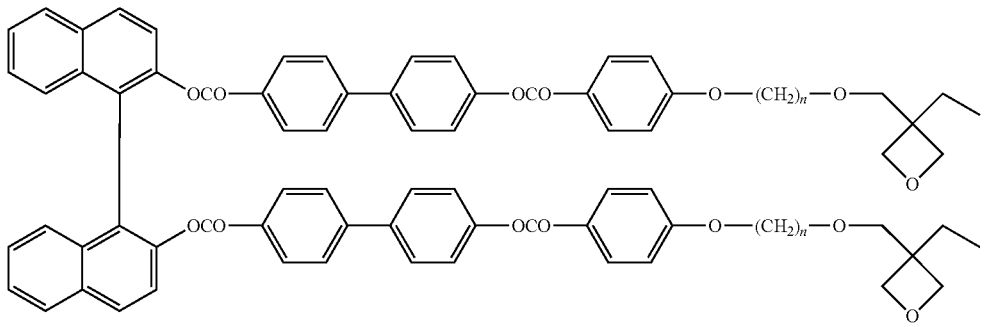
(OP-2)
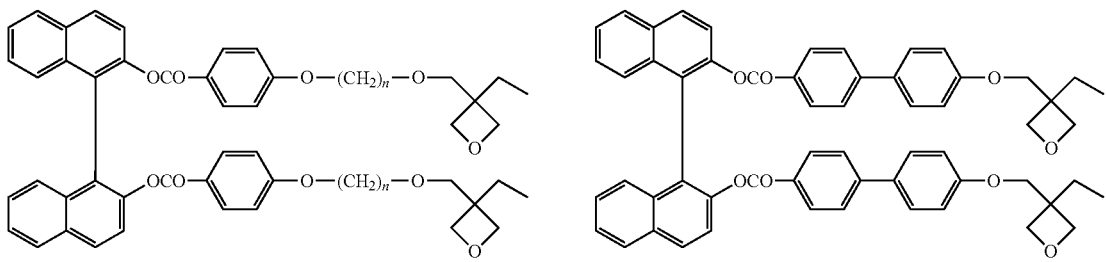
(OP-3)
(OP-4)
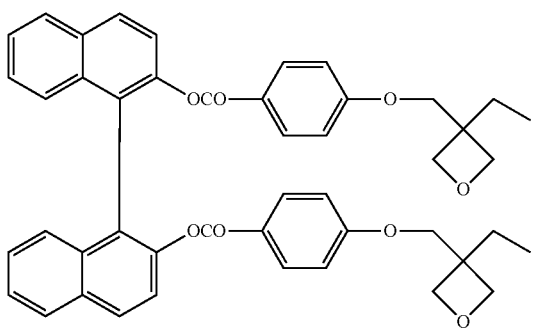
(OP-5)
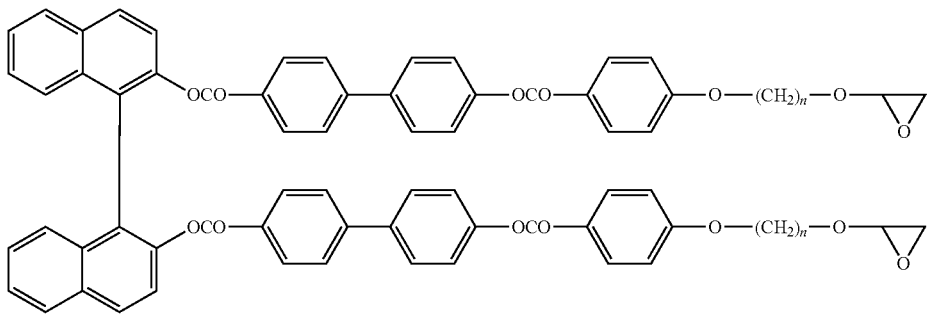
(OP-6)
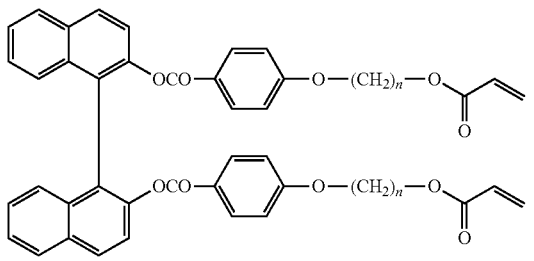
(OP-7)
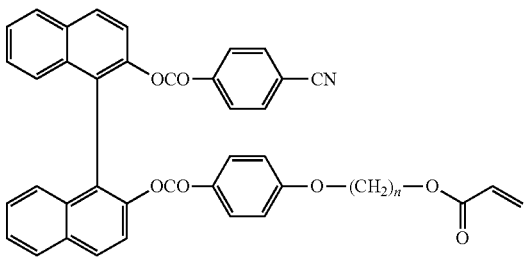

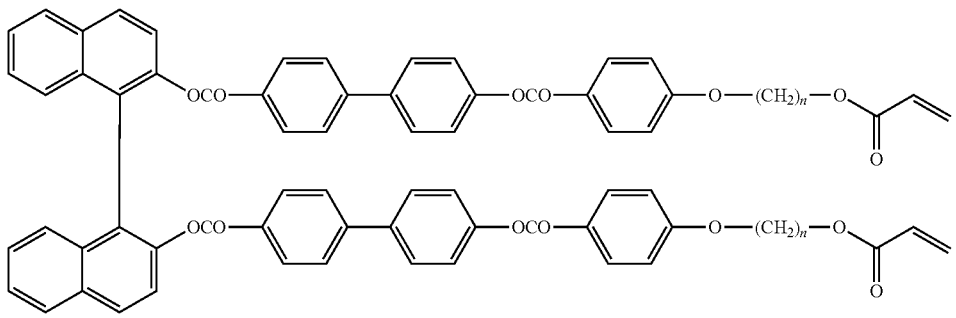
(OP-8)
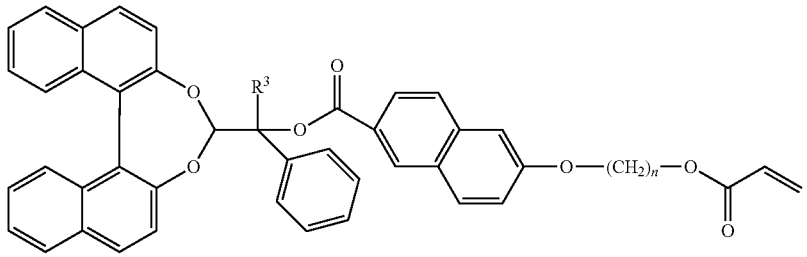
(OP-9)
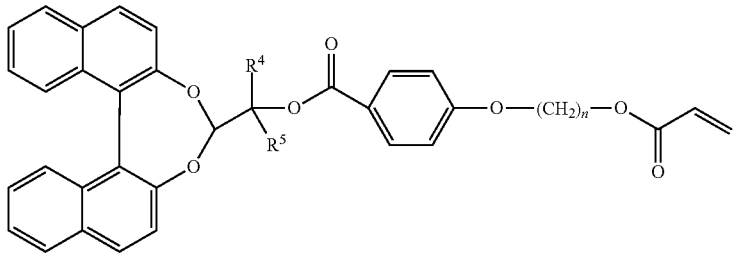
(OP-10)
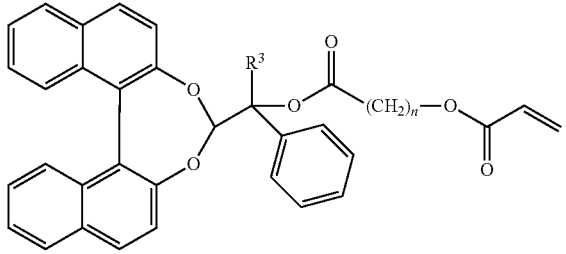
(OP-11)
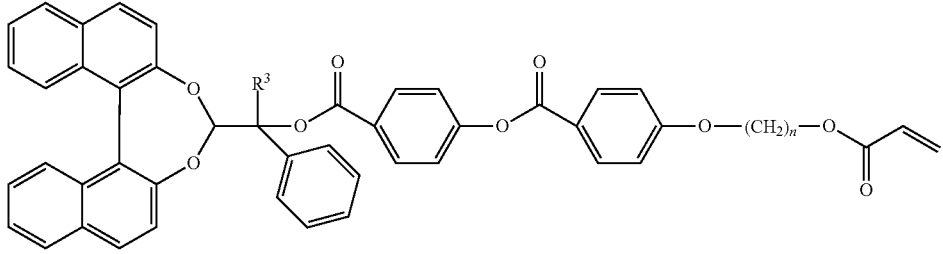
(OP-12)

In formula described above, $R^3$ is methyl, and $R^4$ and $R^5$ are each independently phenyl, alkyl having 1 to 6 carbons or trifluoromethyl.
(OP-13)
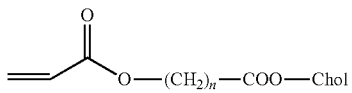
(OP-14)
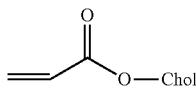
(OP-15)
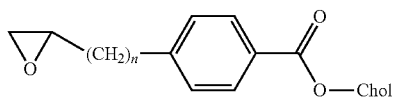
(OP-16)
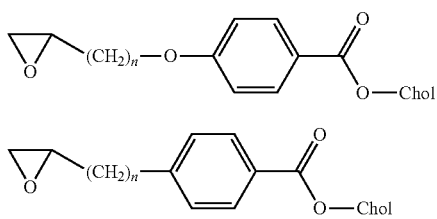
(OP-17)
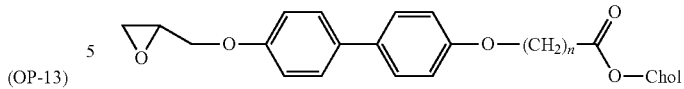
(OP-18)
(OP-19)
In formula described above, —COO-Chol means the following cholesterol moiety.
(OP-20)
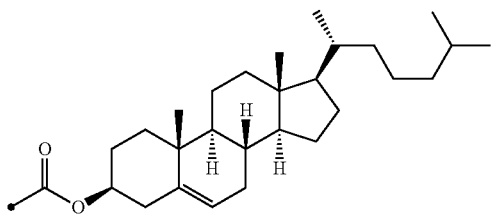
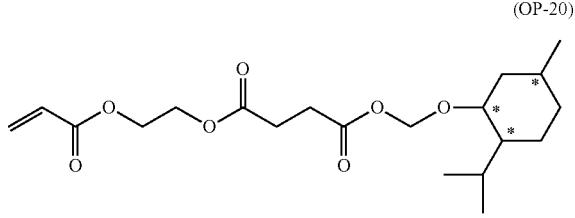
(OP-21)
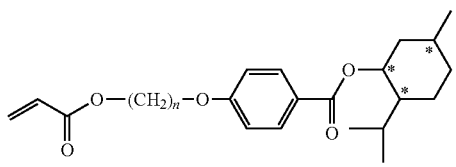
(OP-22)
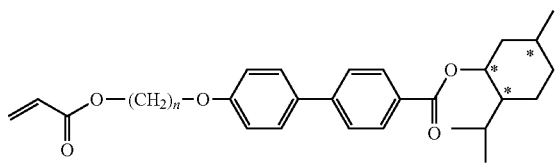
(OP-23)
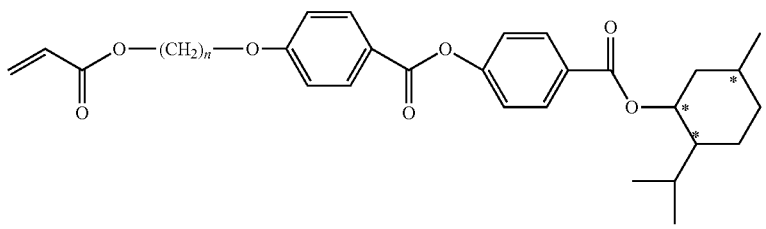
(OP-24)
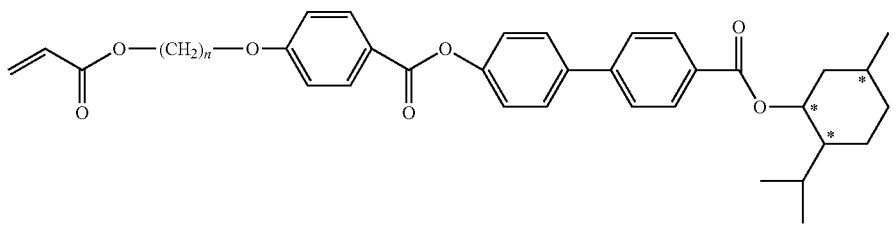

-continued
(OP-25)
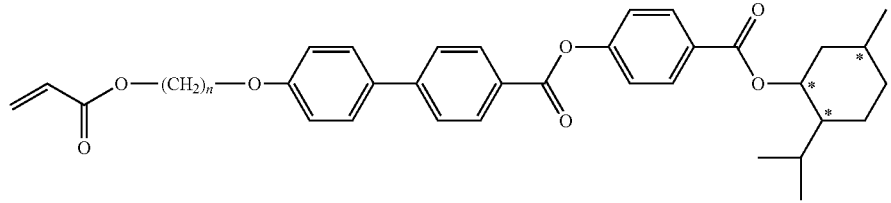
(OP-26)
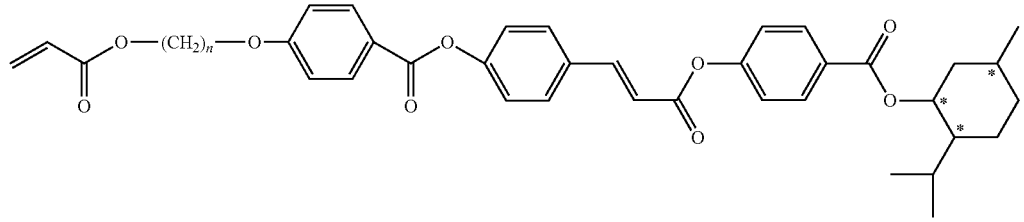
(OP-27)
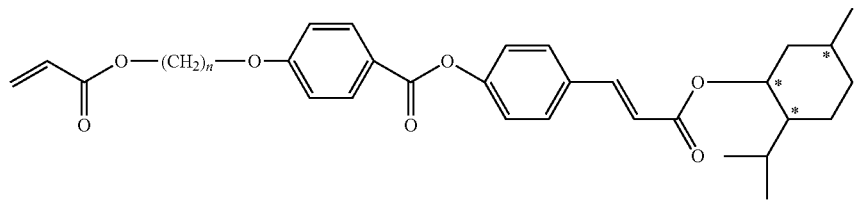
(OP-28) (OP-29)
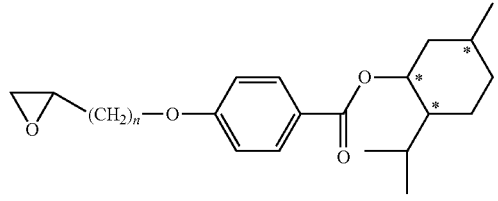
(OP-30)
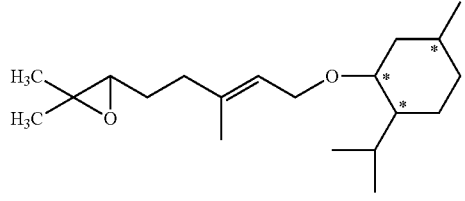
(OP-31)
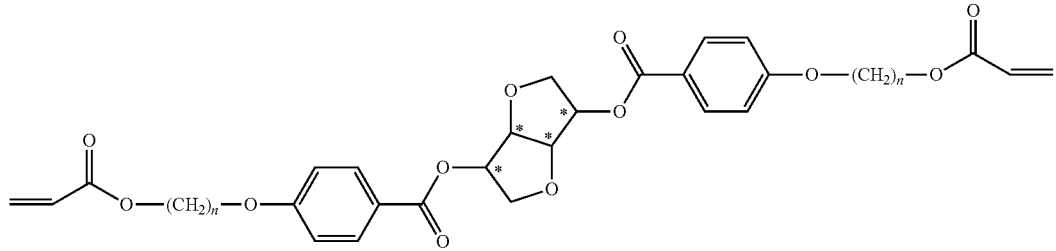
(OP-32)
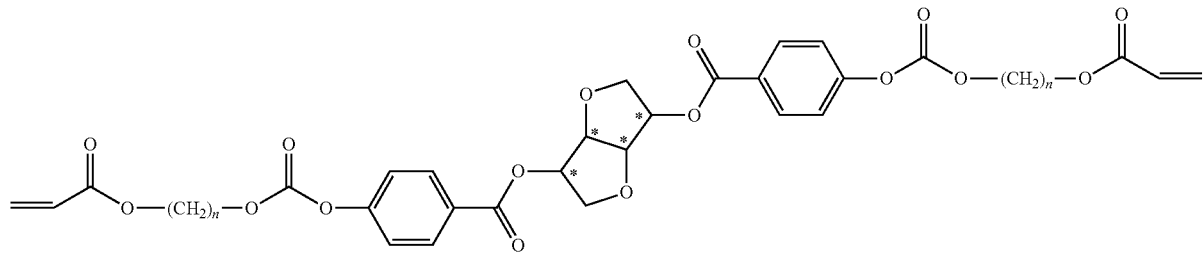

-continued
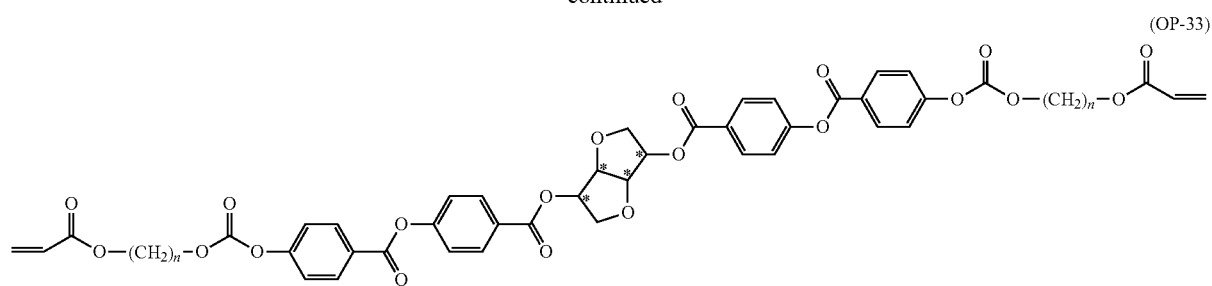
(OP-33)
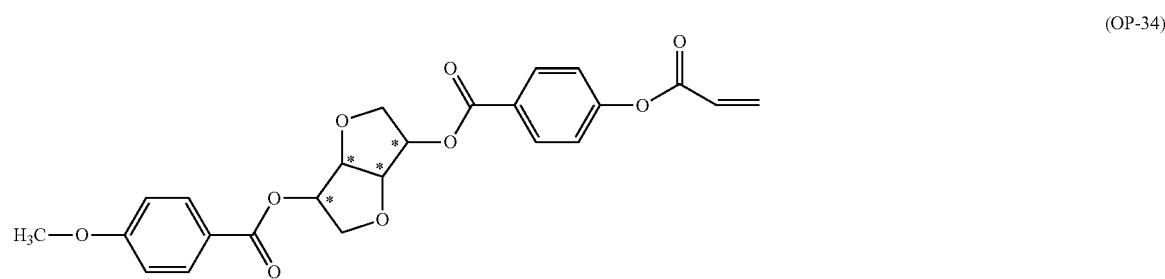
(OP-34)
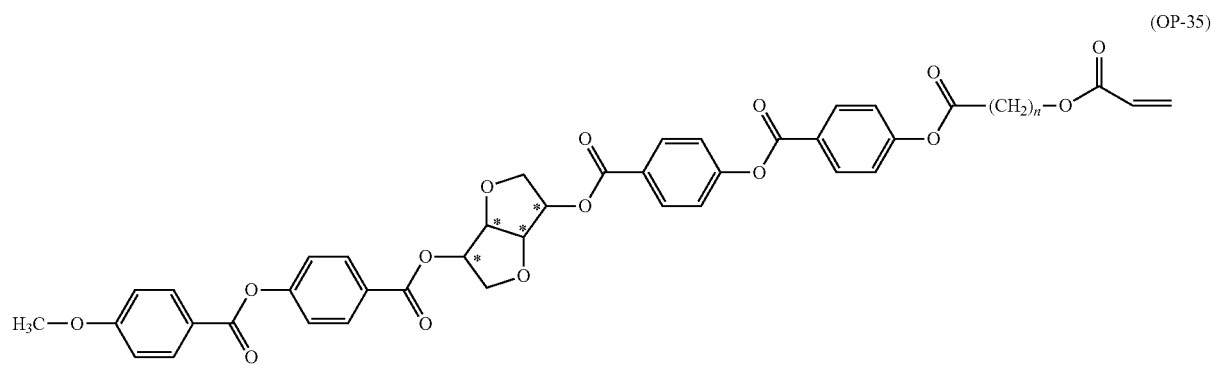
(OP-35)
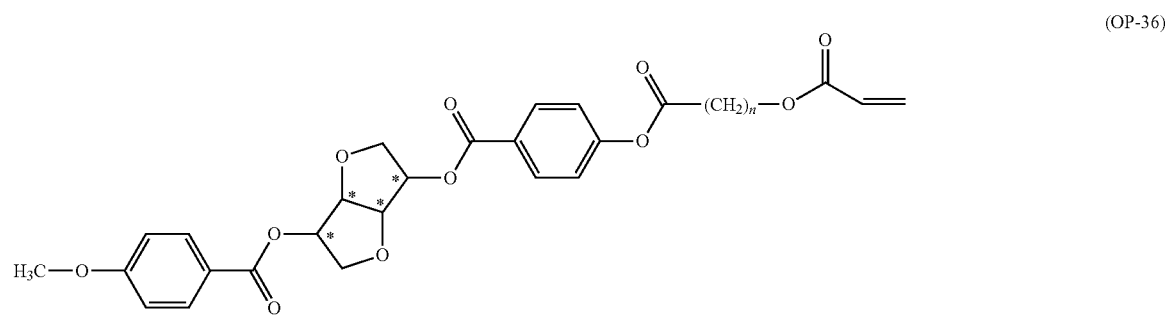
(OP-36)
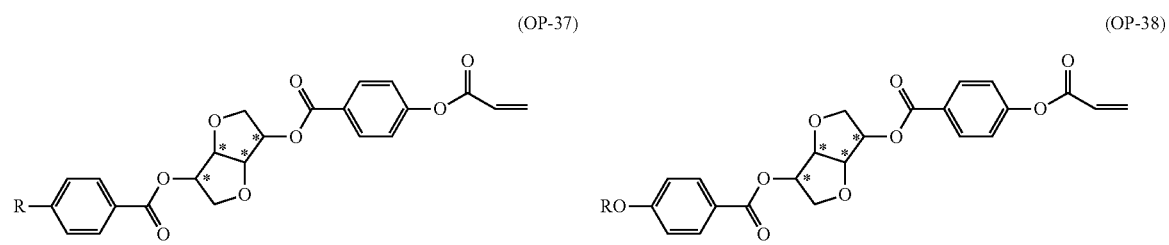
(OP-37) (OP-38)

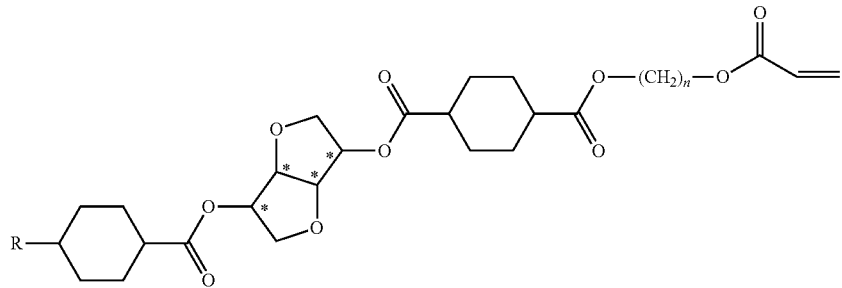
(OP-39)
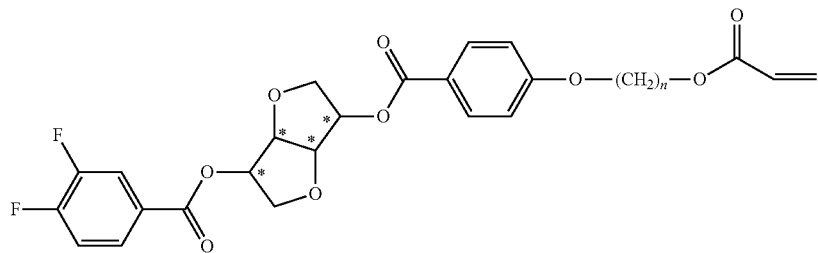
(OP-40)
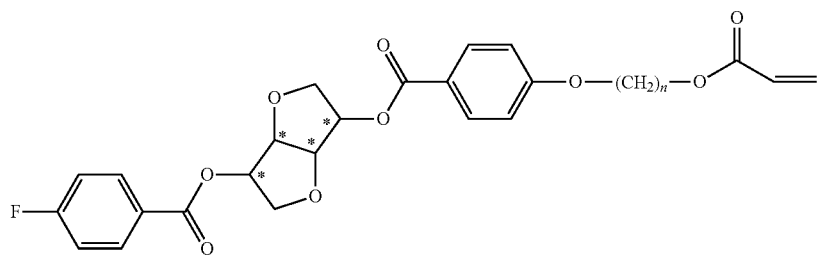
(OP-41)
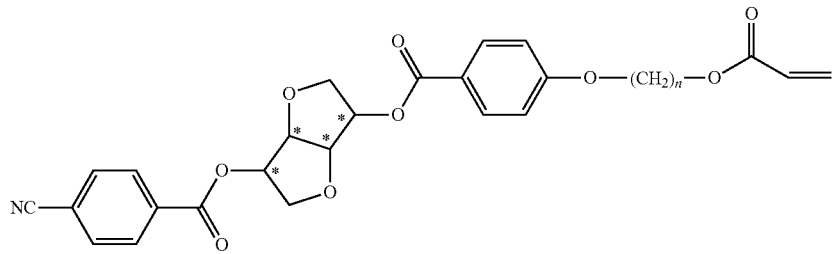
(OP-42)
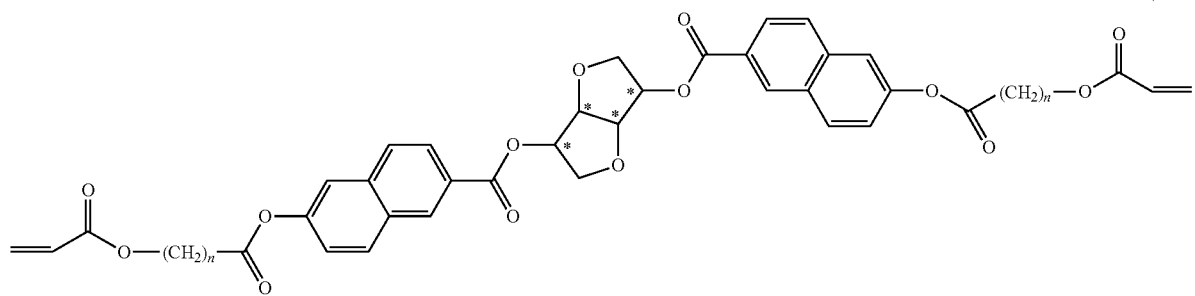
(OP-43)

-continued
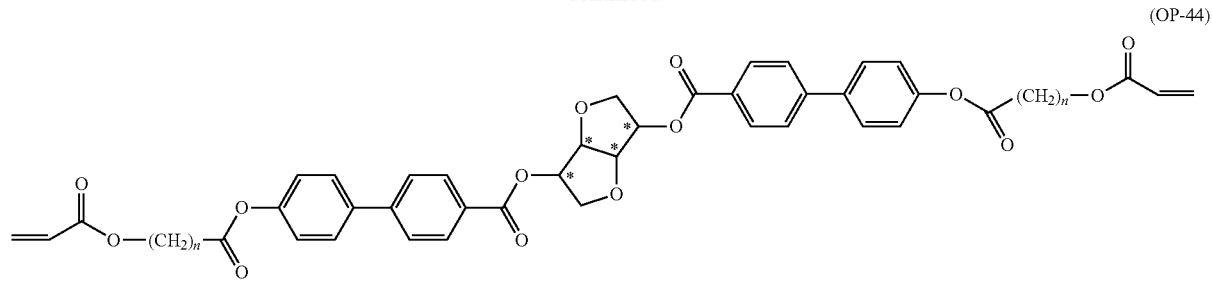
(OP-44)
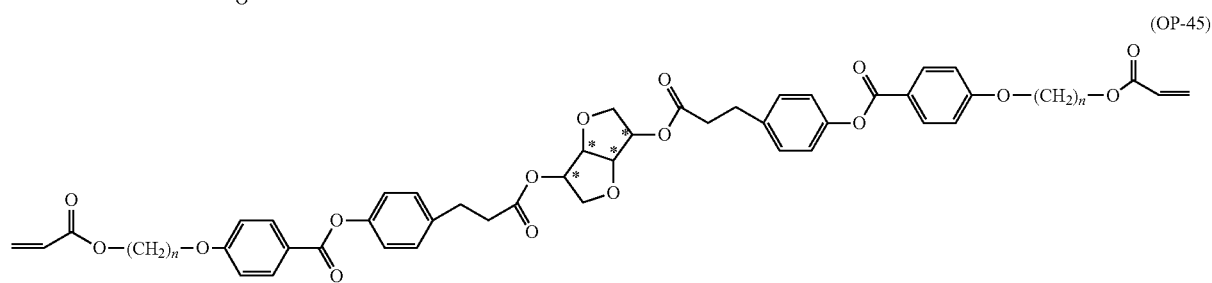
(OP-45)
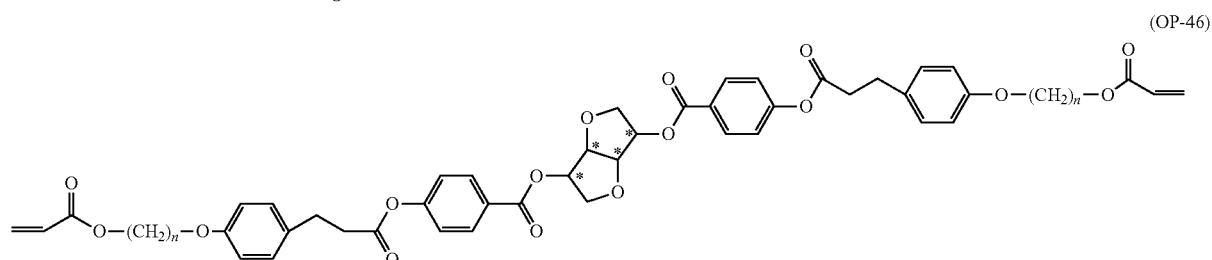
(OP-46)
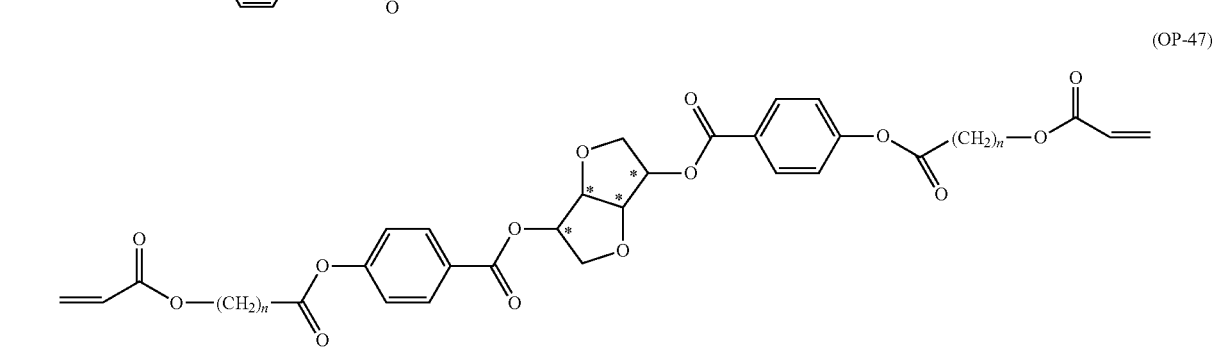
(OP-47)
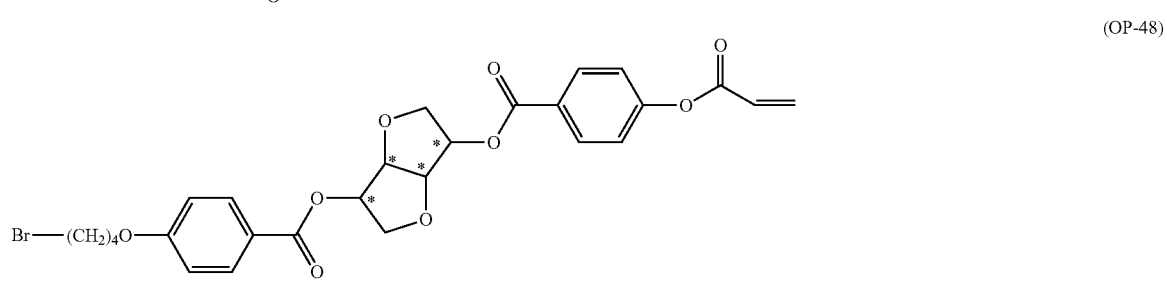
(OP-48)
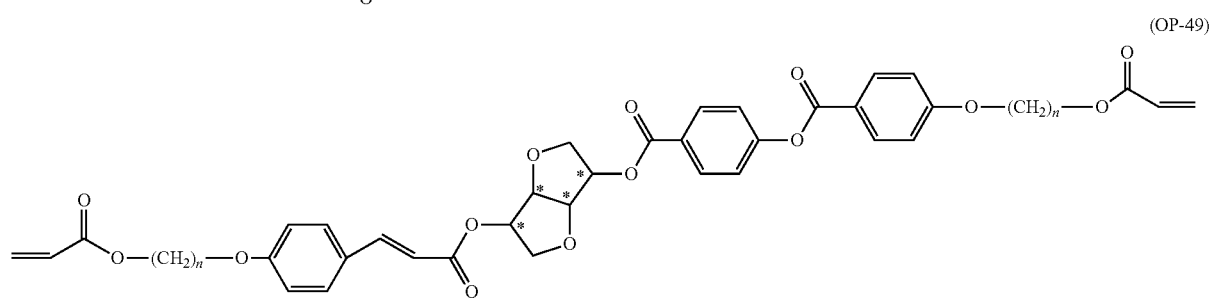
(OP-49)

-continued
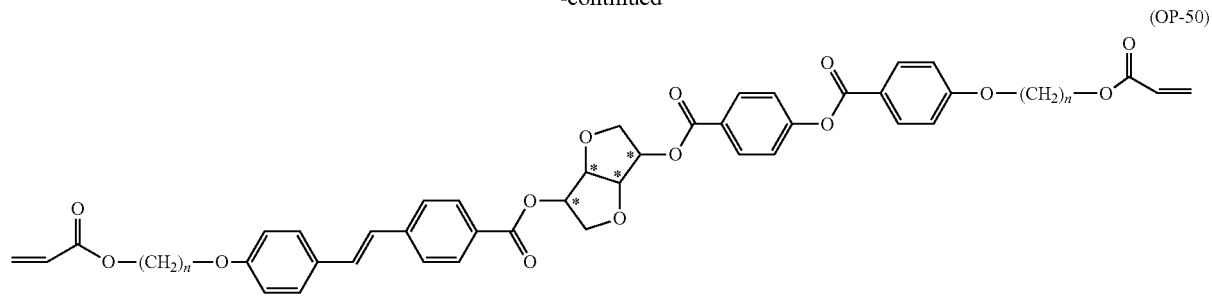
(OP-50)
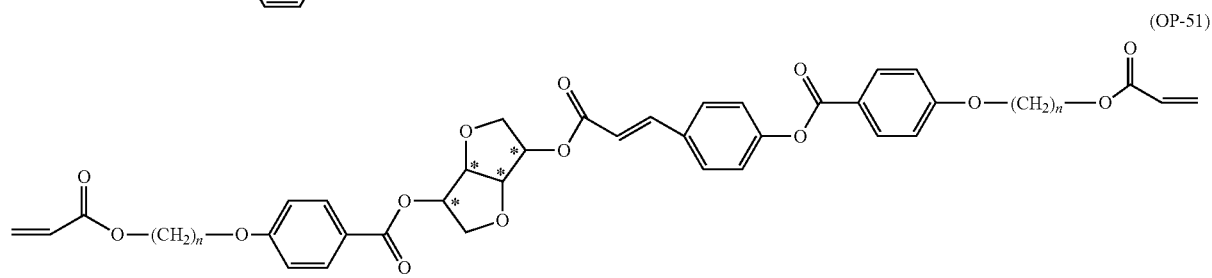
(OP-51)
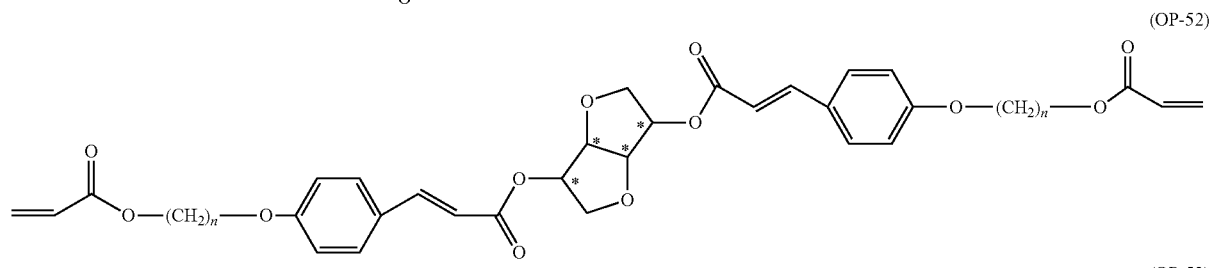
(OP-52)
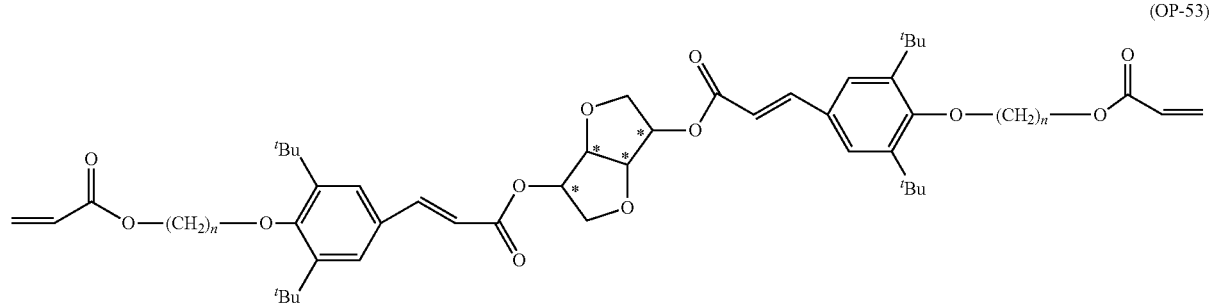
(OP-53)
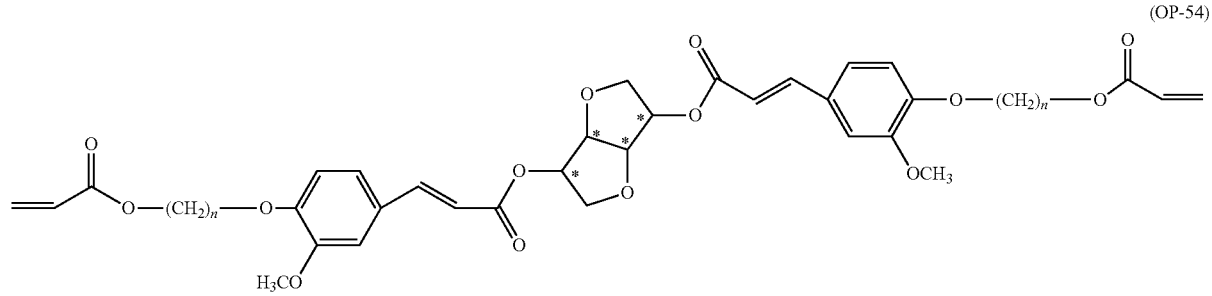
(OP-54)
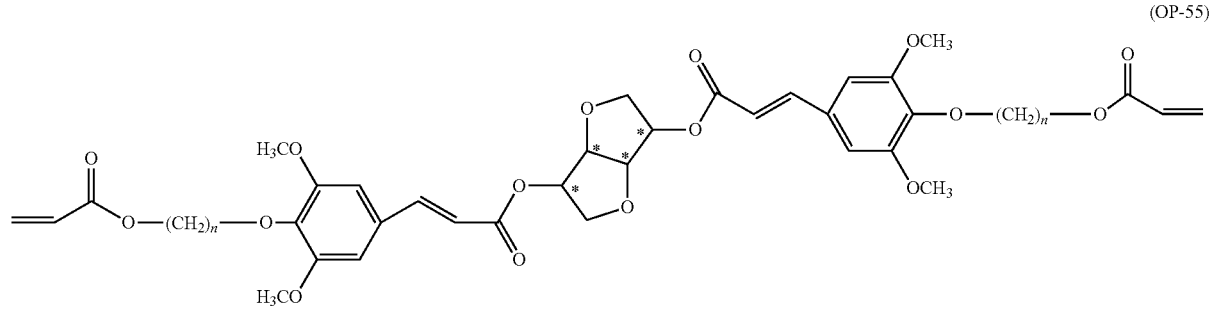
(OP-55)

-continued
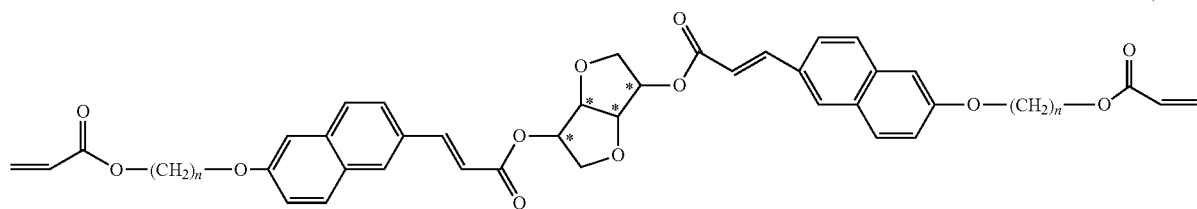
(OP-56)
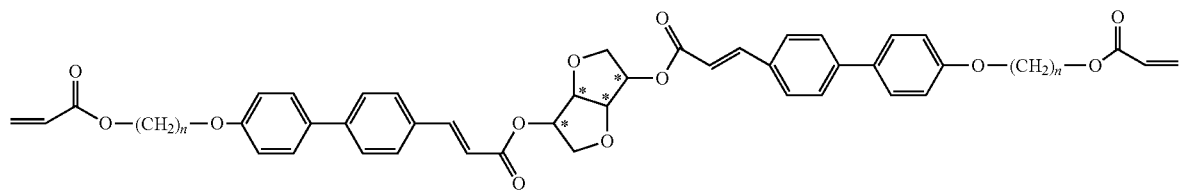
(OP-57)
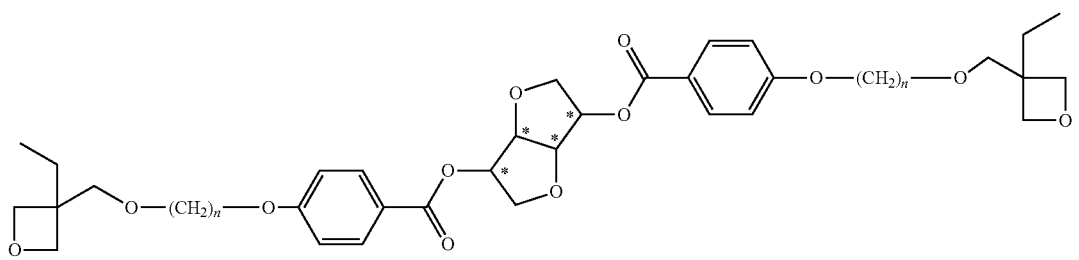
(OP-58)
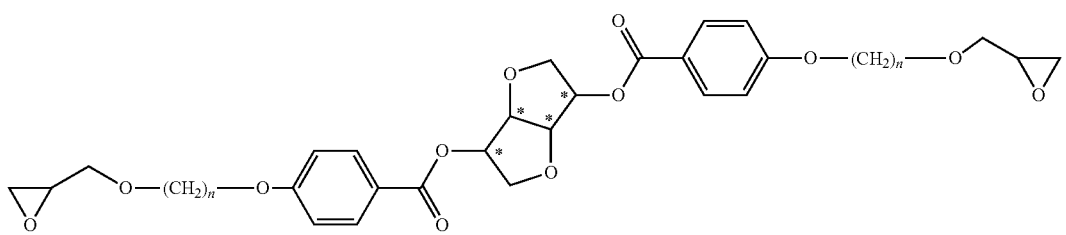
(OP-59)
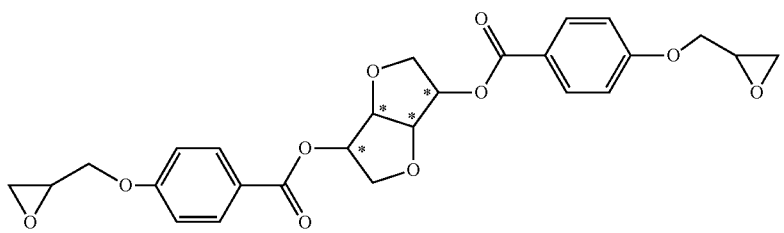
(OP-60)
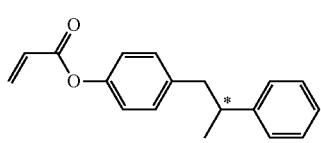
(OP-61)
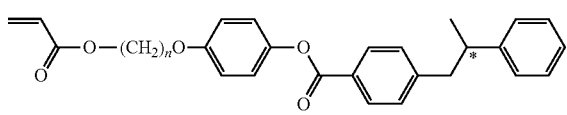
(OP-62)
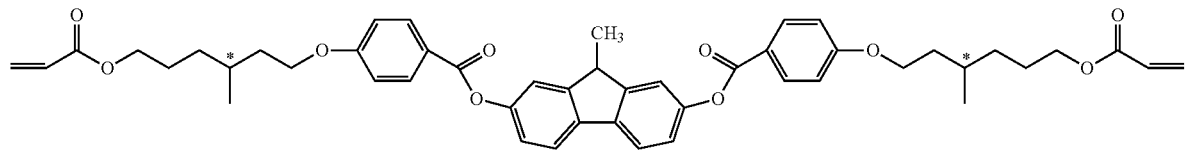
(OP-63)

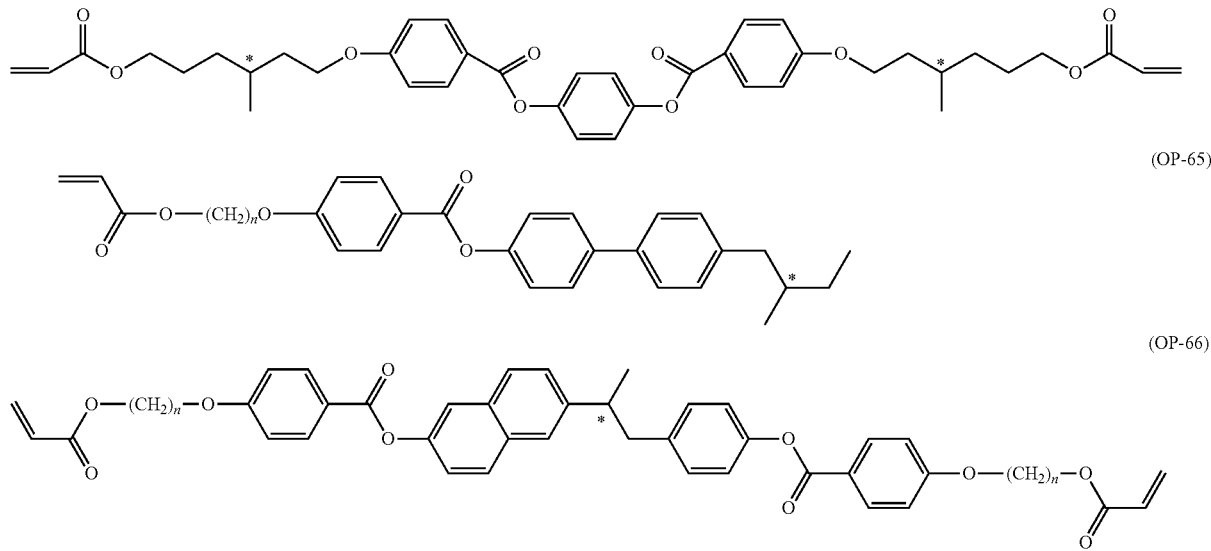

The polymerizable liquid crystal composition may include a polymerization initiator. The polymerization initiator can be selected according to the kinds of polymerization. Desirable initiators are shown below.

Examples of a photo-radical polymerization initiator include those described in the paragraphs from 0103 to 0104 of page 50 in JP 2008-266632 A. A desirable ratio of photopolymerization initiator is in the range of approximately 0.0001 to approximately 0.20 by weight based on the total weight of the polymerizable compound. A more desirable ratio is in the range of approximately 0.001 to approximately 0.10 by weight.

Desirable examples of the initiator used for thermal radical polymerization include benzoyl peroxide, diisopropyl peroxide dicarbonate, tert-butylperoxy-2-ethylhexanoate, tert-butylperoxy pivalate, di-tert-butyl peroxide, tert-butylperoxy benzoate, lauroyl peroxide, 3,3'-bis(methoxycarbonyl)-4,4'-bis(tert-butylperoxycarbonyl)benzophenone, dimethyl 2,2'-azobis(isobutyrate), azobisisobutyronitrile, and 1,1'-azobis(cyclohexanecarbonitrile), and also the compounds below.

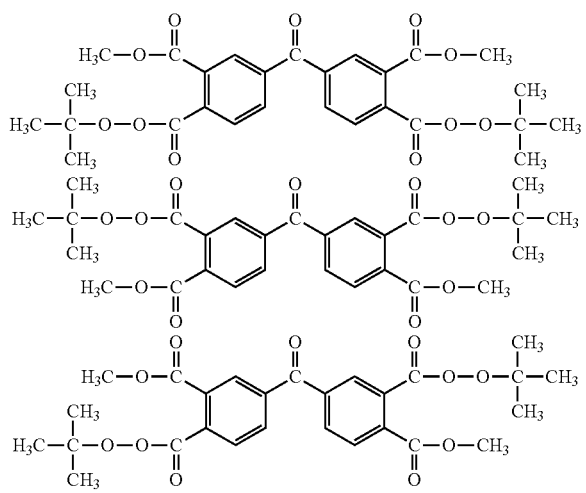

Commercially available azo-based initiator includes V-70, V-65, V-60, V-59, V-40, V-30, V-501, V-601, VE-073, VA-080, VA-086, VF-096, VAm-110, VAm-111, VA-044, VA-046B, VA-060, VA-061, V-50, VA-057, VA-067, VR-110, VPE-0201, VPE-0401, VPE-0601 and VPS-1001, all of which are available from Wako Pure Chemical Industries, Ltd.

A desirable initiator for cationic photopolymerization includes diaryliodonium salts (hereinafter referred to as DAS) and triarylsulfonium salts (hereinafter referred to as TAS). The DAS includes compounds described in the paragraph 0106 of page 51 in JP 2008-266632 A. A combination of the DAS and a photosensitizer is desirable. The photosensitizer includes thioxanthone, phenothiazine, chlorothioxanthone, xanthone, anthracene, diphenylanthracene and rubrene. Examples of the TAS include compounds described in the paragraph 0108 of page 51 in JP 2008-266632 A.

A commercially available initiator used for cationic photopolymerization includes Cyracure UVI-6990, Cyracure UVI-6974 and Cyracure UVI-6992 available from UCC; Adeka Optomer SP-150, SP-152, SP-170 and SP-172 available from Asahi Denka Kogyo K. K.; photoinitiator 2074 available from Rhodia Japan Ltd.; Irgacure 250 available from Ciba Japan K. K.; UV-9380C available from GE silicones Inc.; and HS series and CPI series available from San-Apro Ltd, and also includes TPS-series, TAZ-series, DPI-series, BPI-series, MDS-series, DTS-series, SI-series, PI-series, NDI-series, PAI-series, NAI-series, NI-series, DAM-series, MBZ-series, PYR-series, DNB-series and NB-series available from Midori Kagaku Co., Ltd.

A hardener may be added to the polymerizable liquid crystal composition. Examples of the hardener include an acidic or basic compound having a substituent such as amino, carboxyl or mercapto, and a compound having a phenol moiety or an acid anhydride moiety. A more desirable hardener is a basic compound having an amino group, a compound having a phenol moiety and a compound having an acid anhydride moiety. These compounds may be used together with a cationic photopolymerization initiator or a photo-radical polymerization initiator.

Examples of the hardener having an amino group include diethylenetriamine, triethylenetetramine, tetraethylenepentamine, m-xylenediamine, trimethylhexamethylenediamine, 2-methylpentamethylenediamine, diethylaminopropylamine, isophoronediamine, 1,3-bisaminomethylcyclohexane, bis(4-aminocyclohexyl)methane, norbornenediamine, 1,2-diaminocyclohexane, laromin, diaminodiphenylmethane, methaphenylenediamine, diaminodiphenylsulfone, polyoxypropylenediamine, polyoxypropylenetriamine, polycyclohexylpolyamine mixture and N-aminoethylpyperadine.

Examples of the hardener having a phenol moiety include phenol novolac, xylylene novolac, bisphenol A novolac, triphenylmethane novolac, biphenyl novolac, dicyclopentadiene phenol novolac and terpene phenol novolac.

Examples of the hardener having an acid anhydride moiety include tetrahydrophthalic anhydride, hexahydrophthalic anhydride, methyltetrahydrophthalic anhydride, methylhexahydrophthalic anhydride, nadic methyl anhydride, hydrogenated nadic methyl anhydride, trialkyltetrahydrophthalic anhydride, methylcyclohexene tetracarboxylic dianhydride, phthalic anhydride, trimellitic anhydride, pyromellitic anhydride, benzophenonetetracarboxylic dianhydride, ethylene glycol bis(anhydro-trimellitate), glycerin bis(anhydro-trimellitate)monoacetate, dodecenyl succinic anhydride, polyanhydrides of aliphatic dibasic acid and chlorendic anhydride.

A commercially available thermal polymerization initiator may be added to the polymerizable liquid crystal composition. Examples of a specific trade name include San-Aid SI-60, SI-80, SI-100, SI-110, SI-145, SI-150, SI-160 and SI-180 (these are main agents), and San-Aid SI (an auxiliary agent) available from Sanshin Chemical Industry Co., Ltd. The initiator may be used together with a radical photopolymerization initiator and a cationic photopolymerization initiator, or together with a radical photopolymerization initiator.

An amine-based hardener described in Review of Epoxy Resin, Vol 1 (Sousetu Epokisi Jusi, Vol. 1 in Japanese title; edited and published by The Japan Society of Epoxy Resin Technology; 2003) can be added depending on characteristics required.

The polymerizable liquid crystal composition may be applied to the surface of a substrate without a solvent. However, the solvent is usually used to facilitate the application. The polymerizable liquid crystal composition is diluted with the solvent, or each of the polymerizable liquid crystal compounds is diluted with the solvent and then the solutions are mixed. The solvent can be used solely or in combination of two or more of solvents. Examples of the solvent include ester-type solvents, amide-type solvents, alcohol-type solvents, ether-type solvents, glycol monoalkyl ether-type solvents, aromatic hydrocarbon-type solvents, halogenated aromatic hydrocarbon-type solvents, aliphatic hydrocarbon-type solvents, halogenated aliphatic hydrocarbon-type solvents, alicyclic hydrocarbon-type solvents, ketone-type solvents and acetate-type solvents.

Desirable examples of the ester-type solvents include alkyl acetates (for example, methyl acetate, ethyl acetate, propyl acetate, isopropyl acetate, butyl acetate, 3-methoxybutyl acetate, isobutyl acetate, pentyl acetate and isopentyl acetate), ethyl trifluoroacetate, alkyl propionate (for example, methyl propionate, methyl 3-methoxypropionate, ethyl propionate, propyl propionate and butyl propionate), alkyl butanoates (for example, methyl butanoate, ethyl butanoate, butyl butanoate, isobutyl butanoate and propyl butanoate), dialkylmalonates (for example, diethyl malonates), alkyl glycolates (for example, methyl glycolate and ethyl glycolate), alkyl lactates (for example, methyl lactate, ethyl lactate, isopropyl lactate, n-propyl lactate, butyl lactate and ethylhexyl lactate), monoacetin, γ-butyrolactone and γ-valerolactone.

Desirable examples of the amide-type solvents include N-methyl-2-pyroridone, N,N-dimethylacetamide, N-methylpropionamide, N,N-dimethylformamide, N,N-diethylformamide, N,N-diethylacetamide, N,N-dimethylacetamide dimethyl acetal, N-methylcaprolactam and dimethylimidazolidinone.

Desirable examples of the alcohol-type solvents include methanol, ethanol, 1-propanol, 2-propanol, 1-methoxy-2-propanol, t-butyl alcohol, sec-butyl alcohol, butanol, 2-ethylbutanol, n-hexanol, n-heptanol, n-octanol, 1-dodecanol, ethylhexanol, 3,5,5-trimethylhexanol, n-amyl alcohol, hexafluoro-2-propanol, glycerol, ethylene glycol, diethylene glycol, triethylene glycol, tetraethylene glycol, propylene glycol, dipropylene glycol, tripropylene glycol, hexylene glycol, 1,3-butanediol, 1,4-butanediol, 2,3-butanediol, 1,5-pentanediol, 2,4-pentanediol, 2,5-hexanediol, 3-methyl-3-methoxybutanol, cyclohexanol and methylcyclohexanol.

Desirable examples of the ether-type solvents include ethylene glycol dimethyl ether, diethylene glycol dimethyl ether, bis(2-propyl)ether, 1,4-dioxane, cyclopentyl methyl ether, terpinyl methyl ether, dihydroterpinyl methyl ether, 1,8-cineol, 1,4-cineol and tetrahydrofuran (THF).

Desirable examples of the glycol monoalkyl ether-type solvents include ethylene glycol monoalkyl ethers (for example, ethylene glycol monomethyl ether and ethylene glycol monobutyl ether), diethylene glycol monoalkyl ethers (for example, diethylene glycol monoethyl ether), triethylene glycol monoalkyl ethers, propylene glycol monoalkyl ethers (for example, propylene glycol monobutyl ether), dipropylene glycol monoalkyl ethers (for example, dipropylene glycol monomethyl ether), ethylene glycol monoalkyl ether acetates (for example, ethylene glycol monobutyl ether acetate), diethylene glycol monoalkyl ether acetates (for example, diethylene glycol monoethyl ether acetate), triethylene glycol monoalkyl ether acetates, propylene glycol monoalkyl ether acetates (for example, propylene glycol monomethyl ether acetate, propylene glycol monoethyl ether acetate and propylene glycol monobutyl ether acetate), dipropylene glycol monoalkyl ether acetates (for example, dipropylene glycol monomethyl ether acetate) and diethylene glycol methyl ethyl ether.

Desirable examples of the aromatic hydrocarbon-type solvents include benzene, toluene, xylene, mesitylene, ethylbenzene, diethylbenzene, i-propylbenzene, n-propylbenzene, t-butylbenzene, s-butylbenzene, n-butylbenzene, anisole, p-cymene, limonene, terpinolene and tetraline. A desirable example of the halogenated aromatic hydrocarbon-type solvents includes chlorobenzene. Desirable examples of the aliphatic hydrocarbon-type solvents include hexane and heptane. Desirable examples of the halogenated aliphatic hydrocarbon-type solvents include chloroform, dichloromethane, carbon tetrachloride, dichloroethane, trichloroethylene and tetrachloroethylene. Desirable examples of the alicyclic hydrocarbon-type solvents include cyclohexane and decaline.

Desirable examples of the ketone-type solvents include acetone, methyl ethyl ketone, methyl isobutyl ketone, cyclohexanone, cyclopentanone, dihydrocarvone, menthone, piperitenone and methyl propyl ketone.

Desirable examples of the acetate-type solvents include ethylene glycol monomethyl ether acetate, propylene glycol monomethyl ether acetate, propylene glycol monoethyl ether acetate, methyl acetoacetate, α-terpinyl acetate, perillyl acetate, 3-octyl acetate, 2-octyl acetate, myrtenyl acetate, isobonyl acetate, dihydroterpinyl acetate, dihydroocarvyl acetate, carvyl acetate and 1-methoxy-2-propyl acetate.

The amide-type solvents, the aromatic hydrocarbon-type solvents and the ketone-type solvents are desirable in view of the solubility of the polymerizable liquid crystal compound. The ester-type solvents, the alcohol-type solvents, the ether-type solvents and the glycol monoalkyl ether-type solvents are also desirable in consideration of the boiling points of the solvents. Although selection of the solvent is not especially limited, it is necessary to decrease drying temperature in order to avoid deformation of a supporting substrate and to prevent erosion of the supporting substrate caused by the solvent when a plastic substrate is used as the supporting substrate. Desirable examples of the solvent used in such cases include the aromatic hydrocarbon-type solvents, the ketone-type solvents, the ester-type solvents, the ether-type solvents, the alcohol-type solvents, the acetate-type solvents and the glycol monoalkyl ether-type solvents.

A desirable ratio of the solvent in the polymerizable liquid crystal composition is in the range of approximately 30% to approximately 95% by weight based on the total weight of the solution. The lower limit of the range is determined in view of the solubility of the polymerizable liquid crystal compound and an optimum viscosity for applying the solution, and the upper limit is determined in view of an economic standpoint of the solvent cost, and the period of time and the amount of heat consumed during evaporation of the solvent. A more desirable ratio is in the range of approximately 60% to approximately 90% by weight, and the most desirable ratio is in the range of approximately 70% to approximately 85% by weight.

Examples of an application method for the formation of a uniform film thickness include spin coating, micro-gravure coating, gravure coating, wire-bar coating, dip coating, spray coating, meniscus coating and die coating.

The polymerizable liquid crystal composition may include a surfactant. The surfactant facilitates to apply the composition to a supporting substrate, giving a paint film with a uniform thickness. The surfactant also has the effect of adjusting orientation of a liquid crystal phase. A desirable surfactant includes cationic surfactant, anionic surfactant and nonionic surfactant. A more desirable surfactant includes nonionic surfactant. Desirable examples of the nonionic surfactant include a fluorine-based nonionic surfactant, a silicone-based nonionic surfactant and a hydrocarbon-based nonionic surfactant.

Examples of the silicone-based nonionic surfactant include Polyflow ATF-2, Granol 100, Granol 115, Granol 400, Granol 410, Granol 435, Granol 440, Granol 450, Granol B-1484, Polyflow KL-250, Polyflow KL-260, Polyflow KL-270, Polyflow KL-280, BYK-300, BYK-302, BYK-306, BYK-307, BYK-310, BYK-315, BYK-320, BYK-322, BYK-323, BYK-325, BYK-330, BYK-331, BYK-333, BYK-337, BYK-341, BYK-344, BYK-345, BYK-346, BYK-347, BYK-348, BYK-370, BYK-375, BYK-377, BYK-378, BYK-3500, BYK-3510 and BYK-3570, where the main component is a modified silicone, and those of which are available from Kyoeisha Chemical Co., Ltd.

Examples of the fluorine-based nonionic surfactant include BYK-340, Futargent 251, Futargent 221MH, Futargent 250, FTX-215M, FTX-218M, FTX-233M, FTX-245M, FTX-290M, FTX-209F, FTX-213F, Futargent 222F, FTX-233F, FTX-245F, FTX-208G, FTX-218G, FTX-240G, FTX-206D, Futargent 212D, FTX-218, FTX-220D, FTX-230D, FTX-240D, FTX-720C, FTX-740C, FTX-207S, FTX-211S, FTX-220S, FTX-230S, KB-L82, KB-L85, KB-L97, KB-L109, KB-L110, KB-F2L, KB-F2M, KB-F2S, KB-F3M and KB-FaM.

Examples of the hydrocarbon-based nonionic surfactant include Polyflow No. 3, Polyflow No. 50EHF, Polyflow No. 54N, Polyflow No. 75, Polyflow No. 77, Polyflow No. 85HF, Polyflow No. 90, Polyflow No. 95, BYK-350, BYK-352, BYK-354, BYK-355, BYK-358N, BYK-361N, BYK-380N, BYK-381, BYK-392 and BYK-Silclean 3700, where the main component is an acryl-type polymer. Incidentally, both "Polyflow" and "Granol" described above are trade names of the products available from Kyoeisha Chemical Co., Ltd. "BYK" is a trade name of the product available from BYK Additives & Instruments. "Futargent", "FTX" and "KB" are trade names of the products available from Neos Company Limited. The amount of the surfactant depends on the kinds of the surfactant, composition ratios of a composition and so forth. The ratio of the surfactant is in the range of approximately 0.0001 to approximately 0.03 by weight ratio, and preferably in the range of approximately 0.0003 to approximately 0.02 by weight based on the total weight polymerizable liquid crystal composition (excluding a solvent).

The polymerizable liquid crystal composition may include an organosilicon compound for an adjustment of orientation. Concrete examples include amine-based silanes such as 3-aminopropyltrimethoxysilane, 3-aminopropyltriethoxysilane, 3-aminopropyldimethylethoxysilane, 3-aminopropyldiisopropylethoxysilane, 3-aminopropylmethyldiethoxysilane, 3-aminopropylpentamethyldisiloxane, 3-aminopropylmethylbis(trimethylsiloxy)silane, 3-aminopropyltris(trimethylsiloxy)silane, 3-aminobutyltriethoxysilane, N-(2-aminoethyl)-3-aminopropylmethyldimethoxysilane, N-(2-aminoethyl)-3-aminopropyltrimethoxysilane, N-(6-aminohexyl)-3-aminopropyltrimethoxysilane, (3-trimethoxysilylpropyl)diethylenetriamine and ketimine-based silanes such as 3-triethoxysilyl-N-(1,3-dimethyl-butylidene). The polymerizable liquid crystal composition may include another organosilicon compound to adjust adhesion to a supporting substrate. Concrete examples include vinyltrialkoxysilanes, 3-isocyanatopropyltriethoxysilane, 3-glycidoxypropyltrialkoxysilane, 3-chlorotrialkoxysilanes, 3-acryloxypropyltrimethoxysilane, 3-methacryloxypropyltrialkoxysilanes, 1,3-bis(3-aminopropyl)tetramethyldisiloxane and 1,4-bis(3-aminopropyldimethylsilyl)benzene. Another example includes corresponding dialkoxymethylsilanes in which one of three alkoxy groups of the above silanes has been replaced by a methyl group. The amount of the organosilicon compound depends on its kinds, the composition ratios of the composition and so forth, and the ratio of the organosilicon compound is in the range of approximately 0.01 to approximately 0.30 by weight, and preferably in the range of approximately 0.03 to approximately 0.15 by weight based on the total weight of the polymerizable liquid crystal composition (excluding a solvent).

Mechanical strength of the polymer can be adjusted by the addition of one, or two or more chain-transfer agents to the polymerizable liquid crystal composition. The chain-transfer agent adjusts the length of polymer chain or the length of two bridging polymer chains. These lengths can also be simultaneously adjusted. As the chain-transfer agent is increased, the chain length decreases. A desirable chain-transfer agent is a thiol compound. Examples of a monofunctional thiol include dodecanthiol and 2-ethylhexyl-(3-mercaptopropionate). Examples of a polyfunctional thiol include trimethyrolpropanetris(3-mercaptopropionate), pentaerythritoltetrakis(3-mercaptopropionate), 1,4-bis(3-mercaptobutylyloxy)butane (Karenz MT BD1), pentaerythritoltetrakis(3-mercapto butylate) (Karenz MT PE1) and 1,3,5-tris(3-mercaptobutyloxyethyl)-1,3,5-triazine-2,4,6(1H,3H,5H)-trione (Karenz MT NR1). "Karenz" is a trade name of Showa Denko K. K.

A polymerization inhibitor can be added to the polymerizable liquid crystal composition to avoid polymerization during the storage. Desirable examples of the polymerization inhibitor include 2,5-di(t-butyl)hydroxytoluene (BHT), hydroquinone, methyl blue, diphenylpicric acid hydrazide (DPPH), benzothiazine, 4-nitrosodimethylaniline (NIDI) and o-hydroxybenzophenone.

An oxygen inhibitor can be added to the polymerizable liquid crystal composition in order to increase preservation stability. Free radicals generated in the polymerizable liquid crystal composition react with oxygen under an atmosphere, giving peroxide radicals, and undesirable reactions with the polymerizable compound are accelerated. It is desirable to add the oxygen inhibitor in order to prevent the reactions. An example of the oxygen inhibitor is phosphoric esters.

An ultraviolet absorber, a light stabilizer (a radical scavenger), an antioxidant or the like may be added to the polymerizable liquid crystal composition for further increasing weather resistance of the polymer. Examples of the ultraviolet absorber include Tinuvin PS, Tinuvin P, Tinuvin 99-2, Tinuvin 109, Tinuvin 213, Tinuvin 234, Tinuvin 326, Tinuvin 328, Tinuvin 329, Tinuvin 384-2, Tinuvin 571, Tinuvin 900, Tinuvin 928, Tinuvin 1130, Tinuvin 400, Tinuvin 405, Tinuvin 460, Tinuvin 479, Tinuvin 5236, Adeka Stab LA-32, Adeka Stab LA-34, Adeka Stab LA-36, Adeka Stab LA-31, Adeka Stab 1413 and Adeka Stab LA-51. "Tinuvin" is a trade name of Ciba Japan K. K. and "Adeka Stab" is a trade name of Adeka Corporation.

Examples of the light stabilizer include Tinuvin 111FDL, Tinuvin 123, Tinuvin 144, Tinuvin 152, Tinuvin 292, Tinuvin 622, Tinuvin 770, Tinuvin 765, Tinuvin 780, Tinuvin 905, Tinuvin 5100, Tinuvin 5050, 5060, Tinuvin 5151, Chimassorb 119FL, Chimassorb 944FL, Chimassorb 944LD, Adeka Stab LA-52, Adeka Stab LA-57, Adeka Stab LA-62, Adeka Stab LA-67, Adeka Stab LA-63P, Adeka Stab LA-68LD, Adeka Stab LA-77, Adeka Stab LA-82 and Adeka Stab LA-87; Cyasorb UV-3346 available from Cytec Industries Inc.; and Goodlight UV-3034 available from Goodrich Corporation. "Chimassorb" is a trade name of Ciba Japan K. K.

Examples of the antioxidant include Adeka Stab AO-20, AO-30, AO-40, AO-50, AO-60 and AO-80 available from Adeka Corporation; Sumilizer BHT, Sumilizer BBM-S and Sumilizer GA-80 available from Sumitomo Chemical Co., Ltd.; and Irganox 1076, Irganox 1010, Irganox 3114 and Irganox 245 available from Ciba Japan K. K.

Polymers

In this specification, the polymer of the invention, which is formed by an adjustment of orientation of the polymerizable liquid crystal composition and by its polymerization, is referred to as "the anisotropic polymer". The anisotropic polymer is formed as follows. First, the polymerizable liquid crystal composition that has been diluted with a solvent is applied to a supporting substrate, the surface of which has been treated with a rubbing method or a light-orientation method utilizing polarized light, and then is dried, giving a paint film in which the liquid crystal molecules are oriented. Next, the paint film is irradiated with light or is heated, polymerizing the polymerizable liquid crystal composition under liquid crystal conditions and thus fixing nematic orientation. A glass and plastic films are mainly used for the supporting substrate. Examples of the material of the plastic film include polyimide, polyamideimide, polyamide, polyetherimide, polyetheretherketone, polyetherketone, polyketonesulfide, polyethersulfone, polysulfone, polyphenylenesulfide, polyphenyleneoxide, polyethylene terephthalate, polybutylene terephthalate, polyethylene naphthalate, polyacetal, polycarbonate, polyallylate, acrylic resins, polyvinylalcohol, polypropylene, cellulose, triacetylcellulose and its partially saponified products, epoxy resins, phenol resins and cycloolefin-based resins.

The cycloolefin-based resins include norbornene-based resins and cyclopentadiene-based resins. Among these of resins, a resin having no unsaturated bonds or a resin in which an unsaturated bond is hydrogenated is preferably used. Examples include hydrogenated products of a polymer formed by ring-opening polymerization (or copolymerization) of one, or two or more norbornene-based monomers, a polymer formed by addition polymerization (or copolymerization) of one, or two or more norbornene-based monomers, a polymer formed by addition copolymerization of norbornene-based monomer to olefin-based monomer (ethylene, α-olefin and so forth), a polymer formed by addition copolymerization of norbornene-based monomer to cycloolefin-based monomer (cyclopentene, cyclooctene, 5,6-dihydrocyclopentadiene and so forth), and their modified products. Concrete examples include Zeonex, Zeonor (Zeon Corporation), Arton (JSR corporation), Topas (Ticona GmbH), Apel (Mitsui Chemicals, Inc.), Escena (Sekisui Chemical Co., Ltd.) and Optorez (Hitachi Chemical Co., Ltd.).

These plastic films may be a uniaxially stretched film or a biaxially stretched film. These plastic films may be processed with surface treatment such as hydrophilization treatment of corona treatment or plasma treatment or the like, and hydrophobization treatment. A desirable method of hydrophilization treatment is corona treatment or plasma treatment. An especially desirable method is plasma treatment. The plasma treatment may include the method described in JP 2002-226616 A and JP 2002-121648 A. The method of hydrophobization treatment can be employed in order to adjust the polymerizable liquid crystal composition for a homeotropic orientation. The plastic film may have cumulated layers. A metal substrate made of metal such as aluminum, iron and copper, where the surface was marked with slit-like grooves, or a glass substrate such as alkali glass, borosilicate glass and flint glass, where the surface is etched so as to form slits, can also be used instead of the plastic film.

To the supporting substrate such as a glass plate, a plastic film and so forth, alignment treatment such as a rubbing or an irradiation with polarized light, all of which are described above, may be carried out, before the paint film of the polymerizable liquid crystal composition is formed.

In the case of application of the polymerizable liquid crystal composition that is diluted with a solvent, the solvent is removed after the application, and then a layer of the polymerizable liquid crystal composition with a uniform thickness is formed on the supporting substrate. Conditions for the removal of the solvent are not especially limited. The polymerizable liquid crystal composition may be dried until most of the solvent has been removed and the flowability of the paint film has been lost. The solvent can be removed by means of drying in air, drying on a hotplate, drying in an oven, blowing of a warm wind or a hot wind. Nematic orientation in the polymerizable liquid crystal composition in the form of the paint film might have been completed in the drying process of the paint film, depending on the kinds of the compounds and composition ratios employed in the polymerizable liquid crystal composition. In this case, the paint film that has been treated in the drying process can be transferred to a polymerization process without a thermal process that will be described later.

Desirable conditions of the temperature and time employed for thermal treatment, wavelengths of light used for light irradiation, the amount of light from a light source, and so forth depend on the kinds of the compounds used for the polymerizable liquid crystal composition and the composition ratios, the presence or absence of a photopolymerization initiator and its amount, and so forth. Thus, approximate ranges are shown in the conditions that will be explained below.

It is desirable that thermal treatment is carried out under the conditions that the solvent is removed and a uniform orientation of polymerizable liquid crystals is formed. One example of the thermal treatment is that the polymerizable liquid crystal composition in a form of the paint film is heated to a temperature until the paint film exhibits a nematic liquid crystal phase, forming nematic orientation in the paint film. The nematic orientation may be formed by varying the temperature of the paint film within the temperature range in which the polymerizable liquid crystal composition exhibits a nematic liquid crystal phase. In this method, the paint film is heated to a higher temperature within the temperature range, forming nematic orientation roughly in the paint film, and then the paint film is cooled, giving a more ordered orientation. Another example of the thermal treatment is that the polymerizable liquid crystal composition in a form of the paint film is heated over the clearing point (NI) temperature, and then the paint film is cooled until the paint film exhibits a nematic liquid crystal phase, forming nematic orientation in the paint film. In any one of two thermal treatments, the temperature for the thermal treatment is in the range of approximately room temperature to approximately 120° C. The temperature for the thermal treatment is preferably in the range of approximately room temperature to approximately 100° C., more preferably in the range of approximately room temperature to approximately 90° C., most preferably in the range of approximately room temperature to approximately 85° C. The time for the thermal treatment is in the range of approximately 5 seconds to approximately 2 hours. A desirable time is in the range of approximately 10 seconds to approximately 40 minutes, preferably in the range of approximately 20 seconds to approximately 20 minutes. The time for the thermal treatment of five seconds or more is suitable to increase the temperature of the layer of the polymerizable liquid crystal composition to a designated temperature. The time for the thermal treatment of two hours or less is suitable in order not to decrease the productivity. Under these conditions, the polymerizable liquid crystal layer of the invention may be formed.

Nematic orientation of the polymerizable liquid crystal compound that is formed in the polymerizable liquid crystal layer is fixed by polymerization that is caused by irradiation of the compound with light or by heating. Wavelengths of light used for the irradiation are not especially limited. Electron beams, ultraviolet light, visible light, infrared light (heat rays), and so forth can be utilized. Ultraviolet light and visible light may usually be used. Desirable wavelengths are in the range of approximately 150 nm to approximately 500 nm. More desirable wavelengths are in the range of approximately 250 nm to approximately 450 nm and most desirable wavelengths are in the range of approximately 300 nm to approximately 400 nm. Examples of a light source include a low-pressure mercury lamp (a germicidal lamp, a chemical fluorescent lamp and a black light), a high-pressure discharge lamp (a high-pressure mercury lamp and a metal halide lamp) and a short-arc lamp (an ultra high-pressure mercury lamp, a xenon lamp and a mercury-xenon lamp). Desirable examples of the light source include a metal halide lamp, a xenon lamp, an ultra high-pressure mercury lamp and a high-pressure mercury lamp. A specific range of wavelengths (or a specific wavelength) of light for irradiation may be selected by passing through a filter arranged between the light source and the polymerizable liquid crystal layer. A desirable amount of light is in the range of approximately 2 to approximately 5,000 mJ/cm$^2$. A more desirable amount is in the range of approximately 10 to approximately 3,000 mJ/cm$^2$. The most desirable amount is in the range of approximately 100 to approximately 2,000 mJ/cm$^2$. It is desirable that the temperature during irradiation of light is the same with that of the thermal treatment. It is desirable that the temperature during thermal polymerization is set in consideration of the thermal decomposition temperature of a thermal polymerization initiator. Photopolymerization or thermal polymerization may be carried out under an atmosphere of nitrogen or an inert gas, or in air, and an atmosphere of nitrogen or an inert gas is desirable in view of increasing hardenability.

When the anisotropic polymer is used for a variety of optical element or for an optical compensation element of a liquid crystal display device, an adjustment of distribution of tilt angles in the thickness direction becomes quite important.

One of methods for adjustments of the tilt angle of the anisotropic polymer is that the kinds of a liquid crystal compound and the composition ratios of the polymerizable liquid crystal composition are varied. The tilt angle can be adjusted by the addition of a surfactant to the polymerizable liquid crystal compound. The tilt angle can also be adjusted by the kinds of the solvent, the concentration of the solute, the kinds and the amount of surfactant in the polymerizable liquid crystal composition. The tilt angle can also be adjusted by the kinds of the supporting substrate, conditions of alignment treatment, drying conditions or thermal treatment conditions of the paint film and so forth. The tilt angle is also influenced by the atmosphere and the temperature during irradiation in the photopolymerization process that is carried out after orientation. That is to say, it seems that almost all conditions of the production process of the anisotropic polymer, greatly or slightly, influences the tilt angle. Thus, objective tilt angle can be attained by means of a suitable selection of many conditions for the production process of the anisotropic polymer, along with an optimization of the polymerizable liquid crystal composition.

In a homogeneous orientation, a tilt angle in the area from a substrate interface to an air surface is uniformly close to 0 degrees, and is distributed in the range of 0 degrees to 5 degrees. The orientation is formed by use of the compound (M1), the compound (M2-1) to the compound (M2-5), the compound (M3), the compound (M4) and a non-ionic surfactant. When the compound (M5) is used for adjusting physical properties, the amount thereof should be minimized. Desirable examples of the non-ionic surfactant include fluorine-based, silicone-based and hydrocarbon-based non-ionic surfactants, and the fluorine-based non-ionic surfactant is more desirable. The ratio of the surfactant is in the range of approximately 0.0001 to approximately 0.03 by weight, and preferably in the range of approximately 0.0003 to approximately 0.02, based on the total weight of the composition (1) (excluding the solvent).

Suitable thickness of the anisotropic polymer depends on the value of the retardation or the optical anisotropy (birefringence) of the anisotropic polymer. Generally, the thickness of the anisotropic polymer is preferably in the range of approximately 0.05 to 50 μm, more preferably in the range of 0.5 to 20 μm, and most preferably in the range of 1 to 10 μm. The haze value of the anisotropic polymer is preferably 1.5% or less, and more preferably 1.0% or less. The transmittance is preferably 80%, and more preferably 95% or more. It is desirable that the transmittance satisfies these conditions in the visible light region.

The anisotropic polymer is useful for an optical compensation element utilized for a liquid crystal display element (especially for a liquid crystal display element of an active matrix type and a passive matrix type). Examples of the type of the liquid crystal display element that is suitable for the use of the anisotropic polymer as an optical compensation film include a VA mode (vertically aligned), an IPS mode (in-plane switching), an OCB mode (optically compensated birefringence), a TN mode (twisted nematic), a STN mode (super twisted nematic), an ECB mode (electrically controlled birefringence), a DAP mode (deformation of aligned phases), a CSH mode (color super homeotropic), a VAN/VAC mode (vertically aligned nematic/cholesteric), a HAN mode (hybrid aligned nematic), an OMI mode (optical mode interference) and a SBE mode (super birefringence effect). Furthermore, the anisotropic polymer can be used as a phase retarder for a display element, such as a guest-host mode, a ferroelectric mode, an antiferroelectric mode, a reflection type, a reflection type and a semi-transmission type. Incidentally, optimum values of the parameters of the film thickness or the distribution of tilt angles in the thickness direction that is required for the anisotropic polymer are different depending on the kinds of the liquid crystal display element, since they depend greatly on the kinds of the element compensated and its optical parameter.

The anisotropic polymer can be used as an optical element unified with a polarizing plate and so forth. In this case, the anisotropic polymer is arranged outside of the liquid crystal cell. It is possible to arrange the anisotropic polymer inside of the liquid crystal cell, because of no or less elution of impurities to the liquid crystals in the cell. The function of a color filter can be improved by the formation of the layer of the anisotropic polymer on the color filter by applying the method disclosed, for example, in JP 2006-350294 A.

When the polymerizable liquid crystal composition includes an optically active compound that is polymerizable or non-polymerizable, the anisotropic polymer has a helical structure that is fixed.

The anisotropic polymer in which the helical structure is fixed is suitable for use as an optical retardation film, a polarizer, a circularly polarized light element, an elliptically polarized light element, an antireflection film, a selective reflection film, a color compensation film and a viewing angle-compensation film.

Thermal polymerization or photopolymerization is suitable for the fixation of the helical structure. It is desirable that the thermal polymerization is carried out in the presence of a thermal radical initiator or a cationic polymerization initiator. For example, a polymer in which molecules are arranged in the direction of polarized light is formed by polymerization in the presence of a cationic photopolymerization initiator under irradiation with ultraviolet light, electron beams or the like. Such a polymer can be used for a liquid crystal alignment film and so forth, without rubbing treatment.

The anisotropic polymer in which the helical structure is fixed is formed by polymerization of the polymerizable liquid crystal composition including the optically active compound that is polymerizable or non-polymerizable also on a supporting substrate processed with rubbing treatment, photo-alignment treatment or drawing treatment. The characteristics of the anisotropic polymer having a helical structure depend on the helical pitch of the helical structure. The helical pitch can be adjusted with the kinds and the amount of the optically active compounds. The ratio of the optically active compound is usually in the range of approximately 0.0001 to approximately 0.5 by weight, and preferably in the range of approximately 0.01 to approximately 0.3 by weight based on the total weight of the polymerizable liquid crystal composition (excluding the solvent). Only one optically active compound may be added, and the helical pitch can be adjusted by the addition of the plurality of optically active compounds.

The polymer (1) in which both molecular arrangement and a helical structure are not fixed is suitable for an antireflection film, a liquid crystal alignment film and so forth. In any case, it is also utilized for adhesives, synthetic polymers having mechanical anisotropy, cosmetics, an ornament, non-linear optical materials, information storage materials and so forth.

The anisotropic polymer can be processed to a film and so forth by dissolving it in a solvent. The anisotropic polymer may be processed by mixing with another polymer or laminated to another polymer. Desirable solvents include N-methyl-2-pyrrolidone, dimethylsulfoxide, N,N-dimethylacetoamide, N,N-dimethylformamide, N,N-dimethylacetoamide dimethyl acetal, tetrahydrofuran, chloroform, 1,4-dioxane, bis(methoxyethyl)ether, γ-butyrolactone, tetramethylurea, trifluoroacetic acid, ethyl trifluoroacetate, hexafluoro-2-propanol, 2-methoxyethylacetate, methyl ethyl ketone, cyclopentanone and cyclohexanone. These solvents may be mixed with a conventional solvent such as acetone, benzene, toluene, heptane and methylene chloride.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention is explained by way of the following Examples, but not limited to Examples. The structures of compounds were characterized by means of their nuclear magnetic resonance spectra, infrared spectra, mass spectra and so forth. The transition temperature was expressed in the degree Celsius (° C.), and the symbols C, N and I stand for crystals, a nematic phase and an isotropic liquid phase, respectively. A parenthesized value shows that the phase transition is monotropic. Methods of measurement are as follows.
Conditions of Polymerization A sample was irradiated with light at an intensity of 30 mW/cm$^2$ (365 nm) for 30 seconds at room temperature under an atmosphere of nitrogen or in air by use of a 250 W ultra high-pressure mercury lamp.
Pre-Treatment of Glass Substrates An alignment reagent (trade name: Lixon AlignerPIA-5370; Chisso Corporation) was spin-coated on a glass plate (1.1 mm thickness). After the solvent had been dried, the glass plate was burned at 210° C. for 30 minutes, and then the surface was processed with the rubbing treatment. This glass plate was used as a glass substrate, and a liquid crystal film was prepared on it.
Confirmation of Liquid Crystal Orientation The presence or absence of orientational defects in a liquid crystal film on a substrate was observed with a polarized optical microscope.

Measurement with a Polarimeter

An Optipro polarimeter made by Shintech, Inc. was used. A liquid crystal film on a substrate was irradiated with light of wavelength at 550 nm. Retardation (Δn×d) was measured while the angle of incidence of light to the film surface was decreased from 90 degrees. Retardation (delay of phases) is expressed as Δn×d, where the symbol Δn stands for the optical anisotropy, and the symbol d stands for polymer film thickness.

Measurement of Film Thickness

The film thickness of a liquid crystal film on a glass substrate was measured with KLA-Tencor Surface Properties Measuring System, Model Alpha-step IQ (Tencor Corporation).

Evaluation of the Optical Anisotropy (Δn)

The optical anisotropy was calculated from the equation of "retardation/film thickness" using values of retardation and film thickness measured for a liquid crystal film having a homogeneous orientation.

Confirmation of Wavelengths of Selective Reflection

Transmission spectrum of a film that has ability of selective reflection was measured with an UV-VIS-NIR Spectrophotometer Model V-670 (Jasco Corporation). The selective reflection region was indicated by the wavelength width of transmittance located in the center of the maximum transmittance and the minimum transmittance. The central wavelength of the selective reflection was indicated by the central value of the wavelength width.

Example 1

The following compound (1-A-10) was prepared as follows.

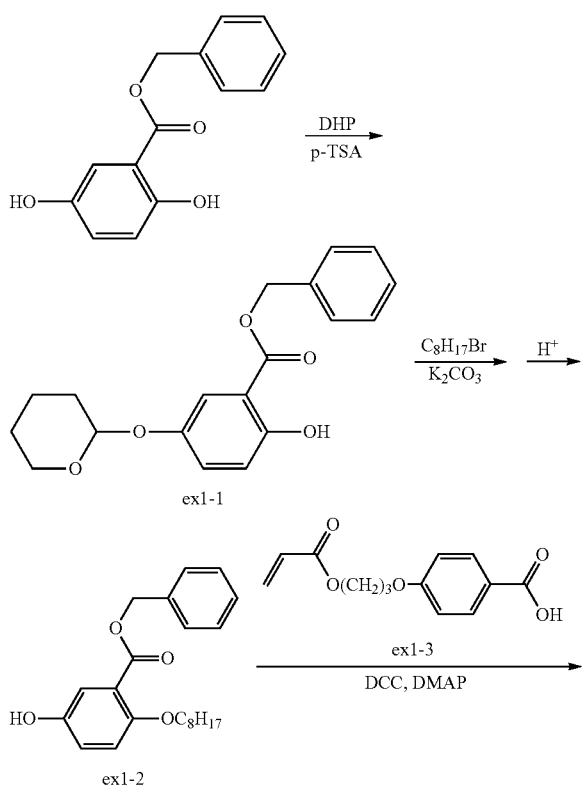

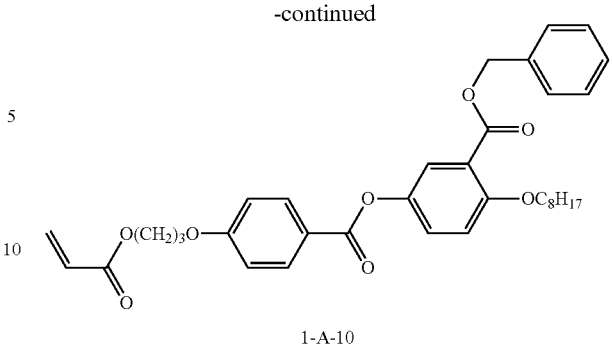

1-A-10

First Step:

Benzyl 2,5-dihydrobenzoate (85 mmol), 3,4-dihydro-2H-pyran (DHP; 130 mmol) and p-toluenesulfonic acid (10 mmol) were added to dichloromethane (300 mL) and the mixture was stirred under an atmosphere of nitrogen at 50° C. for 5 hours. The organic phase was washed with water and dried over anhydrous sulfate. The solvent was distilled off under reduced pressure and the residue was purified by means of column chromatography and recrystallization from heptane, giving the compound (ex1-1) (32 mmol).

Second Step:

The compound (ex1-1) (32 mmol), bromobutane (38 mmol) and potassium carbonate (38 mmol) were added to 2-butanone (350 ml) and the mixture was heated to reflux under an atmosphere of nitrogen for 5 hours. Toluene and water were added to the mixture and the organic phase was washed with water. The solvent was distilled off under reduced pressure. 3N-Hydrochloric acid and acetone (350 ml) were added to the residue and the mixture was stirred at room temperature for 1 hours. Ethyl acetate was added thereto and the organic phase was washed with water, and then dried over anhydrous sulfate. The solvent was distilled off under reduced pressure and the residue was recrystallized from heptane, giving the compound (ex1-2) (28 mmol).

Third Step:

The compound (ex1-2) (28 mmol), the compound (ex1-3) (65 mmol) and 4-dimethylaminopyridine (DMAP; 16 mmol) were added to dichloromethane (150 ml) and the mixture was stirred under an atmosphere of nitrogen. 1,3-Dicyclohexylcarbodiimide (DCC; 560 mmol) in dichloromethane (100 ml) solution was added dropwise thereto and the stirring was continued at room temperature for another 8 hours. Precipitates were filtered off and the organic phase was washed with water, and then dried over anhydrous sulfate. The solvent was distilled off under reduced pressure. The residue was purified by means of column chromatography and recrystallization from ethanol, giving the compound (1-A-10) (17 mmol).

Example 2

The following the compound (1-B-10) was prepared as follows.

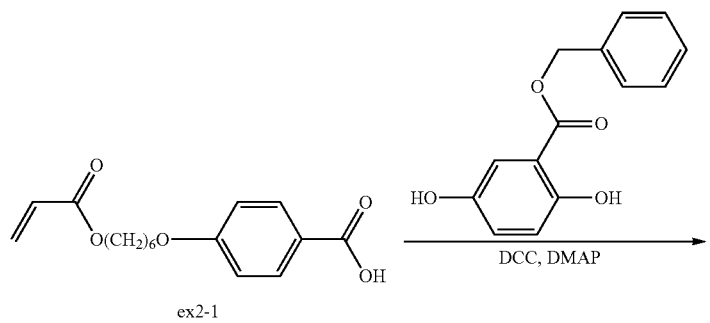

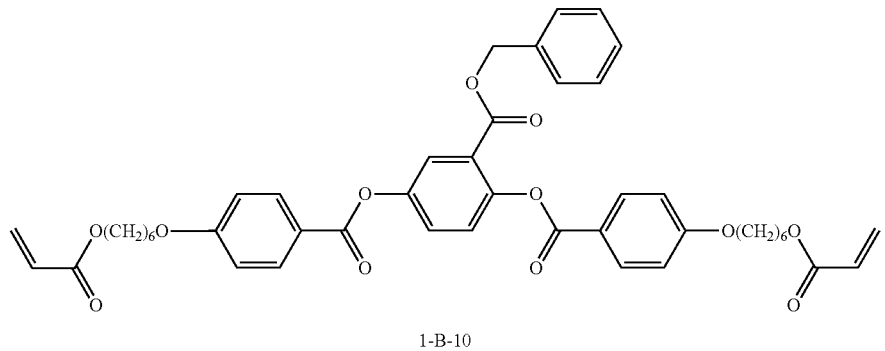

The compound (ex2-1) (74 mmol), benzyl 2,5-dihydrobenzoate (35 mmol) and 4-dimethylaminopyridine (DMAP; 21 mmol) were added to dichloromethane (200 mL), and the mixture was stirred under an atmosphere of nitrogen. 1,3-Dicyclohexylcarbodiimide (DCC; 74 mmol) in dichloromethane (100 mL) solution was added dropwise thereto. After the addition, the stirring was continued at room temperature for another 8 hours. Precipitates were filtered off and the organic phase was washed with water, and then dried over anhydrous sulfate. The solvent was distilled off under reduced pressure. The residue was purified by means of column chromatography and recrystallization from ethanol, giving the compound (1-B-10) (16 mmol). The melting point of the resultant compound (1-B-10) was as follows.

Phase transition temperature: C 79 (N 65) I.

Compounds used in Examples 3 to 17 are shown below.

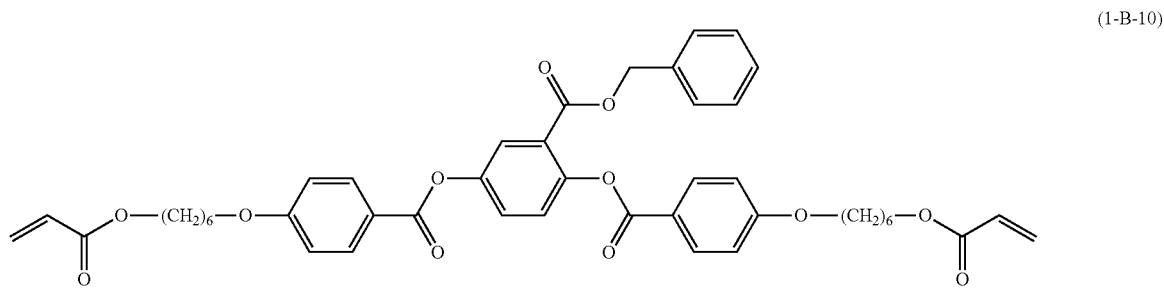

(1-B-10)

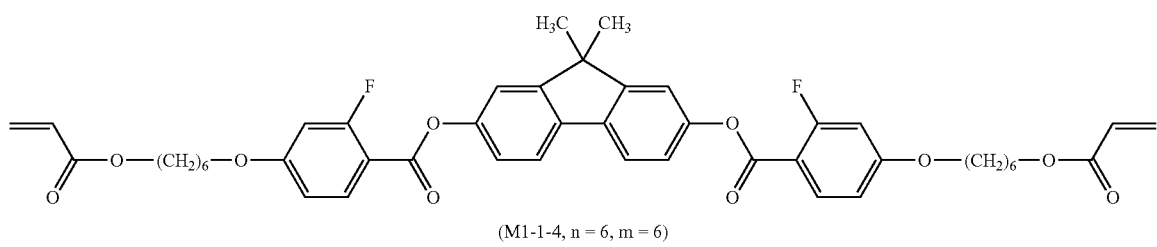

(M1-1-4, n = 6, m = 6)

-continued
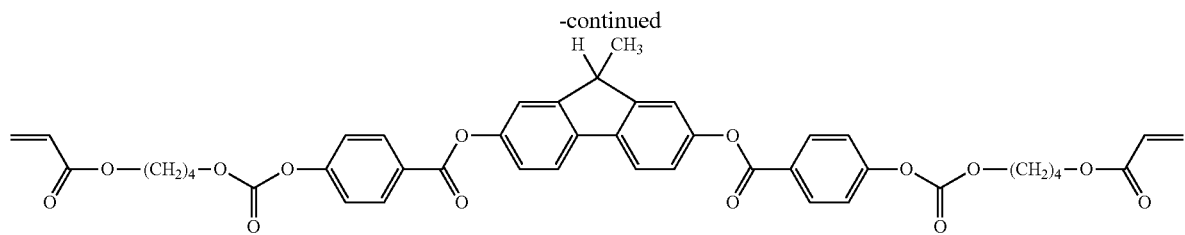
(M1-1-7, n = 4, m = 4)
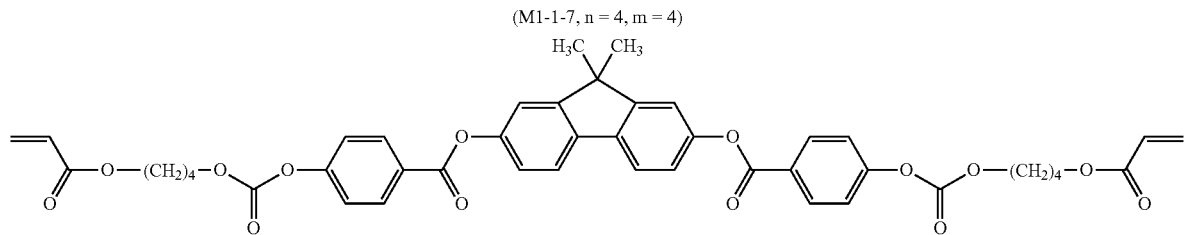
(M1-1-8, n = 4, m = 4)
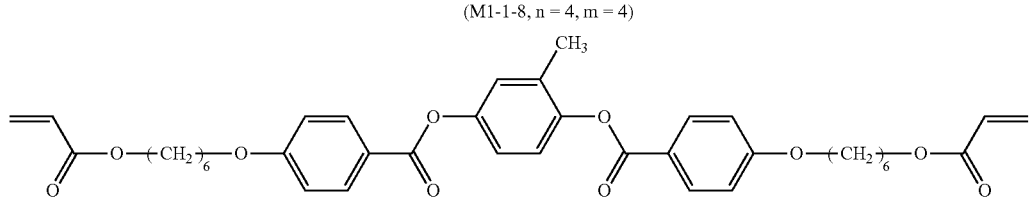
(M2-1-2-1, n = 6, m = 6)
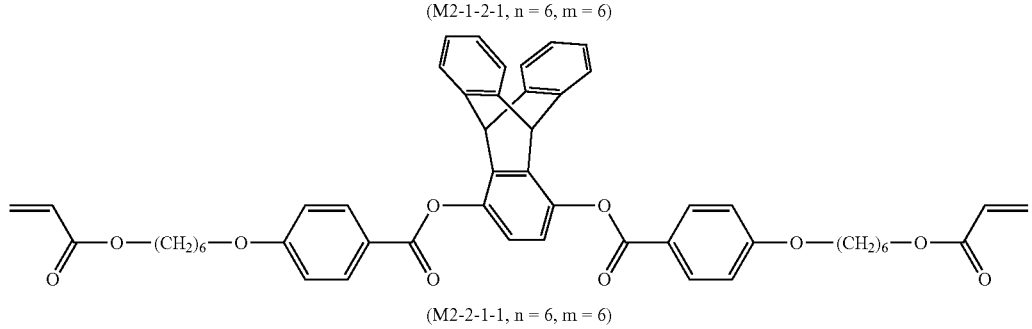
(M2-2-1-1, n = 6, m = 6)
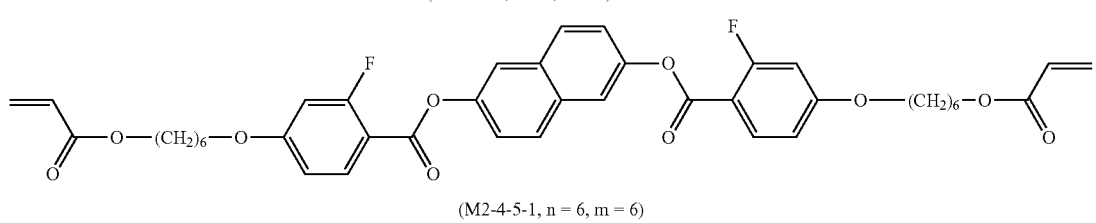
(M2-4-5-1, n = 6, m = 6)
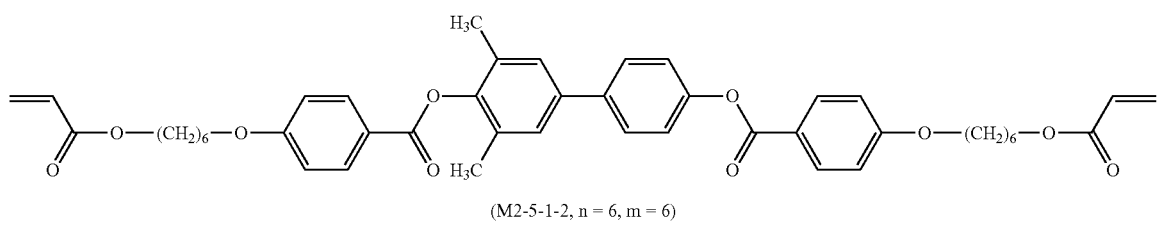
(M2-5-1-2, n = 6, m = 6)
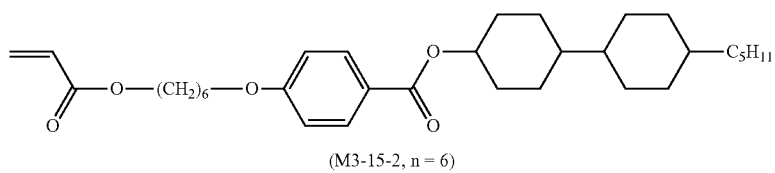
(M3-15-2, n = 6)

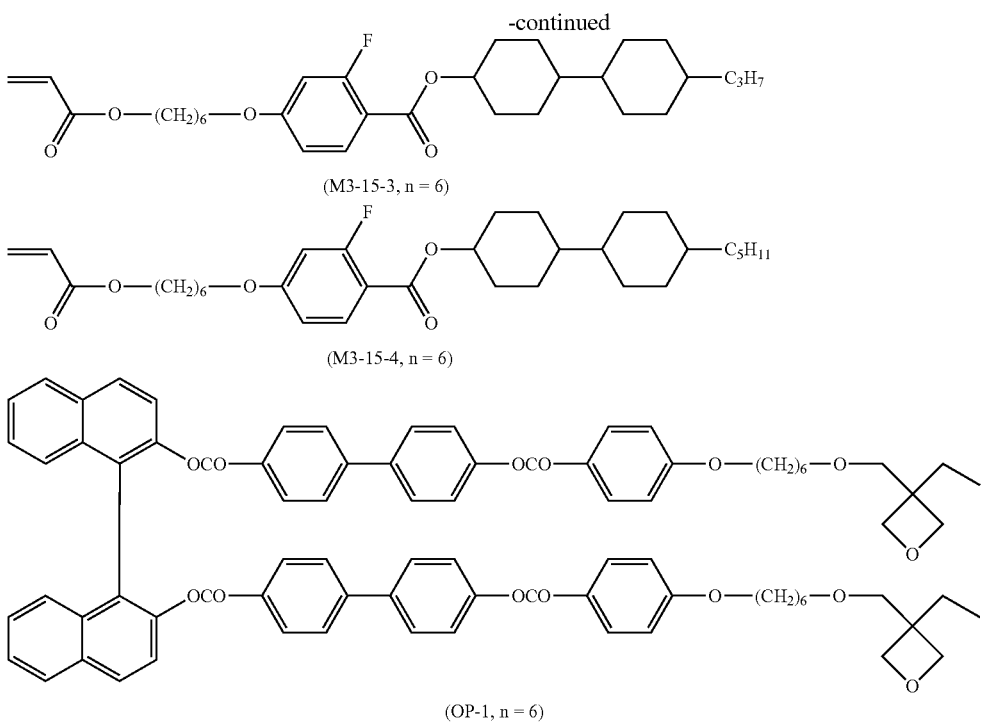

(M3-15-3, n = 6)

(M3-15-4, n = 6)

(OP-1, n = 6)

The compound (M1-1-4) and the compound (M2-4-5-1) were prepared by a method similar to that described in JP 2006-307150 A.

The compound (M1-1-7) and the compound (M1-1-8) were prepared by the method described in WO 2008/136265 A. The compound (M2-1-2-1) was prepared by the method described in Makromol. Chem., 190, 2255-2268 (1989). The compound (M2-2-1-1) was prepared according to the method described in JP 2006-111571 A. The compound (M3-15-2) was prepared by the method described in WO 97/034862 A.

The compound (M3-15-3) and the compound (M3-15-4) were prepared by a combination of the methods described in WO 97/034862 and JP 2006-307150 A. OP-1 was prepared according to the method described in JP 2005-263778A. Incidentally, a photopolymerization initiator Irgacure 907 and Irgacure 369 which were employed in Examples and Comparative Examples were commercial products of Ciba Japan K. K. as described above.

Incidentally, the compound (M2-5-1-2) was prepared as follows.

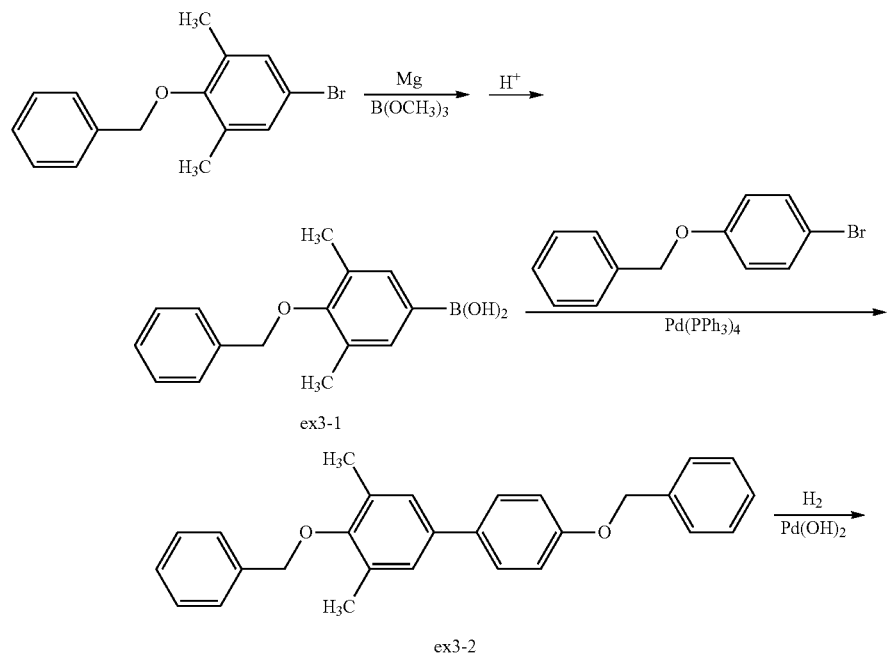

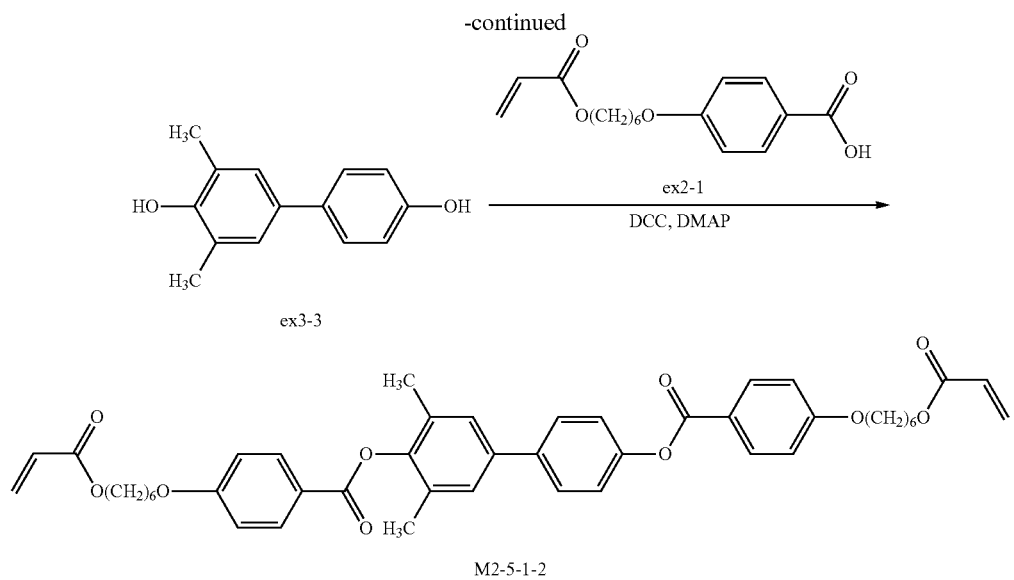

First Step:

2-Benzyloxy-5-bromo-1,3-dimethylbenzene (68.7 mmol) and magnesium (75.5 mmol) were added to tetrahydrofuran (50 mL), and the Grignard reagent was prepared with stirring under an atmosphere of nitrogen at 50° C. for 2 hours. To the reagent cooled at −10° C., trimethylborate (96.0 mmol) was added dropwise and the stirring was continued for another 1 hour. 6N-Hydrochloric acid (50 mL) was added dropwise to the mixture and ethyl acetate was added, separating an organic phase. The organic phase was washed with water, and then dried over anhydrous sulfate. The solvent was distilled off under reduced pressure. Recrystallization from toluene gave the compound (ex3-1) (36.7 mmol).

Second Step:

The compound (ex3-1) (36.7 mmol), 1-benzyloxy-4-bromobenzene (36.1 mmol), 2M-aqueous solution of sodium carbonate (36 mL) and tetrakis(triphenylphosphine)palladium (1.04 mmol) were added to ethylene glycol dimethyl ether (90 mL), and the mixture was heated to reflux with stirring under an atmosphere of nitrogen for 8 hours. Water was added to thereto and crystals deposited were filtered. Recrystallization from acetone gave the compound (ex3-2) (22.6 mmol).

Third Step:

The compound (ex3-2) (22.6 mmol) and palladium hydroxide (2.85 mmol) were added to tetrahydrofuran (100 mL) and the mixture was stirred under an atmosphere of hydrogen at room temperature for 8 hours. Palladium hydroxide was filtered off and the solvent was distilled off under reduced pressure, giving the compound (ex3-3) (20.1 mmol).

Fourth Step:

The compound (ex3-3) (2.33 mmol), the compound (eX2-1) (5.13 mmol) and 4-dimethylaminopyridine (DMAP; 0.41 mmol) were added to dichloromethane (10 mL), and the mixture was stirred under an atmosphere of nitrogen. N,N'-Dicyclohexylcarbodiimide (DCC; 5.36 mmol) in dichloromethane (5 mL) solution was added dropwise to the mixture. After the addition, the stirring was continued at room temperature for another 8 hours. Precipitates were filtered off and the organic phase was washed with water, and then dried over anhydrous sulfate. The solvent was distilled off under reduced pressure. The residue was purified by means of column chromatography and recrystallization from ethanol, giving the compound (M-2-5-1-2) (0.52 mmol). The melting point of the resultant compound (M2-5-1-2) was as follows.

Phase transition temperature: C 79 N. The clearing point (NI) could not be measured because of polymerization.

Example 3

Preparation of the Polymerizable Liquid Crystal Compound (1)

A composition was prepared by mixing the compound (1-B-10)/the compound (M2-1-2-1)/the compound (M2-2-1-1) in a weight ratio of 34/23/43. The composition was referred to as MIX-1. To the MIX-1, a fluorine-based nonionic surfactant (Neos Company Limited; trade name: Futargent FTX-218) in a weight ratio of 0.002 and a photopolymerization initiator Irgacure 907 (Ciba Japan K. K.) in a weight ratio of 0.03 were added. Cyclopentanone/PGMEA in a weight ratio of 1/1 was added to the composition, giving the polymerizable liquid crystal composition (1) in which the ratio of the solvent was 75% by weight. Incidentally, PGMEA is an abbreviation of propylene glycol monomethyl ether acetate.

Next, the polymerizable liquid crystal composition (1) was applied to a glass substrate, on which an alignment film was coated and rubbed, by means of spin coating. The substrate was heated at 80° C. for 3 minutes, and then cooled for 3 minutes at room temperature. The paint film from which the solvent had been removed was polymerized under irradiation with ultraviolet light under a stream of nitrogen, giving the anisotropic polymer in which the orientation of the liquid crystals was fixed. The anisotropic polymer had no orientational defects and a uniform orientation, when observed with a polarizing microscope. It was found that the anisotropic polymer had a homogeneous orientation since the results shown in FIG. 1 were obtained by the measurement on the retardation of the polymer. Measured value of the retardation at 90 degrees against the film plane was 137 nm and the film thickness was 1,160 nm, and thus calculations showed that the optical anisotropy ($\Delta n$) was 0.12.

Comparative Example 1

A composition was prepared by mixing the compound (M2-1-2-1)/the compound (M2-2-1-1) in a weight ratio of 35/65. The composition was referred to as MIX-2. A polymer was obtained from the polymerizable liquid crystal composition (2) that was prepared in the same way as described in Example 3 using the MIX-2 instead of the MIX-1. An evaluation revealed that the polymer had many orientational defects that were caused by crystallization and the surface was milky white. The retardation of the polymer could hardly be evaluated.

Example 4

A composition was prepared by mixing the compound (1-B-10)/the compound (M2-2-1-1)/the compound (M3-15-2) in a weight ratio of 34/43/23. The composition was referred to as MIX-3. A polymer was obtained from the polymerizable liquid crystal composition (3) that was prepared in the same way as described in Example 3 using the MIX-3 instead of the MIX-1. An evaluation revealed that the polymer had a uniform orientation without orientational defects. It was found that the polymer had a homogeneous orientation since the results of measurement on the retardation of the anisotropic polymer showed a similar tendency to that in FIG. 1, and calculations showed that the optical anisotropy ($\Delta n$) was 0.11.

Comparative Example 2

A composition was prepared by mixing the compound (M2-2-1-1)/the compound (M3-15-2) in a weight ratio of 65/35. The composition was referred to as MIX-4. A polymer was obtained from the polymerizable liquid crystal composition (4) that was prepared in the same way as described in Example 3 using the MIX-4 instead of the MIX-1. An evaluation revealed that the polymer had many orientational defects that were caused by crystallization and the surface was milky white. The retardation of the polymer was hardly evaluated.

Example 5

A composition was prepared by mixing the compound (1-B-10)/the compound (M1-1-7)/the compound (M1-1-8) in a weight ratio of 33/34/34. The composition was referred to as MIX-5. A polymer was obtained from the polymerizable liquid crystal composition (5) that was prepared in the same way as described in Example 3 using the MIX-5 instead of the MIX-1. An evaluation revealed that the polymer had a uniform orientation without orientational defects. It was found that the polymer had a homogeneous orientation since the results of measurement on the retardation of the anisotropic polymer showed a similar tendency to that in FIG. 1, and calculations showed that the optical anisotropy ($\Delta n$) was 0.16.

Example 6

A composition was prepared by mixing the compound (1-B-10)/the compound (M1-1-7)/the compound (M1-1-8) in a weight ratio of 66/17/17. The composition was referred to as MIX-6. A polymer was obtained from the polymerizable liquid crystal composition (6) that was prepared in the same way as described in Example 3 using the MIX-6 instead of the MIX-1. An evaluation revealed that the polymer had a uniform orientation without orientational defects. It was found that the polymer had a homogeneous orientation since the results of measurement on the retardation of the anisotropic polymer showed a similar tendency to that in FIG. 1, and calculations showed that the optical anisotropy ($\Delta n$) was 0.13.

Comparative Example 3

A composition was prepared by mixing the compound (M1-1-7)/the compound (M1-1-8) in a weight ratio of 50/50. The composition was referred to as MIX-7. A polymer was obtained from the polymerizable liquid crystal composition (7) that was prepared in the same way as described in Example 3 using the MIX-7 instead of the MIX-1. An evaluation revealed that the polymer had many orientational defects that were caused by crystallization and the surface was milky white. The retardation of the polymer was hardly evaluated.

Example 7

A composition was prepared by mixing the compound (1-B-10)/the compound (M1-1-4)/the compound (M2-2-1-1) in a weight ratio of 20/35/45. The composition was referred to as MIX-8. A polymer was obtained from the polymerizable liquid crystal composition (8) that was prepared in the same way as described in Example 3 using the MIX-8 instead of the MIX-1. An evaluation revealed that the polymer had a uniform orientation without orientational defects. It was found that the polymer had a homogeneous orientation since the results of measurement on the retardation of the anisotropic polymer showed a similar tendency to that in FIG. 1, and calculations showed that the optical anisotropy ($\Delta n$) was 0.12.

Comparative Example 4

A composition was prepared by mixing the compound (M1-1-4)/the compound (M2-2-1-1) in a weight ratio of 35/65. The composition was referred to as MIX-9. A polymer was obtained from the polymerizable liquid crystal composition (9) that was prepared in the same way as described in Example 3 using the MIX-9 instead of the MIX-1. An evaluation revealed that the polymer had many orientational defects that were caused by crystallization and the surface was milky white. The retardation of the polymer could hardly be evaluated.

Example 8

A composition was prepared by mixing the compound (1-B-10)/the compound (M2-4-5-1)/the compound (M2-2-1-1) in a weight ratio of 50/25/25. The composition was referred to as MIX-10. A polymer was obtained from the polymerizable liquid crystal composition (10) that was prepared in the same way as described in Example 3 using the MIX-10 instead of the MIX-1 and using a polymerization initiator Irgacure 369 (Ciba Japan K. K.) instead of Irgacure 907. An evaluation revealed that the polymer had a uniform orientation without orientational defects. It was found that the polymer had a homogeneous orientation since the results of measurement on the retardation of the anisotropic polymer showed a similar tendency to that in FIG. 1, and calculations showed that the optical anisotropy ($\Delta n$) was 0.14.

Comparative Example 5

A composition was prepared by mixing the compound (M2-4-5-1)/the compound (M2-2-1-1) in a weight ratio of 50/50. The composition was referred to as MIX-11. A polymer was obtained from the polymerizable liquid crystal composition (11) that was prepared in the same way as described in Example 8 using the MIX-11 instead of the MIX-10. An evaluation revealed that the polymer had many orientational defects that were caused by crystallization and the surface was milky white. The retardation of the polymer could hardly be evaluated.

Example 9

A composition was prepared by mixing the compound (1-B-10)/the compound (M2-5-1-2)/the compound (M2-2-1-1) in a weight ratio of 34/23/43. The composition was referred to as MIX-12. A polymer was obtained from the polymerizable liquid crystal composition (12) that was prepared in the same way as described in Example 8 using the MIX-12 instead of the MIX-10 and using cyclopentanone/PGMEA in a weight ratio of 7/3 instead of cyclopentanone/PGMEA in a weight ratio of 1/1. An evaluation revealed that the polymer had a uniform orientation without orientational defects. It was found that the polymer had a homogeneous orientation since the results of measurement on the retardation of the anisotropic polymer showed a similar tendency to that in FIG. 1, and calculations showed that the optical anisotropy ($\Delta n$) was 0.13.

Comparative Example 6

A composition was prepared by mixing the compound (M2-5-1-2)/the compound (M2-2-1-1) in a weight ratio of 35/65. The composition was referred to as MIX-13. A polymer was obtained from the polymerizable liquid crystal composition (13) that was prepared in the same way as described in Example 9 using the MIX-13 instead of the MIX-12. An evaluation revealed that the polymer many orientational defects that were caused by crystallization and the surface was milky white. The retardation of the polymer could hardly be evaluated.

Example 10

A polymer was obtained from the polymerizable liquid crystal composition (14) that was prepared in the same way as described in Example 3, except that a polymerizable optically active compound Paliocolor LC-756 (BASF Japan Ltd.) in a weight ratio of 0.07 was further added to the MIX-1. An evaluation revealed that the anisotropic polymer had the selective reflection of blue light and a uniform planar orientation without orientational defects. The central wavelength of the selective reflection was 465 nm, and the wavelength width was about 55 nm.

Example 11

A polymer was obtained from the polymerizable liquid crystal composition (15) that was prepared in the same way as described in Example 3, except that a polymerizable optically active compound Paliocolor LC-756 (BASF Japan Ltd.) in a weight ratio of 0.05 was further added to the MIX-1. An evaluation revealed that the anisotropic polymer had the selective reflection of red light and a uniform planar orientation without orientational defects. The central wavelength of the selective reflection was 635 nm, and the wavelength width was about 80 nm.

Example 12

Figure 2:
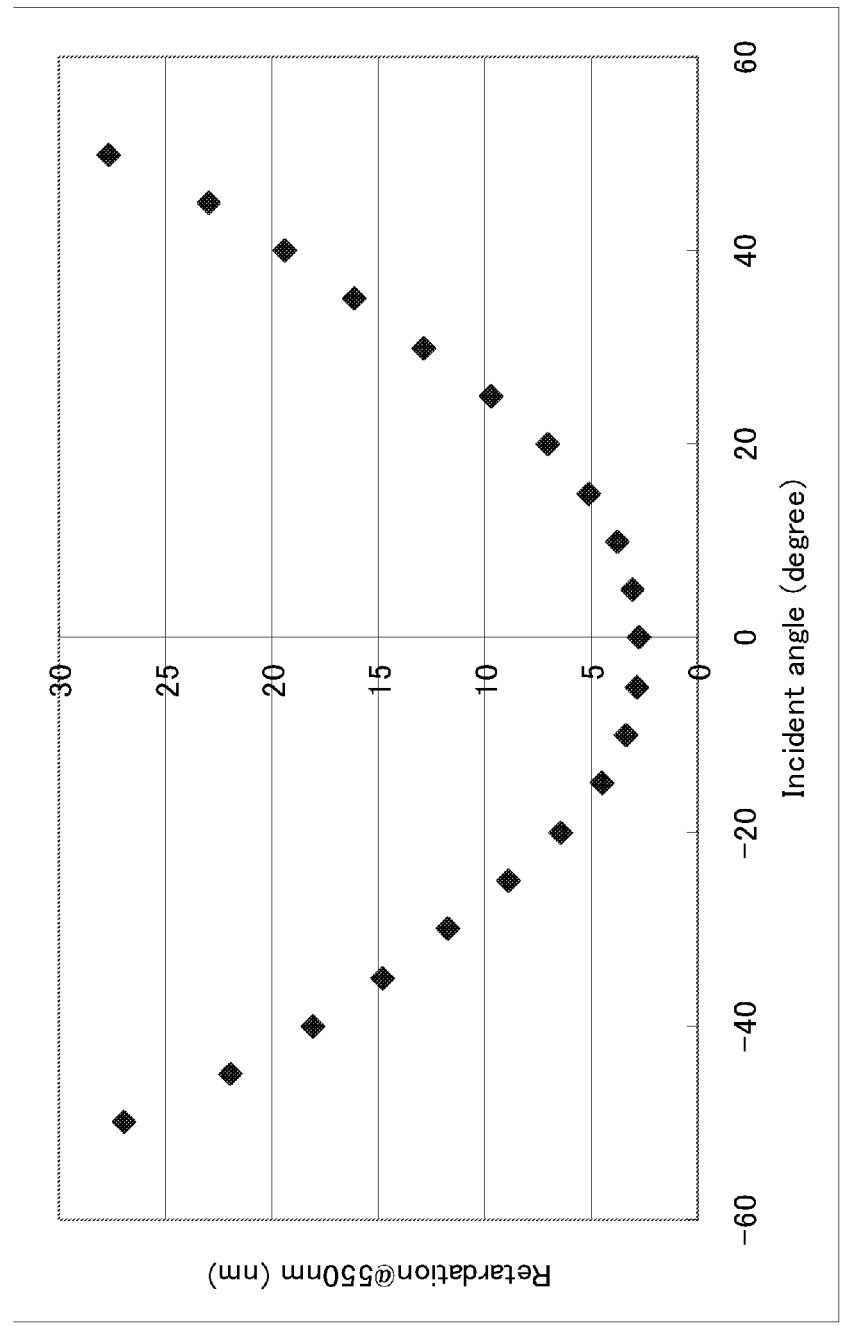
FIG. 2: Results of measurement on the retardation of the anisotropic polymer in Example 12.

A polymer was obtained from the polymerizable liquid crystal composition (16) that was prepared in the same way as described in Example 3, except that the polymerizable optically active compound (OP-1) in a weight ratio of 0.06, a photopolymerization initiator Irgacure 907 in a weight ratio of 0.03 and a polymerization initiator CPI-110P (San-Apro Ltd.) in a weight ratio of 0.01 were further added to the MIX-1. An evaluation revealed that the anisotropic polymer had a twisted orientation without orientational defects. It was found that the anisotropic polymer had negative C-plates since the results shown in FIG. 2 were obtained by the measurement on the retardation of the polymer.

Example 13

A polymer was obtained from the polymerizable liquid crystal composition (17) that was prepared in the same way as described in Example 12, except that the polymerizable optically active compound (OP-1) in a weight ratio of 0.03 was added to the MIX-1 instead of the polymerizable optically active compound (OP-1) in a weight ratio of 0.06. An evaluation revealed that the anisotropic polymer had the selective reflection of red light and a uniform planar orientation without orientational defects. The central wavelength of the selective reflection was 625 nm, and the wavelength width was about 80 nm.

Example 14

A polymer was obtained from the polymerizable liquid crystal composition (18) that was prepared in the same way as described in Example 12, except that the polymerizable optically active compound (OP-1) in a weight ratio of 0.045 was added to the MIX-1 instead of the polymerizable optically active compound (OP-1) in a weight ratio of 0.06. An evaluation revealed that the anisotropic polymer had the selective reflection of blue light and a uniform planar orientation without orientational defects. The central wavelength of the selective reflection was 455 nm, and the wavelength width was about 50 nm.

Example 15

A polymer was obtained from the polymerizable liquid crystal composition (19) that was prepared in the same way as described in Example 3, except that a polymerizable optically active compound Paliocolor LC-756 (BASF Japan Ltd.) in a weight ratio of 0.04 was further added to the MIX-1. An evaluation revealed that the anisotropic polymer had the selective reflection of near-infrared light and a uniform planar orientation without orientational defects. The central wavelength of the selective reflection was 800 nm, and the wavelength width was about 150 nm.

Example 16

A composition was prepared by mixing the compound (1-B-10)/the compound (M2-1-2-1)/the compound (M3-15-2) in a weight ratio of 45/25/30. The composition was referred to as MIX-14. To the MIX-14, a fluorine-based nonionic surfactant (Neos Company Limited; trade name: Futargent FTX-218) in a weight ratio of 0.002 and a photopolymerization initiator Irgacure 907 (Ciba Japan K. K.) in a weight ratio of 0.06 were added. Cyclohexanone was added to the composition, giving the polymerizable liquid crystal composition (20) in which the ratio of the solvent was 75% by weight. The anisotropic polymer was prepared in the same way as described in Example 3, except that the polymerizable liquid crystal composition (20) was polymerized in air instead of polymerization under a stream of nitrogen. An evaluation revealed that the anisotropic polymer had a uniform orientation without orientational defects. It was found that the polymer had a homogeneous orientation since the results of measurement on the retardation of the anisotropic polymer showed a similar tendency to that in FIG. 1, and calculations showed that the optical anisotropy (Δn) was 0.14.

Comparative Example

A composition was prepared by mixing the compound (M2-1-2-1)/the compound (M3-15-2) in a weight ratio of 70/30. The composition was referred to as MIX-15. A polymer was obtained from the polymerizable liquid crystal composition (21) that was prepared in the same way as described in Example 15 using the MIX-15 instead of the MIX-1. An evaluation revealed that the polymer had many orientational defects that were caused by crystallization and the surface was milky white. The retardation of the polymer could hardly be evaluated.

Example 17

A composition was prepared by mixing the compound (1-B-10)/the compound (M2-2-1-1)/the compound (M3-15-4) in a weight ratio of 34/43/23. The composition was referred to as MIX-16. To the MIX-16, a fluorine-based nonionic surfactant (Neos Company Limited; trade name: Futargent FTX-218) in a weight ratio of 0.002 and a photopolymerization initiator Irgacure 907 (Ciba Japan K. K.) in a weight ratio of 0.06 were added. Cyclohexanone was added to the composition, giving the polymerizable liquid crystal composition (22) in which the ratio of the solvent was 75% by weight. The anisotropic polymer was prepared in the same way as described in Example 3, except that the polymerizable liquid crystal composition (22) was polymerized in air instead of polymerization under a stream of nitrogen. An evaluation revealed that the anisotropic polymer had a uniform orientation without orientational defects. It was found that the polymer had a homogeneous orientation since the results of measurement on the retardation of the anisotropic polymer showed a similar tendency to that in FIG. 1, and calculations showed that the optical anisotropy (Δn) was 0.11.

Example 18

The following compound (1-B-47) was prepared as follows.

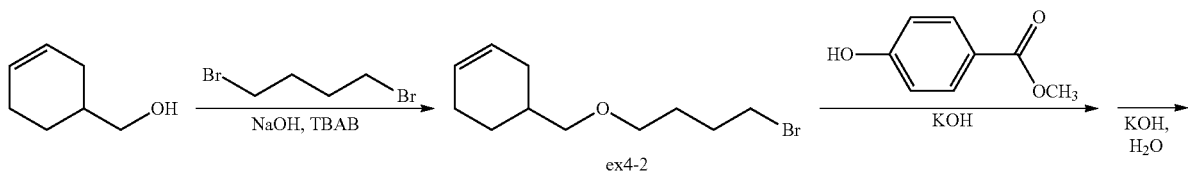

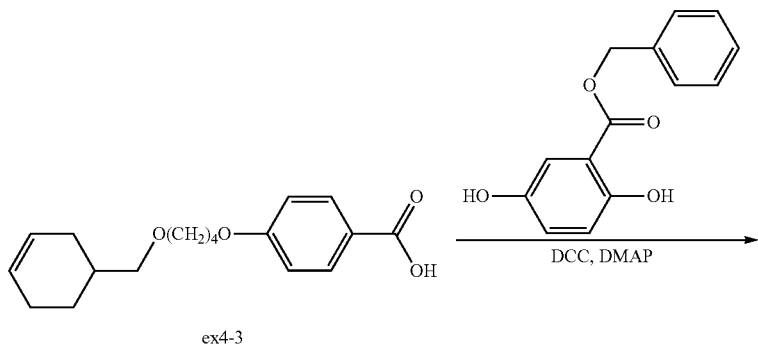

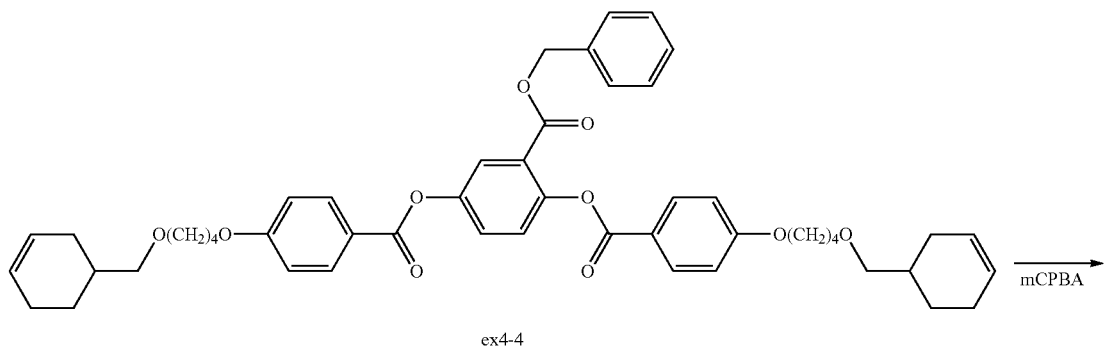

-continued

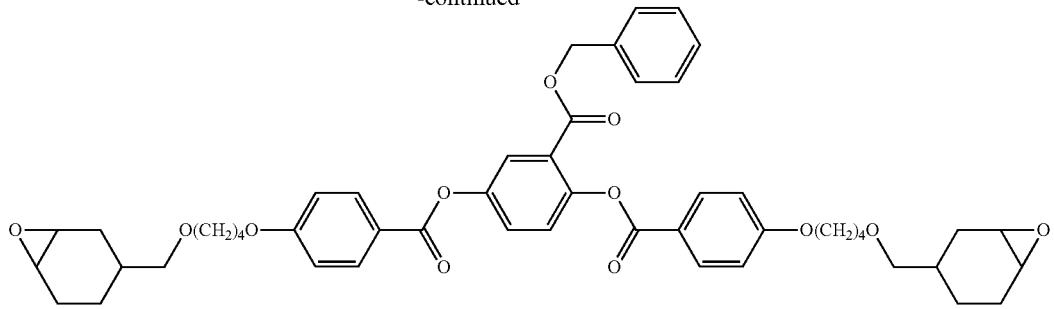

1-B-47

First Step:

Sodium. hydroxide (4.4 mol) was added to water (300 mL)) with stirring under an atmosphere of nitrogen. Cyclohexenemethanol (0.89 mol), tetrabutylammonium bromide (TBAB; 0.089 mol) and 1,4-dibromobutane (1.8 mol) were added thereto and the mixture was stirred at 100° C. for another 5 hours. The organic phase was separated and washed sequentially with an aqueous 5% solution of sodium hydrogencarbonate and an aqueous 10% solution of sodium chloride, and then dried over anhydrous sulfate. The solvent was distilled off under reduced pressure. The residue was purified by means of column chromatography, giving colorless oil of the compound (ex-4-2).

Next, the resultant compound (ex-4-2) (0.52 mol), methyl 4-hydroxybenzoate (0.57 mol) and potassium hydroxide (0.57 mol) were added to dimethylformamide (DMF; 700 mL) and the mixture was stirred under an atmosphere of nitrogen at 80° C. for 5 hours. Toluene (500 mL) and water (500 mL) were added to the reaction solution and an organic phase was separated. The organic phase was washed sequentially with a saturated aqueous solution of sodium hydrogencarbonate and water, and the solvent was distilled off under reduced pressure.

Next, methanol (400 mL), water (400 mL) and potassium hydroxide (0.57 mol) were added to the residue and the mixture was heated to reflux with stirring for 3 hours. The solvent was distilled off and 3N-hydrochloric acid (500 mL) and toluene (500 mL) were added, separating an organic phase. The organic phase was washed with water and the solvent was distilled off. Recrystallization from ethanol gave colorless crystals of the compound (ex-4-3) (0.43 mol).

Second Step:

The compound (ex-4-3) (16 mmol), benzyl 2,5-dihydrobenzoate (8.2 mmol) and 4-dimethylaminopyridine (DMAP; 3.3 mmol) were added to dichloromethane (50 mL) and the mixture was stirred under an atmosphere of nitrogen. 1,3-Dicyclohexylcarbodiimide (DCC; 17 mmol) in dichloromethane (10 mL) solution was added thereto. After the addition, the mixture was stirred at room temperature for another 8 hours. Precipitates were filtered off and the organic phase was washed with water, and then dried over anhydrous sulfate. The solvent was distilled off under reduced pressure. The residue was purified by means of column chromatography and recrystallization from ethanol, giving colorless crystals of the compound (ex-4-3).

Next, the compound (ex-4-3) (6.0 mmol) was added to dichloromethane (50 mL) and the solution was stirred under an atmosphere of nitrogen at 5° C. or lower. m-Chloroperoxybenzoic acid (13 mmol) was added thereto and the mixture was stirred at room temperature for another 16 hours. Precipitates was filtered off under reduced pressure and the filtrate was washed sequentially with an aqueous 10% solution of sodium hydrogen sulfite, an aqueous 3% solution of sodium hydroxide and water, and then dried over anhydrous magnesium sulfate. The solvent was distilled off and the residue was purified by means of column chromatography and recrystallization from ethanol, giving the compound (1-B-47) (3.4 mmol). The melting point of the resultant compound (1-B-47) was as follows.

Phase transition temperature: C 51 (N 28) I.

Compounds used in Examples 19 and 20 are shown below.

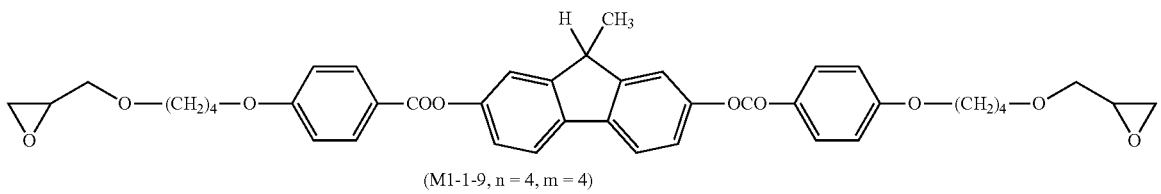

(M1-1-9, n = 4, m = 4)

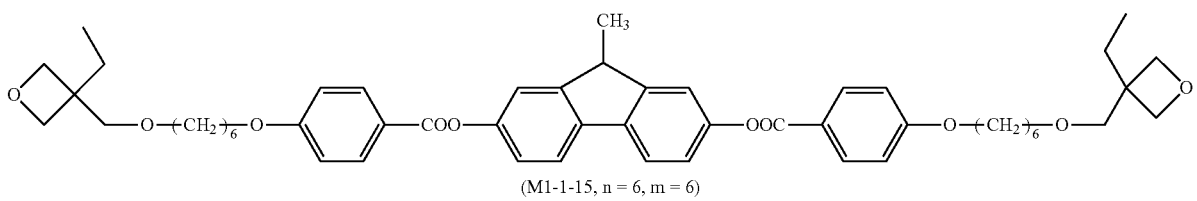

(M1-1-15, n = 6, m = 6)

The compound (M1-1-9) and the compound (M1-1-15) were prepared according to the method described in JP 2005-060373 A.

Example 19

A composition was prepared by mixing the compound (1-B-47)/the compound (M1-1-15) in a weight ratio of 50/50. The composition was referred to as MIX-17. To the MIX-17, a fluorine-based nonionic surfactant (Neos Company Limited; trade name: Futargent FTX-218) in a weight ratio of 0.002 and a polymerization initiator CPI-110P (San-Apro Ltd.) in a weight ratio of 0.03 were added. Cyclopentanone/PGMEA in a ratio of 1/1 (by weight) was added to the composition, preparing the polymerizable liquid crystal composition (23) in which the ratio of the solvent was 80% by weight. The anisotropic polymer was prepared in the same way as described in Example 3, except that the polymerizable liquid crystal composition (23) was polymerized in air instead of polymerization under a stream of nitrogen. An evaluation revealed that the anisotropic polymer had a uniform orientation without orientational defects. It was found that the polymer had a homogeneous orientation since the results of measurement on the retardation of the anisotropic polymer showed a similar tendency to that in FIG. 1, and calculations showed that the optical anisotropy (Δn) was 0.13.

Comparative Example 8

A polymer was obtained from the polymerizable liquid crystal composition (24) that was prepared in the same way as described in Example 19 using the compound (M1-1-15) instead of the MIX-1. An evaluation revealed that the polymer had many orientational defects that were caused by crystallization and the surface was milky white. The retardation of the polymer could hardly be evaluated.

Example 20

A composition was prepared by mixing the compound (1-B-47)/the compound (M1-1-9)/the compound (M1-1-15) in a weight ratio of 75/20/5. The composition was referred to as MIX-18. To the MIX-18, a fluorine-based nonionic surfactant (Neos Company Limited; trade name: Futargent FTX-218) in a weight ratio of 0.002 and a polymerization initiator CPI-110P (San-Apro Ltd.) in a weight ratio of 0.03 were added. Cyclopentanone/PGMEA in a ratio of 1/1 (by weight) was added to the composition, preparing the polymerizable liquid crystal composition (25) in which the ratio of the solvent was 80% by weight. The anisotropic polymer was prepared in the same way as described in Example 3, except that the polymerizable liquid crystal composition (25) was polymerized in air instead of polymerization of under a stream of nitrogen. An evaluation revealed that the anisotropic polymer had a uniform orientation without orientational defects. It was found that the polymer had a homogeneous orientation since the results of measurement on the retardation of the anisotropic polymer showed a similar tendency to that in FIG. 1, and calculations showed that the optical anisotropy (Δn) was 0.13.

Comparative Example 9

A composition was prepared by mixing the compound (M1-1-9)/the compound (M1-1-15) in a weight ratio of 95/5. The composition was referred to as MIX-19. A polymer was obtained from the polymerizable liquid crystal composition (26) that was prepared in the same way as described in Example 20 using the MIX-19 instead of the MIX-18. An evaluation revealed that the polymer had many orientational defects that were caused by crystallization and the surface was milky white. The retardation of the polymer could hardly be evaluated.

It was found from the results in Examples and Comparative Examples described above that the polymerizable compound having a benzyl ester moiety in the minor axis direction of the molecule prevented crystallization of its composition at room temperature. It was also found that in the anisotropic polymer prepared from the polymerizable liquid crystal composition of the invention, an adjustment of the optical anisotropy (Δn) could be possible, while the liquid crystal orientation was maintained.

Applicability in Industry

According to the invention, an anisotropic polymer having a homogeneous orientation or a twisted orientation can be obtained by use of the polymerizable liquid crystal composition including a compound having a benzyl ester moiety in the minor axis direction of the molecule, and thus it is possible to adjust the optical anisotropy.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A polymerizable liquid crystal compound represented by formula (1):

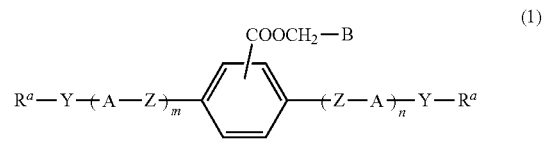

wherein
at least one of $R^a$ is a polymerizable group which is a substituent selected from the group of substituents represented by formulas (a-1) to (a-9),

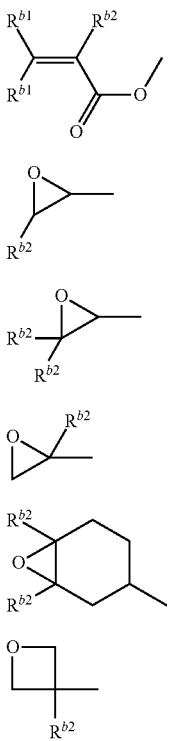

(a-4)

(a-5)

(a-6)

(a-7)

(a-8)

(a-9)

and $R^a$ that is not a polymerizable group is chlorine, fluorine, cyano, alkyl having 1 to 10 carbons, alkoxy having 1 to 10 carbons, —$CF_3$ or —$OCF_3$;

A is independently 1,4-cyclohexylene, 1,4-cyclohexenylene, 1,3-dioxane-2,5-diyl, pyridine-2,6-diyl, pyridazine-3,6-diyl, pyrimidine-2,6-diyl, naphthalene-2,6-diyl, tetrahydronaphthalene-2,6-diyl, fluorene-2,7-diyl, bicyclo[2.2.2]octane-1,4-diyl, or 1,4-phenylene in which arbitrary hydrogen may be replaced by halogen, cyano, —$NO_2$, alkyl having 1 to 5 carbons or halogenated alkyl having 1 to 5 carbons;

B is phenyl in which arbitrary hydrogen may be replaced by halogen, cyano, —$NO_2$, alkyl having 1 to 5 carbons, halogenated alkyl having 1 to 5 carbons, alkoxy having 1 to 5 carbons or halogenated alkoxy having 1 to 5 carbons;

Z is independently a single bond or alkylene having 1 to 20 carbons, and in the alkylene, arbitrary —$CH_2$— may be replaced by —O—, —CO—, —COO—, —OCO—, —CH=CH—, —CF=CF— or —C≡C—, and arbitrary hydrogen may be replaced by halogen;

Y is independently a single bond or alkylene having 1 to 20 carbons, and in the alkylene, arbitrary —$CH_2$— may be replaced by —O—, —CO—, —COO—, —OCO—, —OCOO— or —CH=CH—, and arbitrary hydrogen may be replaced by halogen;

m and n are each independently an integer from 0 to 5; and $R^{b1}$ and $R^{b2}$ are each independently hydrogen, halogen, alkyl having 1 to 5 carbons or halogenated alkyl having 1 to 5 carbons.

2. The polymerizable liquid crystal compound according to claim 1, wherein the polymerizable group is a substituent represented by formula (a-4):

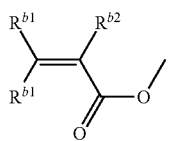

(a-4)

wherein $R^{b1}$ and $R^{b2}$ are each independently hydrogen, halogen, alkyl having 1 to 5 carbons or halogenated alkyl having 1 to 5 carbons.

3. The polymerizable liquid crystal compound according to claim 1, wherein in formula (1), the sum of m and n is an integer from 1 to 3.

4. The polymerizable liquid crystal compound according to claim 1, wherein in formula (1), the sum of m and n is 2.

5. The polymerizable liquid crystal compound according to claim 1, wherein in formula (1), A is independently 1,4-cyclohexylene, pyridine-2,5-diyl, pyridazine-3,6-diyl, pyrimidine-2,5-diyl, or 1,4-phenylene in which arbitrary hydrogen may be replaced by chlorine, fluorine, cyano, alkyl having 1 to 3 carbons or fluoroalkyl having 1 to 3 carbons; and B is phenyl in which arbitrary hydrogen may be replaced by fluorine, cyano, —$NO_2$, alkyl having 1 to 3 carbons, fluoroalkyl having 1 to 3 carbons, alkoxy having 1 to 3 carbons or fluoroalkoxy having 1 to 3 carbons.

6. The polymerizable liquid crystal compound according to claim 5, wherein in formula (1), A is independently 1,4-cyclohexylene, or 1,4-phenylene in which arbitrary hydrogen may be replaced by chlorine, fluorine, cyano, —$CH_3$ or —$CF_3$; and B is phenyl in which arbitrary hydrogen may be replaced by fluorine, cyano, —$NO_2$ or —$OCF_3$.

7. The polymerizable liquid crystal compound according to claim 1, wherein in formula (1), Z is independently a single bond, —$CH_2O$—, —$OCH_2$—, —COO—, —OCO—, —CH=CH—, —$(CH_2)_2COO$—, —$OCO(CH_2)_2$—, —CH=CHCOO—, —OCOCH=CH— or —C≡C—.

8. The polymerizable liquid crystal compound according to claim 1, wherein in formula (1), Z is independently a single bond, —$CH_2O$—, —$OCH_2$—, —COO— or —OCO—.

9. The polymerizable liquid crystal compound according to claim 1, wherein in formula (1), Y is independently alkylene having 1 to 12 carbons, and in the alkylene, arbitrary —$CH_2$— may be replaced by —O—, —COO—, —OCO— or —OCOO—.

10. A polymerizable liquid crystal composition, comprising at least one of compounds according to claim 1.

11. A polymerizable liquid crystal composition, comprising at least one of polymerizable liquid crystal compounds represented by formula (1) and at least one polymerizable liquid crystal compound selected from the group of compounds represented by formula (M1), formula (M2-1) to formula (M2-5), formula (M3) and formula (M4):

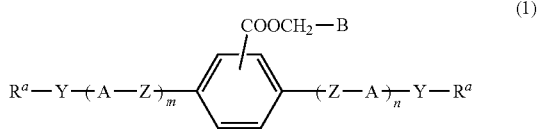

(1)

wherein at least one of $R^a$ is a polymerizable group and is a substituent selected from the group of substituents represented by formula (a-1) to formula (a-9), and $R^a$ that is not a polymerizable group is chlorine, fluorine, cyano, alkyl having 1 to 10 carbons, alkoxy having 1 to 10 carbons, —CF$_3$ or —OCF$_3$;

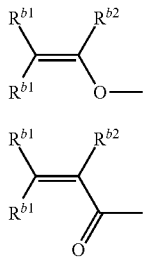
(a-1)

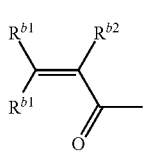
(a-2)

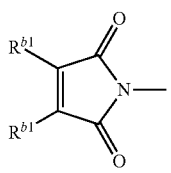
(a-3)

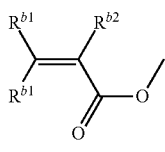
(a-4)

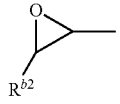
(a-5)

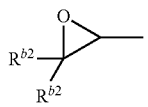
(a-6)

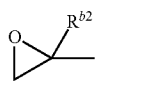
(a-7)

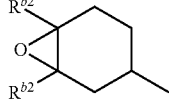
(a-8)

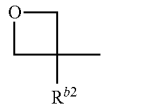
(a-9)

in formula (a-1) to formula (a-9), $R^{b1}$ and $R^{b2}$ are each independently hydrogen, halogen, alkyl having 1 to 5 carbons or halogenated alkyl having 1 to 5 carbons;

A is independently 1,4-cyclohexylene, 1,4-cyclohexenylene, 1,3-dioxane-2,5-diyl, pyridine-2,6-diyl, pyridazine-3,6-diyl, pyrimidine-2,6-diyl, naphthalene-2,6-diyl, tetrahydronaphthalene-2,6-diyl, fluorene-2,7-diyl, bicyclo[2.2.2]octane-1,4-diyl, or 1,4-phenylene in which arbitrary hydrogen may be replaced by halogen, cyano, —NO$_2$, alkyl having 1 to 5 carbons or halogenated alkyl having 1 to 5 carbons;

B is phenyl in which arbitrary hydrogen may be replaced by halogen, cyano, —NO$_2$, alkyl having 1 to 5 carbons, halogenated alkyl having 1 to 5 carbons, alkoxy having 1 to 5 carbons or halogenated alkoxy having 1 to 5 carbons;

Z is independently a single bond or alkylene having 1 to 20 carbons, and in the alkylene, arbitrary —CH$_2$— may be replaced by —O—, —CO—, —COO—, —OCO—, —CH=CH—, —CF=CF— or —C≡C—, and arbitrary hydrogen may be replaced by halogen;

Y is independently a single bond or alkylene having 1 to 20 carbons, and in the alkylene, arbitrary —CH$_2$— may be replaced by —O—, —CO—, —COO—, —OCO—, —OCOO— or —CH=CH—, and arbitrary hydrogen may be replaced by halogen; and m and n are each independently an integer from 0 to 5; and

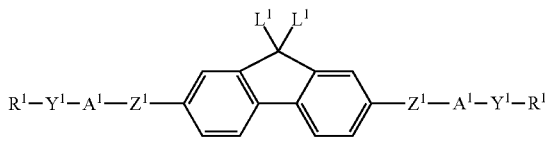
(M1)

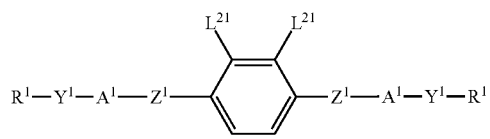
(M2-1)

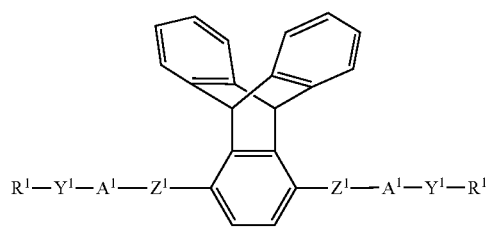
(M2-2)

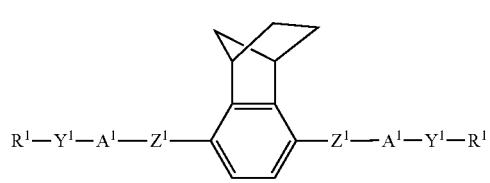
(M2-3)

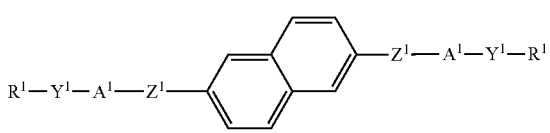
(M2-4)

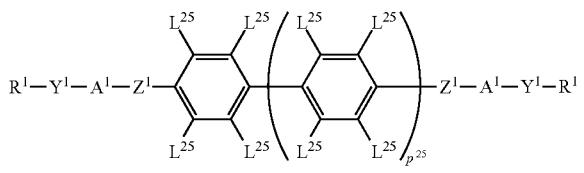
(M2-5)

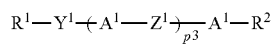
(M3)

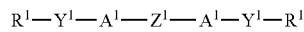
(M4)

wherein
- $R^1$ is independently a substituent represented by formula (a-4), formula (a-5) or formula (a-9) described above;
- $R^2$ is alkyl having 1 to 10 carbons, alkoxy having 1 to 10 carbons, chlorine, fluorine, cyano, —$CF_3$ or —$OCF_3$;
- $A^1$ is independently 1,4-cyclohexylene, or 1,4-phenylene in which arbitrary hydrogen may be replaced by fluorine;
- $Z^1$ is independently a single bond, —$CH_2CH_2$—, —$CH_2O$—, —$OCH_2$—, —COO—, —OCO—, —CH=CH—, —C≡C—, —CH=CHCOO—, —OCOCH=CH—, —$(CH_2)_2$COO— or —OCO$(CH_2)_2$—;
- $Y^1$ is independently a single bond or alkylene having 1 to 20 carbons, and in the alkylene, arbitrary —$CH_2$— may be replaced by —O—, —CO—, —COO—, —OCO—, —OCOO— or —CH=CH—;
- $L^1$ is independently hydrogen, fluorine or —$CH_3$;
- $L^{21}$ is independently hydrogen, halogen, cyano, alkyl having 1 to 8 carbons or halogenated alkyl having 1 to 8 carbons;
- $L^{25}$ is independently hydrogen, halogen, alkyl having 1 to 8 carbons, alkoxy having 1 to 8 carbons, cyano or halogenated alkyl having 1 to 8 carbons;
- $p^{25}$ is 1 or 2; and
- $p^3$ is 1 or 2.

12. The polymerizable liquid crystal composition according to claim 11, wherein
- in formula (1), a polymerizable group is a substituent represented by formula (a-4), formula (a-5) or formula (a-9); A is independently 1,4-cyclohexylene, pyridine-2,5-diyl, pyridazine-3,6-diyl, pyrimidine-2,5-diyl, or 1,4-phenylene in which arbitrary hydrogen may be replaced by chlorine, fluorine, cyano, alkyl having 1 to 3 carbons or fluoroalkyl having 1 to 3 carbons; B is phenyl in which arbitrary hydrogen may be replaced by fluorine, cyano, —$NO_2$, alkyl having 1 to 3 carbons, fluoroalkyl having 1 to 3 carbons, alkoxy having 1 to 3 carbons or fluoroalkoxy having 1 to 3 carbons; Z is independently a single bond, —$CH_2O$—, —$OCH_2$—, —COO—, —OCO—, —CH=CH—, —$(CH_2)_2$COO—, —OCO$(CH_2)_2$—, —CH=CHCOO—, —OCOCH=CH— or —C≡C—; Y is independently a single bond or alkylene having 1 to 10 carbons, and in the alkylene, arbitrary —$CH_2$— may be replaced by —O—, —COO—, —OCO— or —OCOO—; and m and n is 1; and
- in formula (M1), formula (M2-1) to formula (M2-5), formula (M3) and formula (M4), $R^1$ is independently a substituent represented by formula (a-4), formula (a-5) or formula (a-9); $R^2$ is alkyl having 1 to 8 carbons, alkoxy having 1 to 8 carbons, chlorine, fluorine, cyano, —$CF_3$ or —$OCF_3$; $A^1$ is independently 1,4-cyclohexylene, 1,4-phenylene, monofluoro-1,4-phenylene or difluoro-1,4-phenylene; $Z^1$ is independently a single bond, —$CH_2O$—, —$OCH_2$—, —COO—, —OCO—, —C≡C—, —CH=CHCOO—, —OCOCH=CH—, —$(CH_2)_2$COO— or —OCO$(CH_2)_2$—; $Y^1$ is independently a single bond or alkylene having 1 to 12 carbons, and in the alkylene, arbitrary —$CH_2$— may be replaced by —O—, —COO—, —OCO— or —OCOO—; $L^1$ is independently hydrogen, fluorine or —$CH_3$; $L^{21}$ is independently hydrogen, halogen, cyano, alkyl having 1 to 5 carbons or halogenated alkyl having 1 to 5 carbons; $L^{25}$ is independently hydrogen, halogen, cyano, alkyl having 1 to 5 carbons, alkoxy having 1 to 5 carbons or halogenated alkyl having 1 to 5 carbons; $p^{25}$ is 1 or 2; and $p^3$ is 1 or 2; and
- and the ratio of a polymerizable liquid crystal compound represented by formula (1) is in the range of approximately 3% to approximately 90% by weight and the ratio of a polymerizable compound selected from the group of compounds represented by formula (M1), formula (M2-1), formula (M2-2) to formula (M2-5), formula (M3) and formula (M4) is in the range of approximately 10% to approximately 97% by weight, based on the total weight of the polymerizable liquid crystal compound represented by formula (1) and the polymerizable compound selected from the group of compounds represented by formula (M1), formula (M2-1) to formula (M2-5), formula (M3) and formula (M4).

13. The polymerizable liquid crystal composition according to claim 11, wherein
- in formula (1), a polymerizable group is independently a substituent represented by formula (a-4), formula (a-5) or formula (a-9); A is independently 1,4-cyclohexylene, or 1,4-phenylene in which arbitrary hydrogen may be replaced by chlorine, fluorine, —$CH_3$ or —$CF_3$; B is phenyl in which arbitrary hydrogen may be replaced by fluorine, cyano, —$NO_2$ or —$OCF_3$; Z is independently a single bond, —COO— or —OCO—; Y is independently alkylene having 1 to 10 carbons, and in the alkylene, —$CH_2$— bonded to the ring A may be replaced by —O—, —COO, —OCO— or —OCOO—; and m and n is 1; and
- in formula (M1), formula (M2-1) to formula (M2-5), formula (M3) and formula (M4), $R^1$ is independently a substituent represented by formula (a-4), formula (a-5) or formula (a-9); $R^2$ is alkyl having 1 to 8 carbons, alkoxy having 1 to 8 carbons, cyano, fluorine or —$OCF_3$; $A^1$ is independently 1,4-cyclohexylene, 1,4-phenylene, monofluoro-1,4-phenylene or difluoro-1,4-phenylene; $Z^1$ is independently a single bond, —COO—, —OCO—, —CH=CHCOO—, —OCOCH=CH—, —$(CH_2)_2$COO— or —OCO$(CH_2)_2$—; $Y^1$ is independently a single bond or alkylene having 1 to 10 carbons, and in the alkylene, —$CH_2$— that is bonded to the ring $A^1$ may be replaced by —O—, —COO—, —OCO— or —OCOO—; $L^1$ is independently hydrogen or —$CH_3$; $L^{21}$ is independently hydrogen, fluorine, methyl, cyano, isopropyl, tert-butyl or trifluoromethyl; $L^{25}$ is independently hydrogen, fluorine, methyl, or methoxy; $p^{25}$ is 1 or 2; and $p^3$ is 2; and
- and the ratio of a polymerizable liquid crystal compound represented by formula (1) is in the range of approximately 15% to approximately 80% by weight, and the ratio of a polymerizable liquid crystal compound selected from the group of compounds represented by formula (M1), formula (M2-1) to formula (M2-5), formula (M3) and formula (M4) is in the range of approximately 20% to approximately 85% by weight, based on the total weight of the polymerizable liquid crystal compound represented by formula (1), and the polymerizable compound selected from the group of compounds represented by formula (M1), formula (M2-1) to formula (M2-5), formula (M3) and formula (M4).

14. The polymerizable liquid crystal composition according to claim 11, further comprising a polymerizable compound that is not optically active and is different from compounds represented by formula (1), formula (M1), formula (M2-1) to formula (M2-5), formula (M3) and formula (M4).

15. The polymerizable liquid crystal composition according to claim 11, further comprising a polymerizable and optically active compound.

16. The polymerizable liquid crystal composition according to claim 11, further comprising a non-polymerizable liquid crystal compound.

17. The polymerizable liquid crystal composition according to claim 11, further comprising a non-polymerizable and optically active compound.

18. A polymer film formed by polymerization of the polymerizable liquid crystal compound according to claim 11.

19. An anisotropic polymer formed by polymerization of the polymerizable liquid crystal compound according to claim 11.

20. The anisotropic polymer according to claim 19, wherein the orientational mode of the polymerizable liquid crystal composition is any one of a homogeneous orientation, a tilted orientation, a twisted orientation and a homeotropic orientation.

21. The anisotropic polymer according to claim 19, wherein the orientational mode of the polymerizable liquid crystal composition is adjusted by any one of rubbing treatment, photo-alignment treatment, ion beam treatment, corona treatment and plasma treatment.

22. The anisotropic polymer according to claim 19, wherein the orientational mode of the polymerizable liquid crystal composition is adjusted by any one of rubbing treatment, photo-alignment treatment, corona treatment and plasma treatment.

23. The anisotropic polymer according to claim 19, wherein the anisotropic polymer is formed on a glass substrate.

24. The anisotropic polymer according to claim 19, wherein the anisotropic polymer is formed on a glass substrate that has been coated with a plastic thin film, or formed on a plastic substrate composed of a plastic film.

25. The anisotropic polymer according to claim 24, wherein plastic that is a material of the plastic thin film and the plastic film is selected from polyimides, polyamideimides, polyamides, polyetherimides, polyetheretherketones, polyetherketones, polyketonesulfides, polyethersulfones, polysulfones, polyphenylenesulfides, polyphenyleneoxides, polyethylenes terephthalates, polybutylene terephthalates, polyethylene naphthalates, polyacetals, polycarbonates, polyacrylates, acrylic resins, polyvinyl alcohols, polypropylenes, celluloses, triacetyl celluloses, partially saponified products of triacetylcelluloses, epoxy resins, phenol resins and cycloolefin-based resins.

26. The anisotropic polymer according to claim 24, wherein plastic that is a material of the plastic thin film and the plastic film is selected from polyimides, polyvinyl alcohols, triacetyl celluloses, partially saponified products of triacetylcelluloses and cycloolefin-based resins.

27. An optical compensation film having the anisotropic polymer according to claim 19.

28. A reflection film having the anisotropic polymer according to claim 19.

29. A liquid crystal display element containing the optical compensation film according to claim 27.

30. A liquid crystal display element containing the reflection film according to claim 28.

31. A liquid crystal display device containing the optical compensation film according to claim 27.

32. A liquid crystal display device containing the reflection film according to claim 28.

* * * * *